United States Patent [19]
Conaway et al.

[11] Patent Number: 6,084,068
[45] Date of Patent: Jul. 4, 2000

[54] ELONGIN A AND C FUNCTIONAL DOMAINS

[75] Inventors: Ronald C. Conaway; Joan W. Conaway, both of Oklahoma City, Okla.

[73] Assignee: Oklahoma Medical Research Foundation, Oklahoma City, Okla.

[21] Appl. No.: 08/725,459

[22] Filed: Oct. 4, 1996

[51] Int. Cl.⁷ ...................................................... C07K 5/00
[52] U.S. Cl. ............................................................ 530/350
[58] Field of Search ............................................. 530/350

[56] References Cited

U.S. PATENT DOCUMENTS

| | | | |
|---|---|---|---|
| 5,310,667 | 5/1994 | Eichholtz et al. | 435/172.3 |
| 5,464,756 | 11/1995 | Henner et al. | 435/69.1 |

FOREIGN PATENT DOCUMENTS

| | | | |
|---|---|---|---|
| 655498 A1 | 5/1995 | European Pat. Off. | C12N 15/12 |

OTHER PUBLICATIONS

Database Swissprot; YRL4 CAEEL (AC 009413), Oct. 1, 1996, Swinburne J.: "Hypothetical 49.2 kd Protein R03D7.4 in Chromosome II,"XP002055270.

Tan, et al., "Dissection of transcription factor TFIIF functional domains required for initiation and elongation," *Proc Natl Acad Sci USA* 92:6042–6046 (Jun., 1995).

Aso, et al., "The RNA polymerase II elongation complex," *FASEB J* 9:1419–1428 (1995).

Aso, et al., "Elongin (SIII): a multisubunit regulator of elongation by RNA polymerase II," *Science* 269:1439–1443 (1995).

Bradsher, et al., "RNA polymerase II transcription factor SIII. I. Identification, purification and properties," *J Biol Chem* 268:25587–25593 (1993).

Bradsher, et al., "RNA polymerase II transcription factor SIII. II. Functional properties and role in RNA chain elongation," *J Biol Chem* 268:25594–25603 (1993).

Chen, et al., "Characterization of a HeLa cDNA clone encoding the human SII protein, an elongation factor for RNA polymerase II," *Gene* 116:253–258 (1992).

Chen, et al., "Germline mutations in the von Hippel–Lindau disease tumor suppressor gene: correlations with phenotype," *Human Mutation* 5:66–75 (1995).

Cipres–Palacin, G. and Kane, C.M., "Cleavage of the nascent transcript induced by TFIIS in insufficient to promote read–through of intrinsic blocks to elongation by RNA polymerase II," *Proc Natl Acad Sci USA* 91:8087–8091 (1994).

Conaway, R.C. and Conaway, J.W., "General initiation factors for RNA polymerase II," *Annu Rev Biochem* 62:161–190 (1993).

Conaway, et al., "Mechanism of assembly of the RNA polymerase II preinitiation complex," *J Biol Chem* 267:10142–10148 (1992).

Conaway, et al., "Transcription initiated by RNA polymerase II and transcription factors from liver," *J Biol Chem* 266:7804–7811 (1991).

Conaway, J.W. and Conaway, R.C., "An RNA polymerase II transcription factor shares functional properties with *Esherichia coli*, " *Science* 248:1550–1553 (1990).

Conaway, R.C. and Conaway, J.W., "ATP activates transcription initiation from promoters by RNA polymerase II in a reversible step prior to RNA synthesis," *J Biol Chem* 263:2962–2968 (1988).

Duan, et al., "Characterization of the VHL tumor suppressor gene product: localization, complex formation, and the effect of natural inactivating mutations," *Proc Natl Acad Sci USA* 92:6459–6463 (1995).

Duan, et al., "Inhibition of transcription elongation by the VHL tumor suppressor protein," *Science* 269:1402–1406 (1995).

Eng, et al., "Mapping of the active site tyrosine of eukaryotic DNA topoisomerase I," *J Biol Chem* 264:13373–13376 (1989).

Foster, et al., "Somatic mutations of the von Hippel–Lindau disease tumour suppressor gene in non–familial clear cell renal carcinoma," *Human Molecular Genetics* 3:2169–2173 (1994).

Garrett, et al., "Positive regulation of general transcription factor SIII by a tailed ubiquitin homolog," *Proc Natl Acad Sci USA* 92:7172–7176 (1995).

Garrett, et al., "Molecular cloning of an essential subunit of RNA polymerase II elongation factor SIII," *Proc Natl Acad Sci USA* 91:5237–5241 (1994).

Gnarra, et al., "Mutations of the VHL tumour suppressor gene in renal carcinoma," *Nat Genet* 7:85–90 (1994).

Gorbalenya, et al., "Two related superfamilies of putative helicases involved in replication, recombination, repair, and expression of DNA and RNA genomes," *Nucleic Acids Res* 17:4713–4730 (1989).

Iliopoulos, et al., "Tumour suppression by the human von Hippel–Lindau gene product," *Nature Medicine* 1:822–826 (1995).

Ingraham, et al., "The POU–specific domain of Pit–1 is essential for sequence–specific, high affinity DNA binding and DNA–dependent Pit–1–Pit–1 interactions," *Cell* 61:1021–1033 (1990).

Kadesch, T.R. and Chamberlin, M.J., "Studies of in vitro transcription by calf thymus RNA polymerase II using a novel duplex DNA template," *J Biol Chem* 257:5286–5295 (1982).

Kane, C.M., "Transcript elongation and gene regulation in eukaryotes," *Transcription: Mechanisms and Regulation,* R.C. Conaway and J.W. Conaway, eds., Raven Press, New York, pp. 279–296 (1994).

Kanno, et al., "Somatic mutations of the von Hippel–Lindau tumor suppressor gene in sporadic central nervous system hemangioblastomas," *Cancer Research* 54:4845–4847 (1994).

(List continued on next page.)

*Primary Examiner*—James Ketter
*Assistant Examiner*—William Sandals
*Attorney, Agent, or Firm*—Sidley & Austin

[57] ABSTRACT

The functional domains of Elongin A having transcriptional activation activity and Elongin BC binding activity and the functional domains of Elongin C having Elongin A activation activity and Elongin A and/or Elongin C binding activity have now been identified and isolated.

13 Claims, 29 Drawing Sheets

OTHER PUBLICATIONS

Kibel, et al., "Binding of the von Hippel–Lindau tumor suppressor protein to Elongin B and C," *Science* 269:1444–1446 (1995).

Krumm, et al., "Promoter–proximal pausing of RNA polymerase II defines a general rate–limiting step after transcription initiation," *Genes Dev* 9:559–572 (1995).

Latif, et al., "Identification of the von Hippel–Lindau disease tumor suppressor gene," *Science* 260:1317–1320 (1993).

Lynn, et al., "Peptide sequencing and site–directed mutagenesis identify tyrosine–727 as the active site tyrosine of *Saccharomyces cerevisiae* DNA topoisomease I," *Proc Natl Acad Sci USA* 86:3559–3563 (1989).

Marshall, N.F. and Price, D.H., "Purification of P–TEFb, a transcription factor required for the transition into productive elongation," *J Biol Chem* 270:12335–12338 (1995).

Marshall, N.F. and Price, D.H., "Control of formation of two distinct classes of RNA polymerase II elongation complexes," *Mol Cell Biol* 12:2078–2090 (1992).

Marshall, et al., "Drosophila RNA polymerase II elongation factor DmS–II has homology to mouse S–II and sequence similarity to yeast PPR2," *Nucleic Acids Res* 18:6293–6298 (1990).

Mitani, et al., "Cloning of several species of MLL/MEN chimeric cDNAs in myeloid leukemia with t(11;19)(q23;p13.1) translocation," *Blood* 85:2017–2024 (1995).

Mitchell, P.J. and Tijan, R., Transcriptional regulation in mammalian cells by sequence–specific DNA binding proteins, *Science* 245:371–378 (1989).

Nakanishi, et al., "Structure–function relationship of yeast S–II terms of stimulation of RNA polymerase II, arrest relief, and suppression of 6–azauracil sensitivity," *J Biol Chem* 270:8991–8995 (1995).

Price, et al., "Dynamic interaction between a Drosophila transcription factor and RNA polymerase II," *Mol Cell Biol* 9:1465–1475 (1989).

Reines, D., "Elongation factor–dependent transcript shortening by template–engaged RNA polymerase II," *J Biol Chem* 267:3795–3800 (1992).

Shilatifard, et al., An RNA polymerase II elongation factor encoded by the human ELL gene, *Science* 271:1873–1876 (1996).

Tan, et al., "Roles for both the RAP30 and RAP74 subunits of transcription factor IIF in transcription initiation and elongation by RNA polymerase II," *J Biol Chem* 269:25684–25691 (1994).

Thirman, et al., "Cloning of ELL, a gene that fuses to MLL in a t(11;19)(q23;p13.1) in acute myeloid leukemia," *Proc Natl Acad Sci USA* 91:12110–12114 (1994).

Walker, et al., "Distantly related sequences in the α–and β–subunits of ATP synthase, myosin, kinases and other ATP–requiring enzymes and a common nucleotide binding fold," *EMBO J* 1:945–951 (1982).

Whaley, et al., "Germ–line mutations in the von Hippel–Lindau tumor-suppressor gene are similar to somatic Hippel–Lindau aberrations in sporadic renal cell carcinoma," *Am J Hum Genet* 55:1092–1102 (1994).

Yankulov, et al., "Transcriptional elongation by RNA polymerase II is stimulated by transactivators," *Cell* 77:749–759 (1994).

| | | | | | | | |
|---|---|---|---|---|---|---|---|
| Rat | M A A E S A L Q V V | E K L Q A R A A N | P D P K K L K Y L | K K S V L P I T V | D I L V E T G V G K | T V N S F R K H E Q | 60 |
| C. elegans | M - P E T D E E K V | R R Y T E C L M N G | I D P K R A L K R L | Y D L N V S P - - - | E V F K S A D T V Q | C V K R Y E S S P E | 56 |
| Rat | V G N F A R - - - - | D V A Q W K K L V | P V E R N N E A E D | Q D F E K S N S R K | - R P R D V P Q G E | E E A E G - N Y Q E | 114 |
| C. elegans | L A K Y A K R V R D | K L L G G R K R - - | - - E K G G E D D | A D I E H T A L K K | A K K E E V N L D E | E F A E A M K S G V | 112 |
| Rat | S W Q A S G S Q P Y | S P E H R Q K K H R | K L P E L E R P H K | V A H G H E R R D E | R K R C H K V S P P | Y S S D P E S S D Y | 174 |
| C. elegans | S A Q A S S A P R A | T V D Y S K Y K V | K R V K V E P K | P E P V D V H E G Q | A S S S - - S M S | Y Q R E H Q K D - - | 167 |
| Rat | G H V Q S P P P S S | P H Q M Y T D L S R | S P E M D Q E P I V | S H P K P G K V H S | N T F Q D R L G V S | H L G E H Q G K G A | 234 |
| Rat | V S Q N K P H K S S | H K E K R P V D A R | G D E K S S V M G R | E K S H K A S S K E | E S R R L L S E D S | A K E K L P S S V V | 294 |
| Rat | K K E K D R E G N S | L K K K L S P A L D | V A S D N H F K K P | K H K D S E K I K S | D K N K Q S V D S V | D S G R G T G D P L | 354 |
| Rat | P R A K D K V P N N | L K A Q E G K V R T | N S D R K S P G S L | P K V E E M D M D D | E F E Q P T M S F E | S Y L S Y D Q P R K | 414 |
| Rat | K K K K V V K T S G | T A L G E K G L K K | K D S K S T S K N L | N S A Q K L P K A N | E N K S D K L Q P A | G A E P T R P R K V | 474 |
| Rat | P T D V L P A L P D | - I P L P A I Q T N Y | R L P S L E L I S | S F Q P K R K A F S | S P Q E E E A G F | T G R R M N S K M Q | 534 |
| C. elegans | - - - - - - - - - - | - - - Y - - - - - - | A V V P T C K P S | G Q P K K A I P Q S | K S L H A D E N M F | K P R K - - E R Q K | 206 |
| Rat | V Y S G S K C A Y L | P K M M T H Q Q C | I R V L K N N T D S | I F E V G G V P Y S | V E P V E R C T | P D Q L Y R E E C | 595 |
| C. elegans | F A G R R K R V G | E G V S T L V S L C | Q T V L M S H I D M | D H V G I V P F D | L L K P V L D H A S | T D Q L R H L D V | 266 |
| Rat | N H V E E T D Q | L W K V H C H R D F | K - E R P E E Y | E S W R E M Y L R L | - - Q D A R E Q | R L L T N N T R | 648 |
| C. elegans | N P M L V E D A D E | M F H E M V S R E F | P K Y A N R E K S G | W T W R E M Y D R L | V E K Q K K E N D | K L E M L I S R L G | 326 |
| Rat | S A H A N K P K G R | Q A K M A F V N S V | A K P P R D V R R R | Q E K F G T G G A A | V P E K V R I K P A | P Y T T G S S H V P | 708 |
| C. elegans | K S N S A Q S Q G R | Q T M V I - - - - - | - - - - - - - - - - | - - - - - - - - D M | A H T R V R S K S F | F N T V K D S Q V K | 363 |
| Rat | A S N S S S F H S | S - - P E E L A Y E | G P S - - T S S A | H L A P V A S S V | S Y D P R K P - - - | - - A V K K I A P | 757 |
| C. elegans | M S A T P S A L Q L | S Q A R K N V K I E | G K A Q L R I I T P | R G G G V P S T S R | S R S N N N N M N | N G L V V K K T A P | 423 |
| Rat | M M A K T I K A F K | N R F S R R  773 | | | | | |
| C. elegans | L M A K C K K M L K | R  434 | | | | | |

```
                     1            14 18  22  28              42              56              70              84              98             112
His Elongin C        M-HHHHHHHNVD-DGEEKTYGGCEGPDAMYVKLISSDGHEFIVKREHALTSGTIKAMLSGPGQFAENETNEVNFREIPSHVLSKVCMYFTYKVRYTNSSTEIPEFPIAPEIALELLMAANFLDC
C(Ala19-21)          M-HHHHHHHNVD-DGEEKTYGGCEGPDAMYVKLISSDGHEFIVKREHALTSGTIKAMLSGPGQFAENETNEVNFREIPSHVLSKVCMYFTYKVRYTNSSTEIPEFPIAPEIALELLMAANFLDC
C(Ala22-24)          M-HHHHHHHNVD-DGEEKTYGGCEGPDAMYAAAISSDGHEFIVKREHALTSGTIKAMLSGPGQFAENETNEVNFREIPSHVLSKVCMYFTYKVRYTNSSTEIPEFPIAPEIALELLMAANFLDC
C(Ala25-27)          M-HHHHHHHNVD-DGEEKTYGGCEGPDAMYVKLAAADGHEFIVKREHALTSGTIKAMLSGPGQFAENETNEVNFREIPSHVLSKVCMYFTYKVRYTNSSTEIPEFPIAPEIALELLMAANFLDC
C(Ala28-30)          M-HHHHHHHNVD-DGEEKTYGGCEGPDAMYVKLISSAAAEFIVKREHALTSGTIKAMLSGPGQFAENETNEVNFREIPSHVLSKVCMYFTYKVRYTNSSTEIPEFPIAPEIALELLMAANFLDC
C(Ala89-91)          M-HHHHHHHNVD-DGEEKTYGGCEGPDAMYVKLISSDGHAAAVKREHALTSGTIKAMLSGPGQFAENETNEVNFREIPSHVLSKVCMYFTYKVRYTNSSTAAAEFPIAPEIALELLMAANFLDC
C(Ala92-94)          M-HHHHHHHNVD-DGEEKTYGGCEGPDAMYVKLISSDGHEFIVKREHALTSGTIKAMLSGPGQFAENETNEVNFREIPSHVLSKVCMYFTYKVRYTNSSTEIPAAAIAPEIALELLMAANFLDC
C(Ala95-97)          M-HHHHHHHNVD-DGEEKTYGGCEGPDAMYVKLISSDGHEFIVKREHALTSGTIKAMLSGPGQFAENETNEVNFREIPSHVLSKVCMYFTYKVRYTNSSTEIPEFPAAAEIALELLMAANFLDC
C(Ala98-100)         M-HHHHHHHNVD-DGEEKTYGGCEGPDAMYVKLISSDGHEFIVKREHALTSGTIKAMLSGPGQFAENETNEVNFREIPSHVLSKVCMYFTYKVRYTNSSTEIPEFPIAPAAALELLMAANFLDC
C(Ala101-103)        M-HHHHHHHNVD-DGEEKTYGGCEGPDAMYVKLISSDGHEFIVKREHALTSGTIKAMLSGPGQFAENETNEVNFREIPSHVLSKVCMYFTYKVRYTNSSTEIPEFPIAPEITAAALMAANFLDC
C(Ala104-106)        M-HHHHHHHNVD-DGEEKTYGGCEGPDAMYVKLISSDGHEFIVKREHALTSGTIKAMLSGPGQFAENETNEVNFREIPSHVLSKVCMYFTYKVRYTNSSTEIPEFPIAPEIALELAAAANFLDC
C(Ala107-109)        M-HHHHHHHNVD-DGEEKTYGGCEGPDAMYVKLISSDGHEFIVKREHALTSGTIKAMLSGPGQFAENETNEVNFREIPSHVLSKVCMYFTYKVRYTNSSTEIPEFPIAPEIALELLMAAALDC
C(Ala110-112)        M-HHHHHHHNVD-DGEEKTYGGCEGPDAMYVKLISSDGHEFIVKREHALTSGTIKAMLSGPGQFAENETNEVNFREIPSHVLSKVCMYFTYKVRYTNSSTEIPEFPIAPEIALELLMAANFAAA
```

Fig. 9B

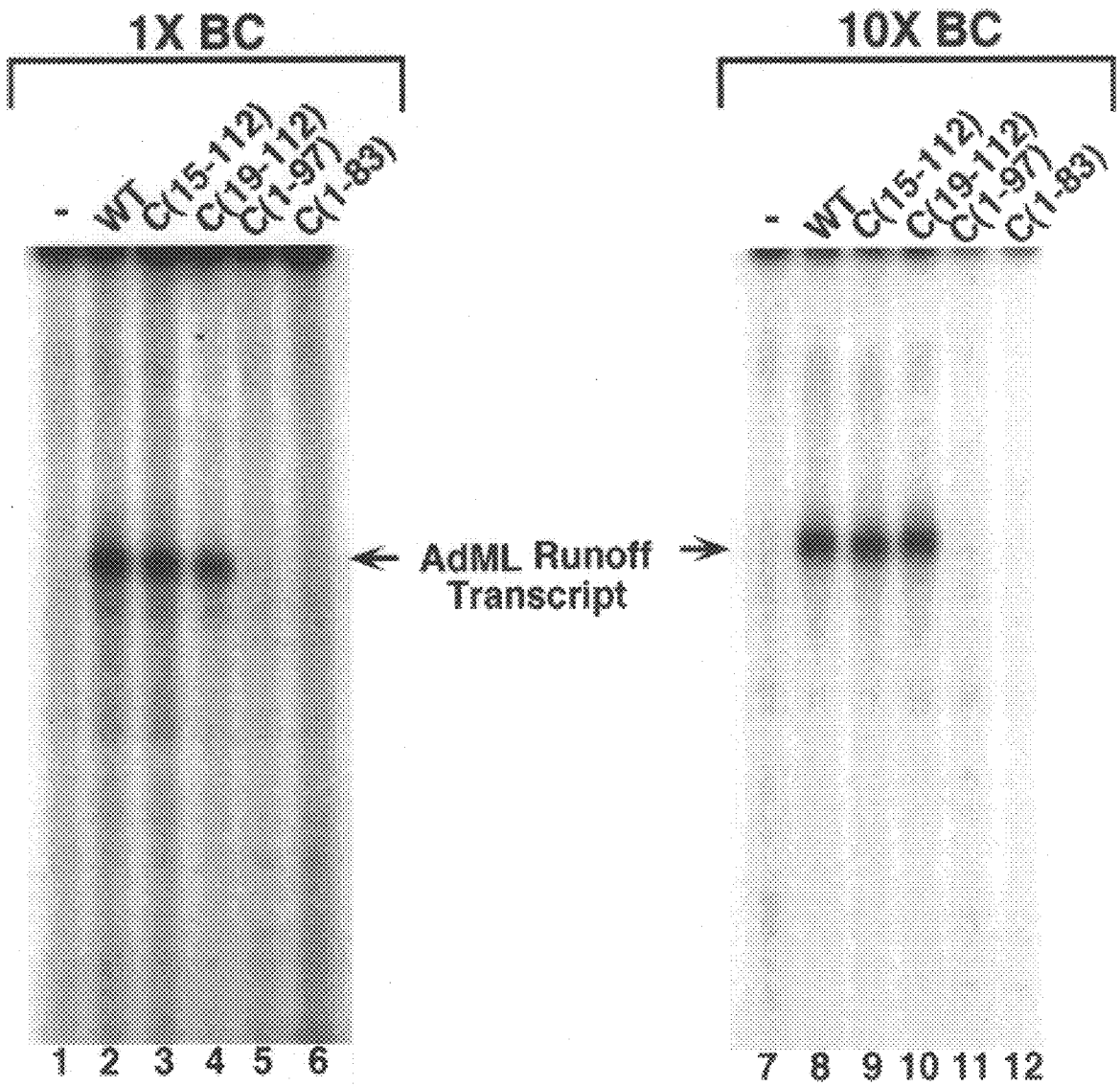
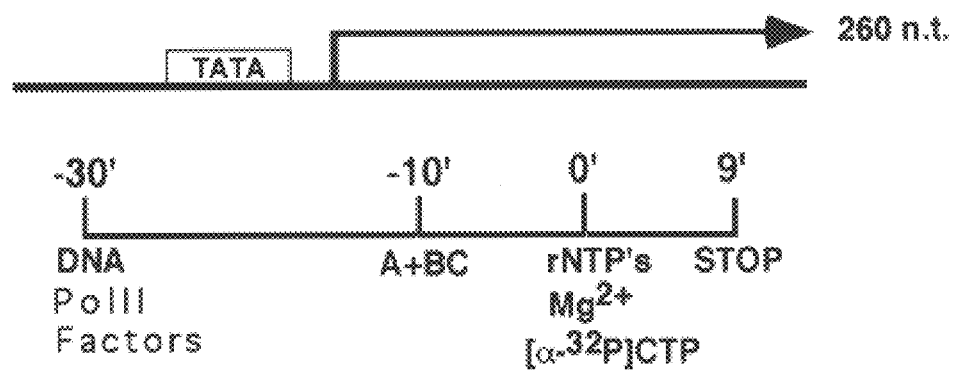
FIG. 11A

ELONGIN A AND C FUNCTIONAL DOMAINS

TECHNICAL FIELD OF THE INVENTION

The invention relates to the identification and characterization of the functional domains of the subunits of the elongation factor Elongin required for transcriptional activation of RNA Polymerase II and the regulation thereof.

BACKGROUND OF THE INVENTION

Transcription is the synthesis of a strand of RNA representing or complementary to the coding strand of a DNA duplex. It takes place by the usual process of complementary base pairing and is catalyzed by the enzyme RNA polymerase. Transcription is the first step in the expression of a gene and it is the principle step at which gene expression is controlled or regulated.

The transcription process can be controlled at any one of the three stages of transcription: initiation, elongation, or termination. In eukaryotic systems, initiation involves the association of the RNA polymerase with several other enzymes and factors at the promoter. For accurate initiation, a number of the specific initiation factors are required.

Elongation is the phase in which the RNA polymerase moves along the strand of DNA, extending the growing RNA chain as it does so. As the RNA polymerase moves it unwinds the DNA helix to expose a new segment of the template in single-stranded form. Nucleotides are then covalently added to the 3' end of the elongating RNA chain forming an RNA-DNA hybrid in the unwound region. The DNA strand then re-associates with its DNA complement, thereby reforming the double helix structure and displacing the single-stranded RNA strand. Thus, elongation involves the transient disruption of DNA structure to form an unwound region that exists as a hybrid RNA-DNA duplex and a displaced single strand of DNA.

Termination of transcription occurs when the RNA polymerase reaches a termination codon, i.e., a noncoding segment of the DNA template strand. At this point, no additional nucleotides are added to the RNA chain. The termination stage ends when the RNA polymerase, DNA template, and newly synthesized RNA chain dissociate into separate entities.

Messenger RNA (mRNA)transcription is a complex biochemical process requiring the action of multiple transcription factors. Transcription factors include both initiation and elongation factors, which control the activity of the RNA polymerase at the initiation and elongation stages of transcription, respectively. Several of these factors are known to be essential for initiation and are referred to as factors D, E, A, G, and B from *Saccharomyces cerevisiae*, τ, α, βγ, δ, and ε from rat liver, and TFIID, TFIIB, RAP30/74 or TFIIF, BTF2 or TFIIH, and TFIIE from human cells.

In addition to these factors, other proteins have been shown to stimulate either the initiation or elongation stages of transcription by RNA Polymerase II. One such factor, designated TFIIA, has been purified from both *Saccharomyces cerevisiae* and mammalian cells. TFIIA appears to promote assembly of the transcriptional pre-initiation complex. Although TFIIA is not essential for initiation, several lines of evidence suggest that it functions to increase the number of pre-initiation complexes that form at the promoter.

Considerable progress has recently been achieved identifying and characterizing transcriptional factors that support a basal level of transcription by RNA Polymerase II. Significantly less information, however, is available on transcription factors regulating the efficiency of transcriptional initiation or RNA chain elongation. Such transcriptional factors play an important role in regulating gene expression.

Currently, five general transcription elongation factors influencing RNA chain elongation have been identified and characterized with a high degree of certainty. These are SII, P-TEFb, TFIIF, ELL, and Elongin (also known as "SIII"). The general elongation factors TFIIF (RAP30/74) and ELL act to increase the overall rate of RNA chain elongation by suppressing transient pausing of the RNA polymerase at a variety of sites. The transcription factors SII and P-TEFb prevent RNA Polymerase II from arresting transcription prematurely. SII has been shown to promote RNA polymerase read-through at intrinsic pause sites in a human histone gene, the adenyl virus genome, and at several other sites. SII is a 38 kiloDalton (kD) elongation factor that promotes passage of RNA Polymerase II through transcriptional impediments such as nucleoprotein complexes and DNA sequences acting as intrinsic arrest sites. P-TEFb catalyzes the conversion of early, termination prone elongation complexes into productive elongation complexes.

A fifth elongation factor which increases the overall rate at which RNA Polymerase II transcribes DNA is Elongin. Elongin is a trimeric complex consisting of three protein subunits labeled Elongin A (110 kD as measured by SDS-PAGE), Elongin B (18 kD as measured by SDS-PAGE), and Elongin C (15 kD as measured by SDS-PAGE) having 773, 118 and 112 amino acid residues, respectively. Elongin A is capable of weakly stimulating transcriptional activity at a low level in the absence of Elongin B and/or C, while Elongins B and C serve regulatory functions which increase the transcriptional activation activity of Elongin A. Elongins B and C bind stably to each other in the absence of Elongin A to form a binary complex (Elongin BC) that interacts with Elongin A strongly inducing its transcriptional activity.

In addition, it has been shown that Elongin C can assemble with Elongin A in the absence of Elongin B to form an Elongin AC complex which increased specific activity, thereby increasing the rate of RNA chain elongation. Elongin B does not interact with Elongin A in the absence of Elongin C and apparently functions like a chaperone protein facilitating the assembly and enhancing the stability of the Elongin ABC complex. The identification, purification and characterization of Elongin and its subunits Elongins A, B and C have been described in U.S. Ser. No. 08/524,757 filed on Sep. 7, 1995, now U.S. Pat. No. 5792 634 and incorporated herein by reference.

Elongin has also been reported to interact with the product ("pVHL") of the Von Hippel-Lindau tumor suppressor gene. The Von Hippel-Lindau tumor suppressor gene, which predisposes individuals to various tumor types, translates into a 213 amino acid protein capable of binding to and inhibiting the activity of Elongin. In particular, it has been reported that wild-type pVHL binds tightly and specifically to the Elongin BC complex and prevents it from activating Elongin A. That is, binding of the PVHL protein and Elongin A to the Elongin BC complex are mutually exclusive in vitro.

The previous work on Elongin described above provided a useful product for regulating the transcriptional activity of RNA Polymerase II. There still remained, however, a need to identify the functional domains of the Elongin subunits. As described herein, the Elongin A transcriptional activation domain has now been identified. This domain has been found to define a new evolutionarily conserved class of inducible activation domain. It has also been shown that the transcriptional activation domain of Elongin A and the Von Hippel-Lindau tumor suppressor protein (pVHL) interact with the Elongin BC complex through a conserved Elongin BC binding site motif essential for induction of Elongin A activity by Elongin BC and for tumor suppression by the VHL protein. In addition, the regions of Elongin C important for binding to Elongin B and for binding to and activating Elongin A have also been identified.

The identification and characterization of these domains serves two purposes. First, Elongin subunits or fragments thereof having at least the functional domains described herein can be used in place of the entire subunits in in vitro transcriptional assays or systems. Secondly, and perhaps more importantly, these regions can be used as laboratory reagents for work concerning the transcriptional activation activities of Elongin.

SUMMARY OF THE INVENTION

The present invention relates to the domains of Elongin A having transcriptional activation activity and Elongin BC binding activity. In another aspect, the present invention relates to an analog of the human Elongin A.

In another aspect, the present invention relates to the domains of Elongin C having Elongin activation activity and Elongin A and/or Elongin B binding activity.

In still another aspect, the present invention relates to the nucleotide sequences encoding the various Elongin subunits and their functional domains.

BRIEF DESCRIPTION OF THE DRAWINGS

FIG. 7. Comparison of the amino acid sequences of rat and C. elegans Elongin A (SEQ ID NO:79 and amino acids 1–423 of SEQ ID NO:42, respectively). Identical amino acids are boxed with broken lines; chemically similar amino acids are bolded. The Elongin BC binding site motif is boxed with solid lines, and the region most highly conserved between rat and C. elegans Elongin A is underlined.

FIG. 9A. Histidine-tagged Elongin C deletion mutants analyzed in this study Elongin C (SEQ ID NO:9); C(15–112) (SEQ ID NO:46); C(19–112) (SEQ ID NO:47); C(23–112) (SEQ ID NO:48); C(29–112) (SEQ ID NO:49); C(57–112) (SEQ ID NO:50); C(1–97) (SEQ ID NO:51); C(1–83) (SEQ ID NO:52); C(Δ21–30) (SEQ ID NO:53); C(Δ31–40) (SEQ ID NO:54); C(Δ41–50) (SEQ ID NO:55); C(Δ51–60) (SEQ ID NO:56); C(Δ61–70) (SEQ ID NO:57); C(Δ71–80) (SEQ ID NO:58); C(Δ81–90) (SEQ ID NO:59); C(Δ91–100) (SEQ ID NO:60); C(Ala 19–21) (SEQ ID NO:61); C(Ala 22–24) (SEQ ID NO:62); C(Ala 25–27) (SEQ ID NO:63); C(Ala 28–30) (SEQ ID NO:64); C(Ala 89–91) (SEQ ID NO:65); C(Ala 92–94) (SEQ ID NO:66); C(Ala 95–97) (SEQ ID NO:67); C(Ala 98–100) (SEQ ID NO:68); C(Ala 101–103) (SEQ ID NO:69); C(Ala 104–106) (SEQ ID NO:70); C(Ala 107–109) (SEQ ID NO:71); and C(Ala 110–112) (SEQ ID NO:72).

FIG. 9B. Elongin C alanine scanning mutants analyzed in this study.

FIG. 10C. Elongin C alanine scanning mutants were assayed for their abilities to form Elongin BC complexes as described. C(Ala19–21) (SEQ ID NO:61) co-electrophoreses with wild type Elongin B during SDS-PAGE. B, Elongin B; C, wild type or mutant Elongin C; L, load; FT, flow-through.

FIG. 11A. Assay of activation of Elongin A by wild type and mutant Elongin BC complexes wherein runoff transcription assays were performed as described according the protocol diagramed at the bottom of the figure. A mixture containing ~50 ng of SP-NPR purified Elongin A and ~5 ng (1×BC) or ~50 ng (10×BC) of purified wild type or mutant Elongin BC was preincubated on ice for 60 min prior to addition to reaction mixtures. Purified Elongin BC complexes were from the following DEAE-NPR fractions shown in FIG. 10B: Wild type (SEQ ID NO:9), fraction 7; BC(15–112) (SEQ ID NO:46), fraction 5; BC(19–112) (SEQ ID NO:47), fraction 5; BC(1–97) (SEQ ID NO:51), fraction 6; and BC(1–83) (SEQ ID NO:52), fraction 5. Reactions shown in lanes 1 and 7 contained no Elongin BC. WT, wild type.

DETAILED DESCRIPTION

Figure 1A:
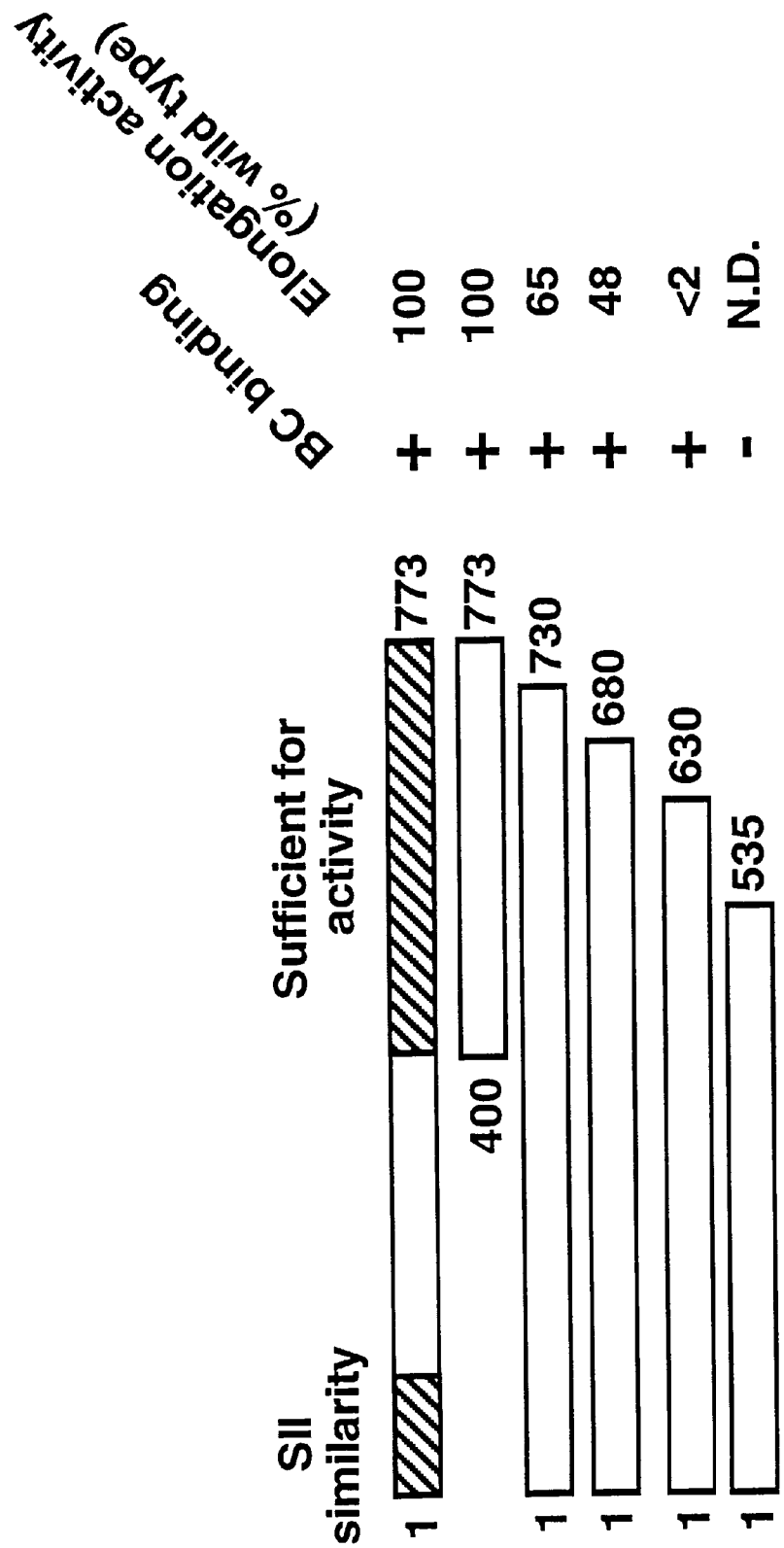
FIG. 1A. N- and C-terminal Elongin A deletion mutants analyzed in this study. At right, the results of assays described in the text and shown in panels 1C and 1D are summarized. N. D., not determined.

The present invention relates to the Elongin A domains required for transcriptional elongation activation and for binding to Elongin BC and of the Elongin C domains required for interaction with Elongin B and activation of Elongin A's transcriptional elongation activity and the use of these domains.

Elongin A

Wild-type Elongin A is a 773 amino acid protein (SEQ ID NO:1) which stimulates the elongation activity of RNA Polymerase II. Fragments of the wild-type Elongin A having amino acid residues 1 to 730 (SEQ ID NO:2), 1 to 680 (SEQ ID NO:3), and 400–773 (SEQ ID NO:4) each possess about 50% or more of the elongation activation activity exhibited by wild-type Elongin A. From the results it can be predicted that fragments of the wild-type Elongin A having amino acid residues 400–730 (SEQ ID NO:5) and 400–680 (SEQ ID NO:6) will also possess about 50% or more of the elongation activity exhibited by wild-type Elongin A.

The Elongin A sequence critical for binding to Elongins B and C also falls within this 374 amino acid sequence, i.e., between residues 400 and 773 (SEQ ID NO:4). This sequence, i.e., the Elongin B and C binding region of Elongin A, falls within a 20 amino acid region between residues 546 and 565 (SEQ ID NO:7) and preferably within a 12 amino acid region between residues 549 and 560 (SEQ ID NO:8).

Thus, the Elongin A region encompassing amino acid residues 400–773 (SEQ ID NO:4) includes all of the sequences necessary for full Elongin A transcriptional elongation activity and for regulation by Elongin BC. An Elongin A protein or fragment thereof containing this entire wild-type 374 amino acid region or a substantial portion of it will exhibit significant elongation activation activity and can be used in a variety of in vitro transcription systems or assays by one of ordinary skill in the art.

Elongin C

Wild-type Elongin C is a 112 amino acid protein (SEQ ID NO:9) which induces the transcriptional activity of Elongin A. The regions of the wild-type Elongin C required for (1) binding to Elongin B, (2) binding to Elongin A, and (3) activation of Elongin A transcriptional activity have now been localized. These regions are the amino acids between (1) residues 19 and 30 (SEQ ID NO:10), (2) residues 19 and 30 (SEQ ID NO:10) and 100 and 112 (SEQ ID NO:11), and (3) residues 19 and 30 (SEQ ID NO:10), 60 and 71 (SEQ ID NO:12)and 91–112 (SEQ ID NO:13), respectively.

Thus, an Elongin C protein or fragment thereof containing these wild-type regions will possess all sequences necessary for interaction and binding with Elongins A and B and can be used in a variety of in vitro transcription systems or assays by one of ordinary skill in the art.

Construction of the Elongin A and C subunits as well as N- and C- terminal and internal deletion mutants thereof was done as described in Examples 2 and 13. Expression and purification of these subunits was done as described in Examples 2, 3 and 14.

Identification and Characterization of the Elongin A Domains Required for Transcriptional Activation and Binding to Elongin BC Elongin A is a 773 amino acid protein (SEQ ID NO:1) with a calculated molecular mass of 87.2 kDa as calculated from the amino acid sequence predicted from the cDNA. It has now been determined that an Elongin A region encompassing amino acids 400–773 (SEQ ID NO:4) includes all sequences necessary for full Elongin A transcriptional activity and for regulation by Elongin BC. The most critical sequences within the Elongin A transcriptional activation domain (residues 400–773) (SEQ ID NO:4) have been localized to an ~171 amino acid region between residues 520 and 690 (SEQ ID NO:14). Sequences outside this region, though not essential for activation of transcription, either participate in interactions with the RNA Polymerase II elongation complex or help to maintain the structural integrity of the transcriptional activation domain. Finally, the transcriptional activation domain of Elongin A has been found to be evolutionarily conserved in species as distantly related as C. elongans (nematode) and man.

It has also been determined that the Elongin A sequence critical for binding to Elongin B and C fall within a 19 amino acid region between residues 546 and 565 (SEQ ID NO:7) and preferably within a 12 amino acid region between residues 549 and 560 (SEQ ID NO:8). This region shares a sequence similarity with a short region of the VHL protein (residues 157–172) (SEQ ID NO:15) previously shown to be sufficient for binding to Elongin B and C (Kibel, et al. *Science* 269: 1444–1446 (1995). Within this conserved Elongin BC binding site motif (consensus sequence TLx3Cx2V[V,2]) SEQ ID NO:16 identical threonine, leucine, cysteine and valine are found in Elongin A and VHL at the positions designated 1, 2, 6 and 9, respectively in SEQ ID NO:8 for Elongin A and in SEQ ID NO:15 for VHL protein.

Localization of the Elongin A Transcriptional Activation Domain

The Elongin A transcriptional activation domain was located and the Elongin BC binding site was identified using a series of N- and C-terminal Elongin A deletion mutants (FIG. 1A). These Elongin A deletion mutants were constructed, expressed in *E. coli*, purified, and assayed for their abilities (i) to assemble into chromatographically isolable Elongin ABC complexes and (ii) to stimulate the rate of elongation of transcripts synthesized by RNA Polymerase II from the AdML promoter in a reconstituted basal transcription system composed of TBP and the general initiation factors TFIIB, TFIIE, TFIIF, and TFIIH.

Figure 1B:
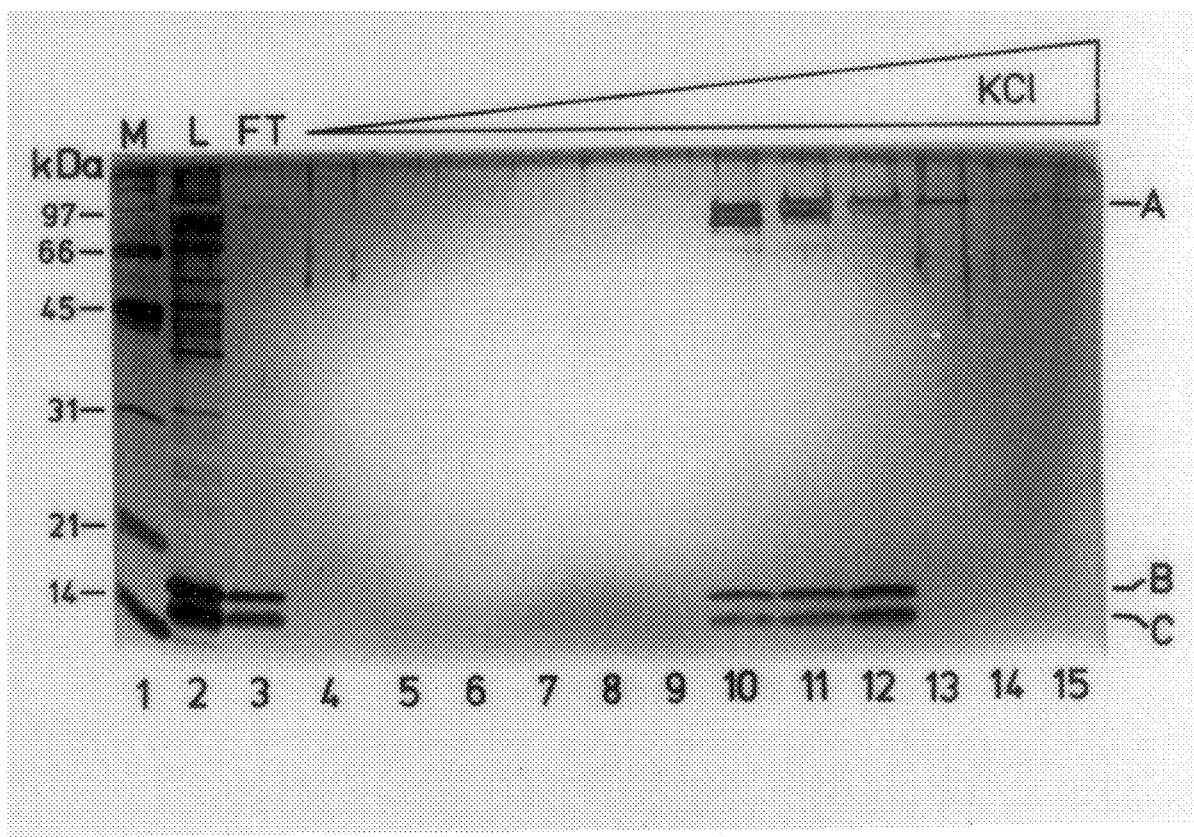
FIG. 1B. Wild type Elongin A was refolded together with wild type Elongin B and C and subjected to TSK SP-NPR HPLC as described. Aliquots of column fractions were analyzed by SDS-PAGE, and proteins were visualized by silver staining. M, molecular weight markers; L, load; FT, flow through; kDa, kilodaltons; A, Elongin A; B, Elongin B; C, Elongin C.
Figure 1C:
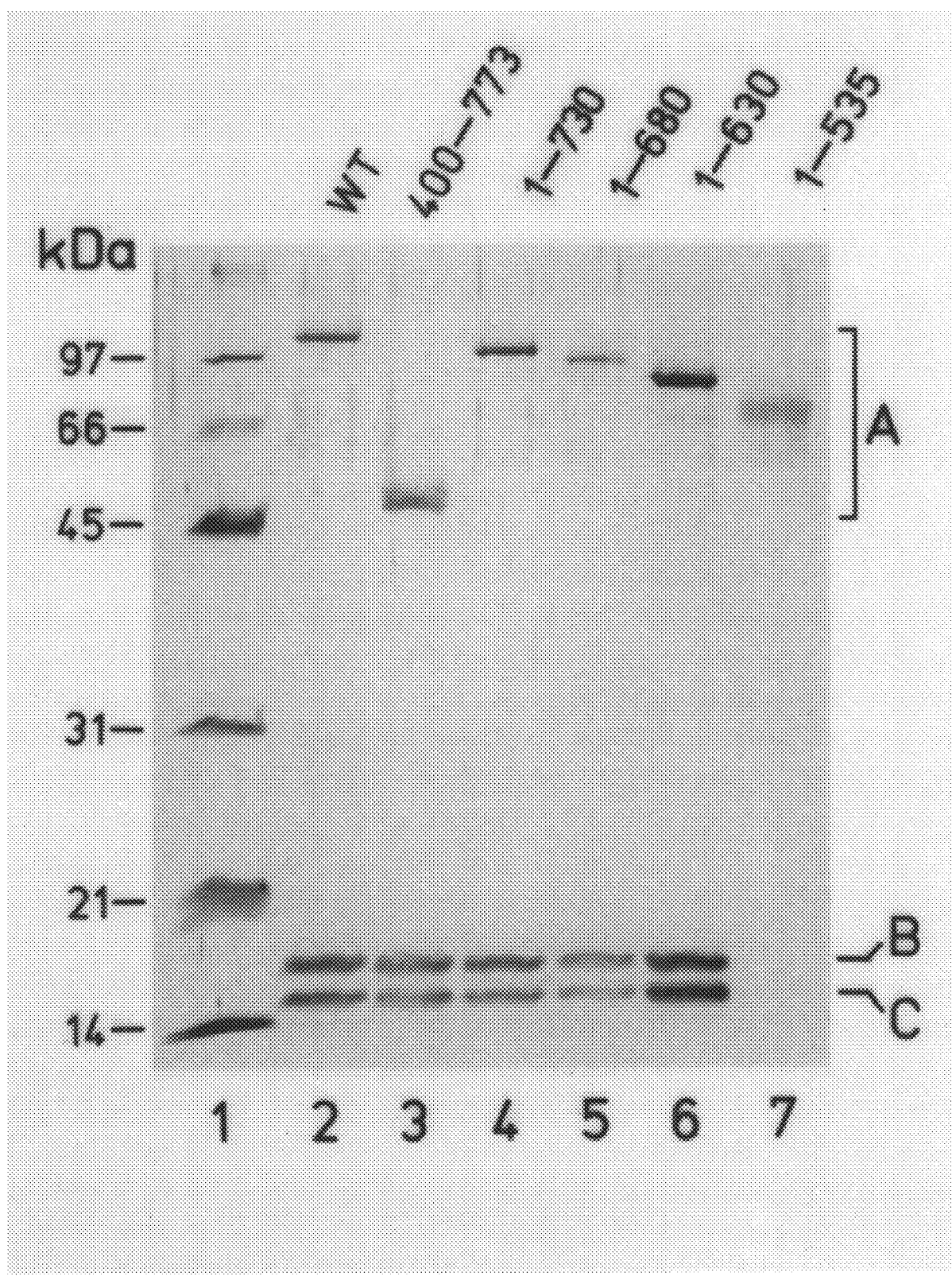
FIG. 1C. N- and C-terminal Elongin A deletion mutants were refolded together with wild type Elongin B and C and subjected to TSK SP-NPR HPLC as described. Aliquots containing ~100 ng of the peak column fractions were analyzed by SDS-PAGE, and proteins were visualized by silver staining. In this and subsequent figures, WT designates wild type Elongin A.

To test the abilities of Elongin A mutants to bind Elongin B and C and to isolate mutant Elongin ABC complexes for assay of their relative transcriptional activities, N- and C-terminal Elongin A deletion mutants were refolded together with wild type Elongin B and C and subjected to TSK SP-NPR HPLC. Both wild type and mutant Elongin ABC complexes bind tightly to TSK SP-NPR and elute at salt concentrations between 0.2 and 0.4M KCl, whereas excess Elongin B and C flow through this resin at 0.1M KCl (Aso, et al., *Science* 269: 1439–1443 (1995)). FIG. 1B shows SDS-PAGE analysis of aliquots of column fractions from TSK SP-NPR HPLC purification of wild type Elongin ABC complexes. FIG. 1C shows SDS-PAGE analysis of aliquots of peak column fractions from TSK SP-NPR HPLC purification of mutant Elongin ABC complexes: wild type (WT) (SEQ ID NO:1); 400–773 (SEQ ID NO:4); 1–730 (SEQ ID NO:2); 1–680 (SEQ ID NO:3); 1–630 (SEQ ID NO:17); and 1–535 (SEQ ID NO:18). Results of this analysis revealed that all N- and C-terminal Elongin A deletion mutants except A(1–535) (SEQ ID NO:18), which lacks the region similar to the Elongin BC binding site in the VHL protein (Kibel, et al., *Science* 269: 1444–1446 (1995), were able to bind stably to Elongin B and C to form isolable Elongin ABC complexes.

Figures 1D, 1E:
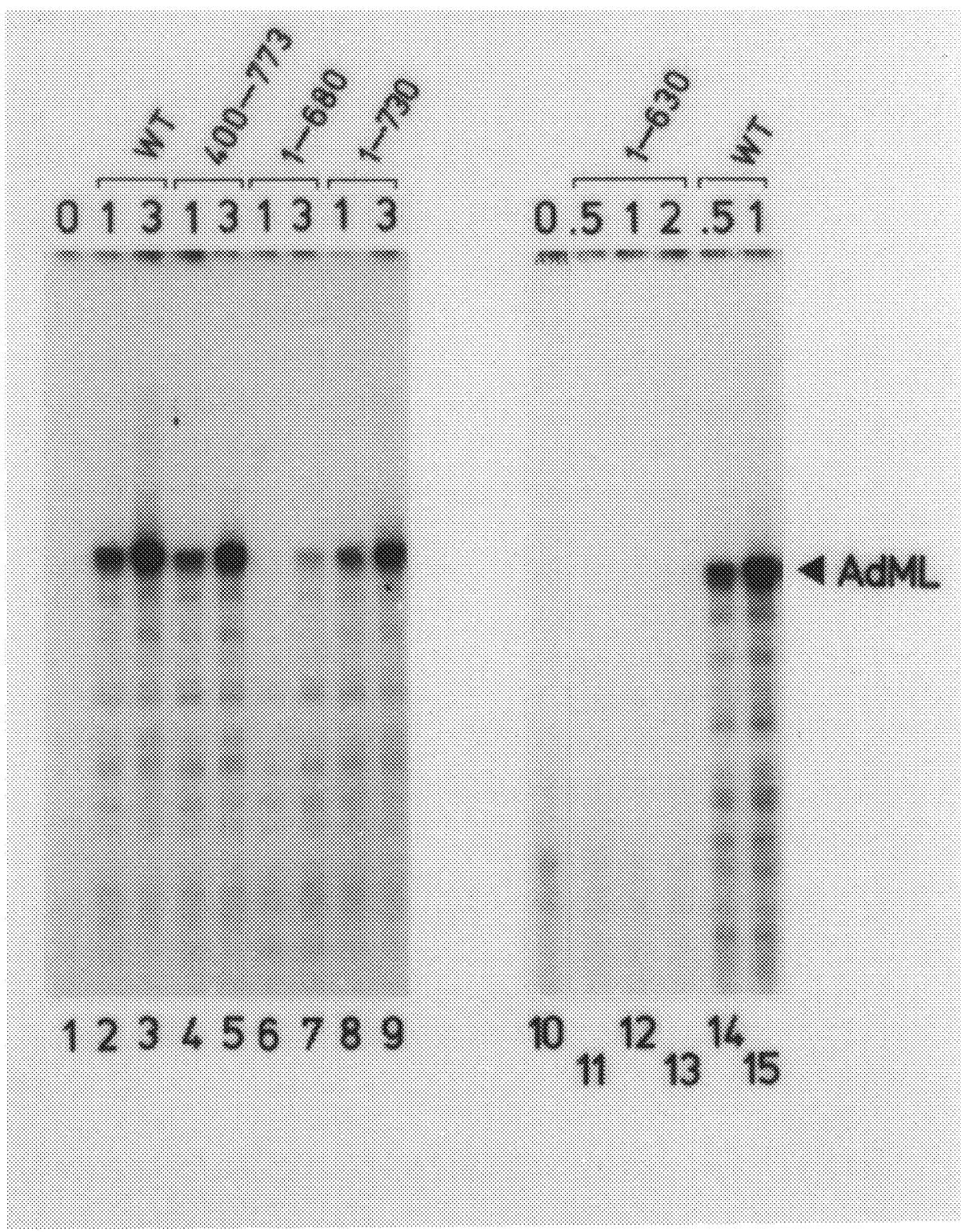
FIG. 1D. Runoff transcription assays were performed as described. The reaction mixture in lane 1 contained no Elongin. Elongin complexes were present in reaction mixtures at the indicated relative molar concentrations; a relative molar concentration of 1 is equivalent to ~2 nM Elongin A. In this and subsequent figures, AdML indicates the position of the full-length ~250 nucleotide runoff transcript synthesized by RNA Polymerase II from the AdML promoter.
FIG. 1E. Runoff transcription assays were performed as described. The reaction mixture in lane 10 contained no Elongin. Elongin complexes were present in reaction mixtures at the indicated relative molar concentrations; a relative molar concentration of 1 is equivalent to ~2 nM Elongin A.

The relative transcriptional activation activities of the wild type and mutant Elongin ABC complexes shown in FIG. 1C were then compared in runoff transcription assays. Preinitiation complexes were assembled at the AdML promoter, wild type and mutant Elongin ABC complexes were added to reaction mixtures, and transcription was initiated by addition of limiting concentrations of ribonucleoside triphosphates. Under these conditions, the rate of RNA chain elongation is very slow, and runoff transcripts do not accumulate unless elongation stimulatory activity is present. Bradsher, et al., *J Biol Chem* 268: 25594–25603 (1993); Aso, et al., *Science* 269: 1439–1443 (1995). FIG. 1D, lanes 1 and 2.

Results of these experiments indicated that the first 400 Elongin A amino acids (SEQ ID NO:19) (which include a region of SII similarity and a potential ATP binding site), are dispensable for Elongin ABC activity in vitro, since deletion of this region had no significant effect on accumulation of runoff transcripts. In contrast, deletion of the C terminal 93 amino acids (SEQ ID NO:3), which includes a potential hydrophobic zipper, decreased Elongin ABC activity by approximately 50%, and deletion of the C-terminal 143 amino acids (SEQ ID NO:17) abolished detectable Elongin ABC activity. Taken together, these results identified (i) a 20 amino acid Elongin A region (residues 546 to 565) (SEQ ID NO:7), which includes sequences required for interaction with Elongin B and C, (ii) a 281 amino acid Elongin A region (residues 400 to 680) (SEQ ID NO:6), which includes sequences required for transcriptional activity, and (iii) an additional C-terminal Elongin A region (residues 680 to 773) (SEQ ID NO:20), which includes sequences important for maximal transcriptional activity.

The Elongin A sequences required for binding to Elongin B and C and for transcriptional activity were further defined using a series of Elongin A internal deletion mutants. These mutants (FIG. 2A), with mutations spanning the transcriptional activation domain from residues 400 to 730 (SEQ ID NO:5) were constructed, expressed in *E. coli*, purified, and assayed as described above. The mutant sequences tested were: Δ401–440 (SEQ ID NO:21); Δ441–480 (SEQ ID NO:22); Δ481–520 (SEQ ID NO:23); Δ521–545 (SEQ ID NO:24); Δ546–565 (SEQ ID NO:25); Δ566–585 (SEQ ID NO:26); Δ586–610 (SEQ ID NO:27); Δ611 . 650 (SEQ ID NO:28); Δ651–690 (SEQ ID NO:29); and Δ691–730 (SEQ ID NO:30).

Figure 2A:
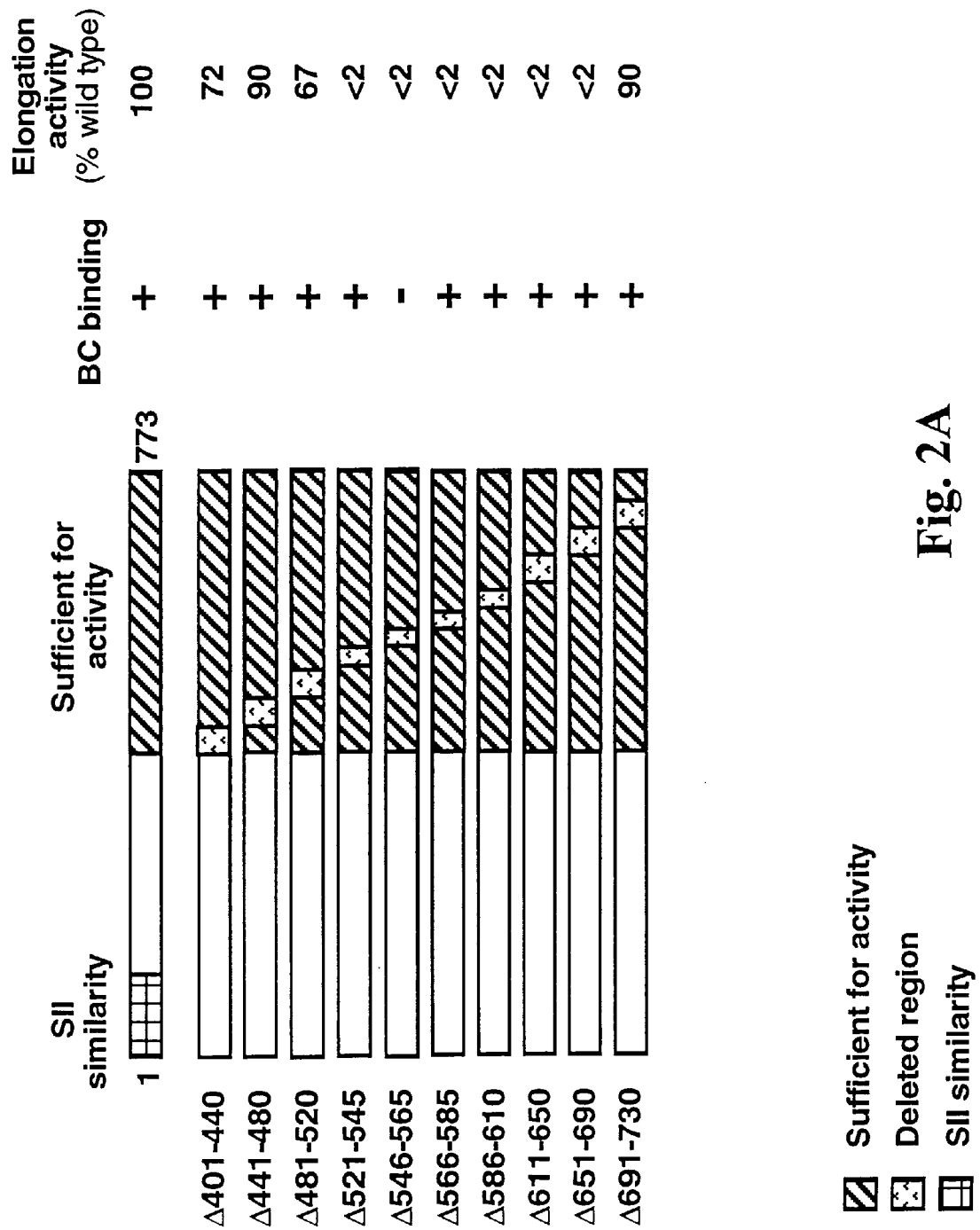
FIG. 2A. Analysis of Elongin A internal deletion mutants. At right, the results of assays described in the text and shown in panels 2B and 2C are summarized.
Figure 2B:
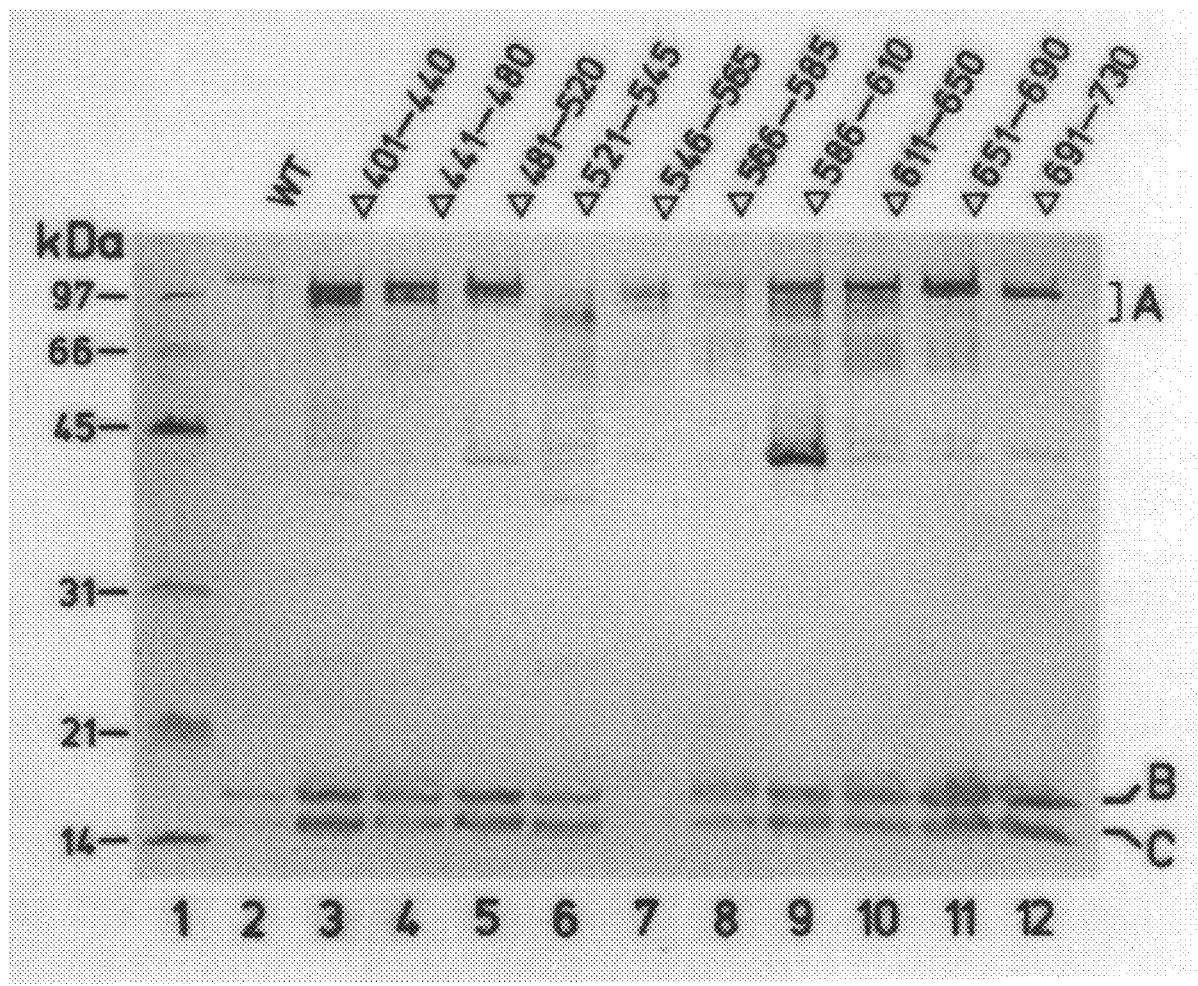
FIG. 2B. Elongin A internal deletion mutants were refolded together with wild type Elongin B and C and subjected to TSK SP-NPR HPLC as described. Aliquots containing ~100 ng of the peak column fractions were analyzed by SDS-PAGE, and proteins were visualized by silver staining.
Figures 2C, 2D:
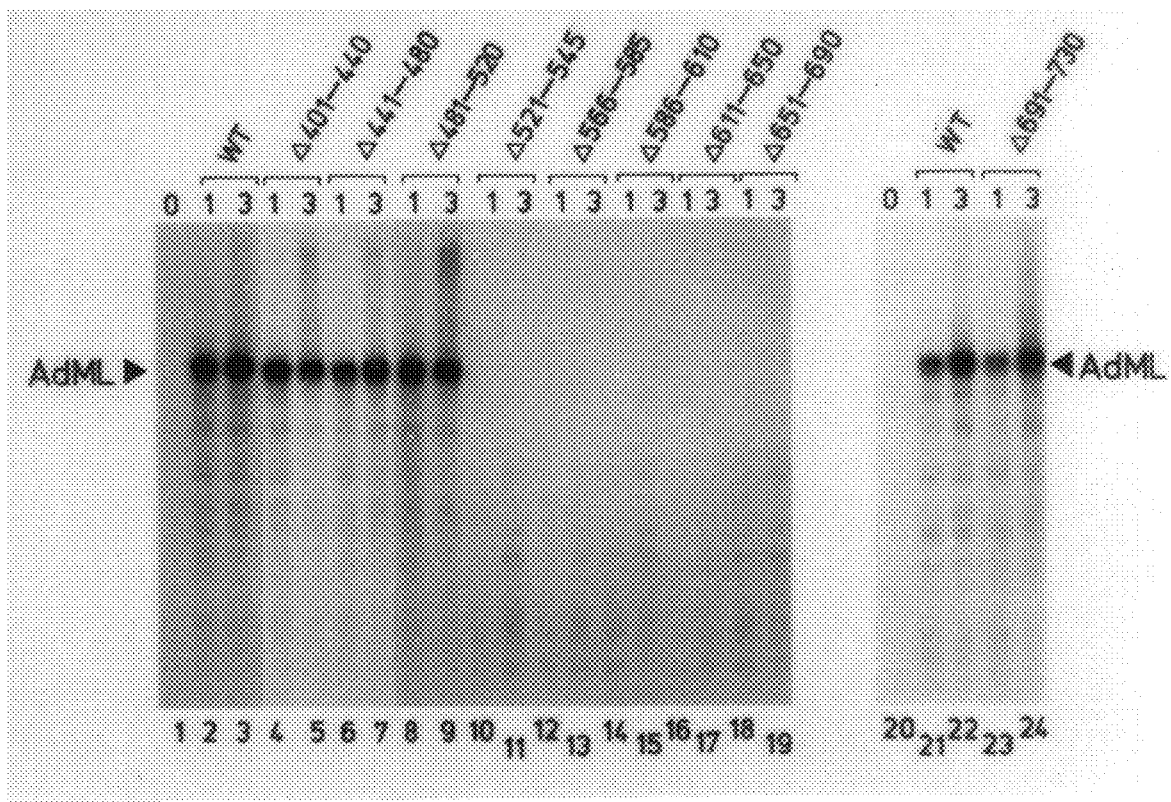
FIG. 2C. Runoff transcription assays were performed as described. Elongin complexes were present in reaction mixtures at the indicated relative molar concentrations; a relative molar concentration of 1 is equivalent to ~2 nM Elongin A.
FIG. 2D. Runoff transcription assays were performed as described. Elongin complexes were present in reaction mixtures at the indicated relative molar concentrations; a relative molar concentration of 1 is equivalent to ~2 nM Elongin A.

All Elongin A internal deletion mutants, except Δ546–565 (SEQ ID NO:25), which lacks the region similar to the Elongin BC binding site found in the VHL protein (Kibel, et al., *Science* 269: 1444–1446 (1995)), were capable of binding to Elongin B and C (FIGS. 2A and 2B). As shown in FIG. 2C and 2D, Elongin ABC complexes containing Elongin A internal deletion mutants Δ401–440 (SEQ ID NO:21), Δ441–480 (SEQ ID NO:22), Δ481–520 (SEQ ID NO:23), and Δ691–730 (SEQ ID NO:30) exhibited significant transcriptional activity. In contrast, Elongin ABC complexes containing Elongin A internal deletion mutants lacking sequences located in the region between amino acids 520 and 691 were profoundly impaired in their abilities to stimulate elongation by RNA Polymerase II.

Figures 3A, 3B:
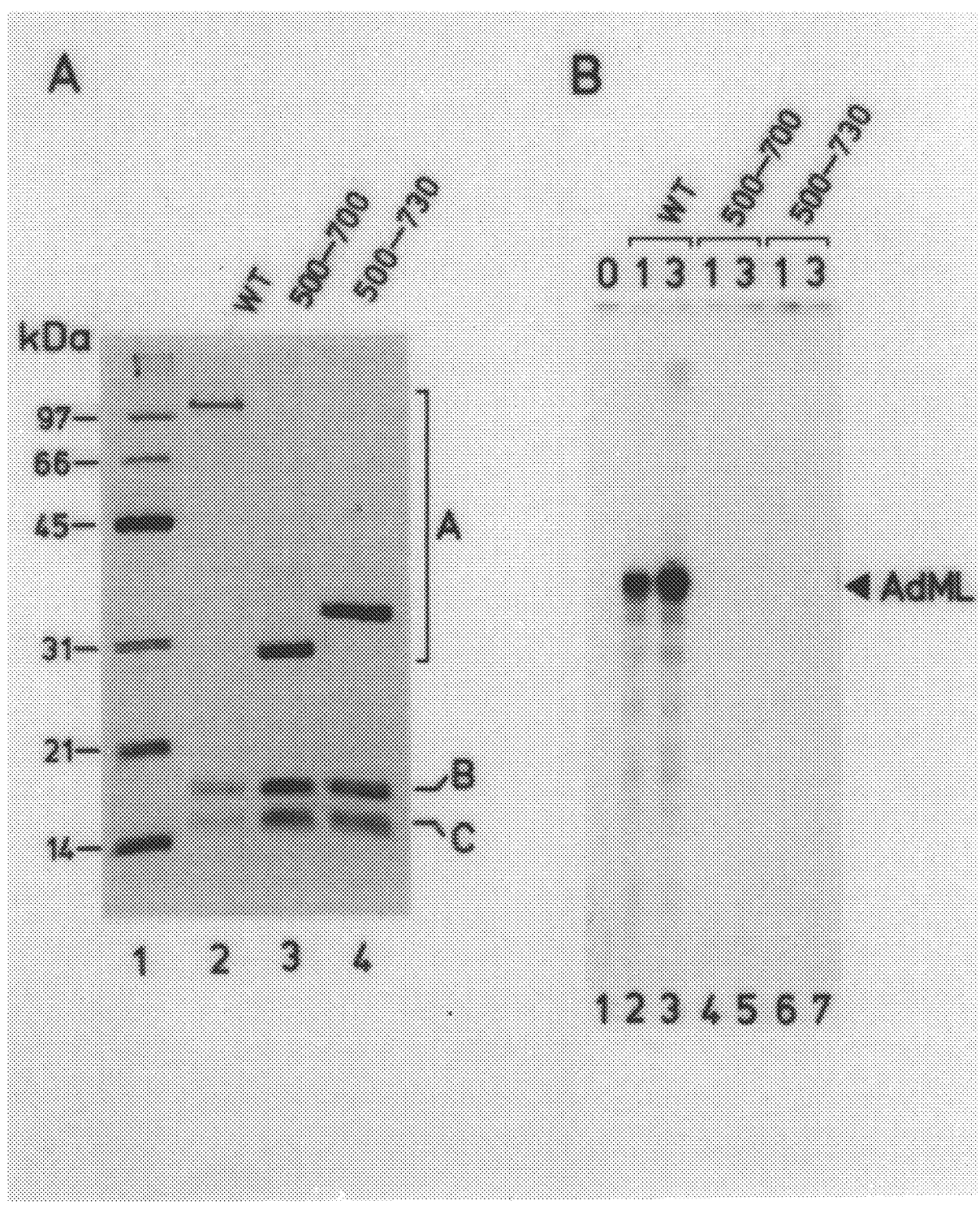
FIG. 3A. Analysis of short Elongin deletion mutants containing the minimal transcriptional activation domain. Elongin A deletion mutants were refolded together with wild type Elongin B and C and subjected to TSK SP-NPR HPLC as described. Aliquots containing ~100 ng of the peak column fractions were analyzed by SDS-PAGE, and proteins were visualized by silver staining.
FIG. 3B. Runoff transcription assays were performed as described. The reaction mixture in lane 1 contained no Elongin. Elongin complexes were present in reaction mixtures at the indicated relative molar concentrations; a relative molar concentration of 1 is equivalent to ~2 nM.

Notably, the Elongin ABC complex containing Elongin A internal deletion mutant Δ521–545 (SEQ ID NO:24), which lacks a potential topoisomerase I catalytic site motif, is inactive in activating transcription. Topoisomerase I activity is unlikely to play a role in Elongin (SIII) function in vitro, however, because (i) we observed that mutating the potential active site tyrosine at residue 543 to either phenylalanine or serine had no effect on Elongin A transcriptional activation activity (data not shown) and (ii) we have been unable to detect topoisomerase I activity associated with Elongin A Taken together, analysis of the N-terminal, C-terminal, and internal Elongin A deletion mutants localized sequences critical for transcriptional activity to a minimal region of ~170 amino acids between residues 521 and 690 (SEQ ID NO:31). Further investigation revealed, however, that Elongin A sequences outside this minimal region also make significant contributions to the transcriptional activation activity of Elongin A. For example, Elongin A mutants composed of residues 500 to 730 (SEQ ID NO:32) or residues 500 to 700 (SEQ ID NO:33) were transcriptionally inactive, even though they assembled into isolable Elongin ABC complexes (FIG. 3A and 3B). Thus, Elongin A sequences outside the minimal transcriptional activation domain make secondary contributions to Elongin activity, either by participating directly in interactions with the RNA Polymerase II elongation complex or by helping to maintain the proper three dimensional structure of the transcriptional activation domain.

Identification of the Elongin BC Binding Site

Figure 4A:
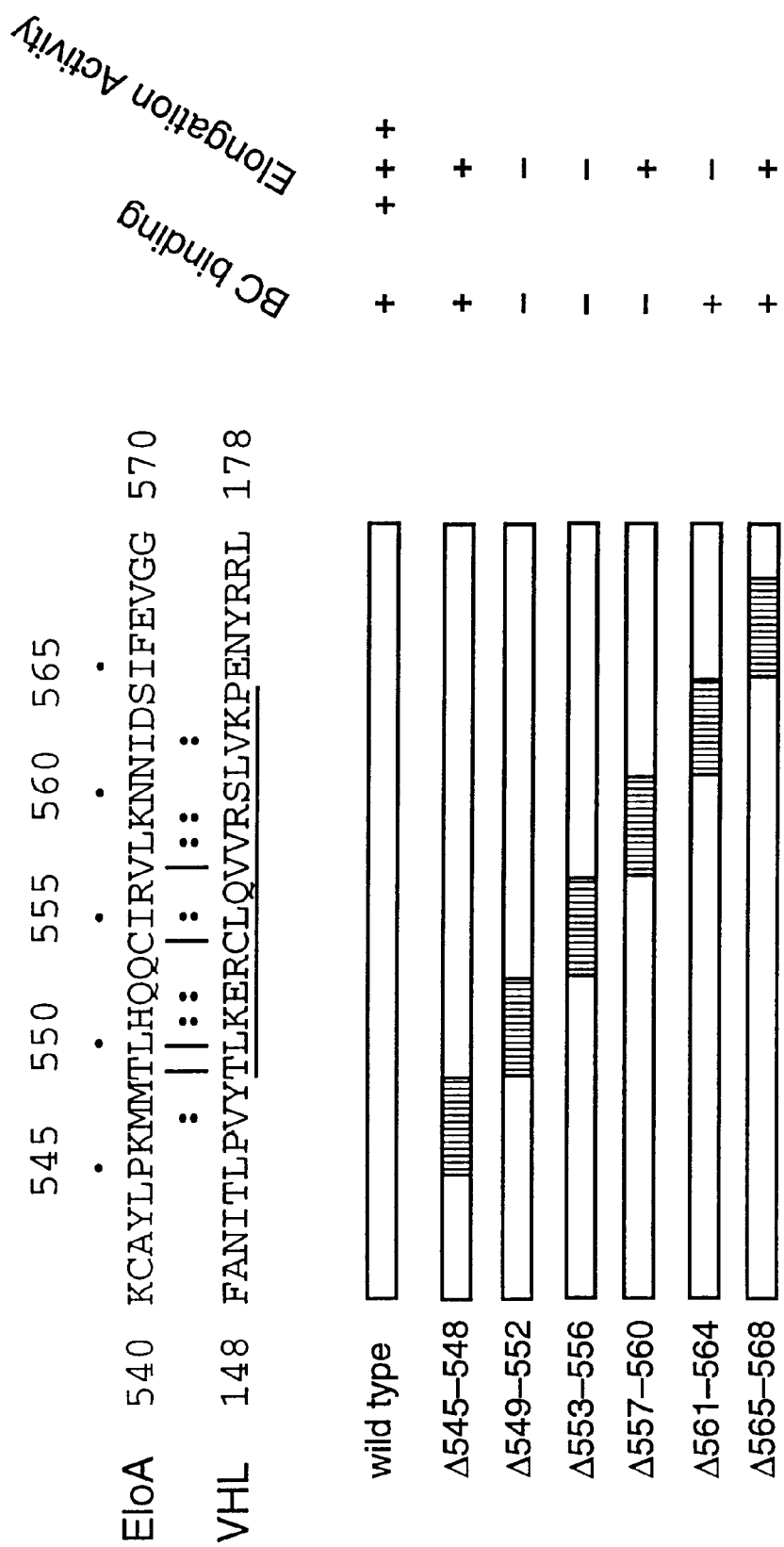
FIG. 4A. Analysis of Elongin A internal deletion mutants with mutations in the potential Elongin BC binding site. At the top is shown a comparison of the similar regions of Elongin A (amino acids 540–570 of SEQ ID NO:1) and the VHL protein (SEQ ID NO:78. The portion of the VHL protein shown to be sufficient for binding to Elongin B and C (Kibel, et al. *Science* 269: 1444–1446 (1995)) is underlined; vertical lines indicate identical amino acids; colons indicate chemically similar amino acids. EloA, Elongin A; VHL, VHL protein.

Analysis of Elongin A deletion mutants revealed that the Elongin A region between residues 546 and 565 (SEQ ID NO:7) plays an important role in binding to Elongin B and C. As shown in FIG. 4A, this Elongin A region shares sequence similarity with a short region of the VHL protein (residues 157–172, underlined) (SEQ ID NO:15) previously shown to be sufficient for binding to Elongin B and C (Kibel, et al., Science 269: 1444–1446 (1995)). This Elongin A region was further defined using a systematic series of Elongin A internal deletion mutants spanning residues 545 to 568 (SEQ ID NO:34). These mutants (FIG. 4A) were constructed, expressed in E. coli, purified, and assayed for their abilities to assemble into chromatographically isolable Elongin ABC complexes and to stimulate the rate of elongation by RNA Polymerase II. The mutants tested were: Δ545–548 (SEQ ID NO:35); Δ549–552 (SEQ ID NO:36); Δ553–556 (SEQ ID NO:37); Δ557–560 (SEQ ID NO:38); Δ561–564 (SEQ ID NO:39); and Δ565–568 (SEQ ID NO:40).

Figures 4B, 4C:
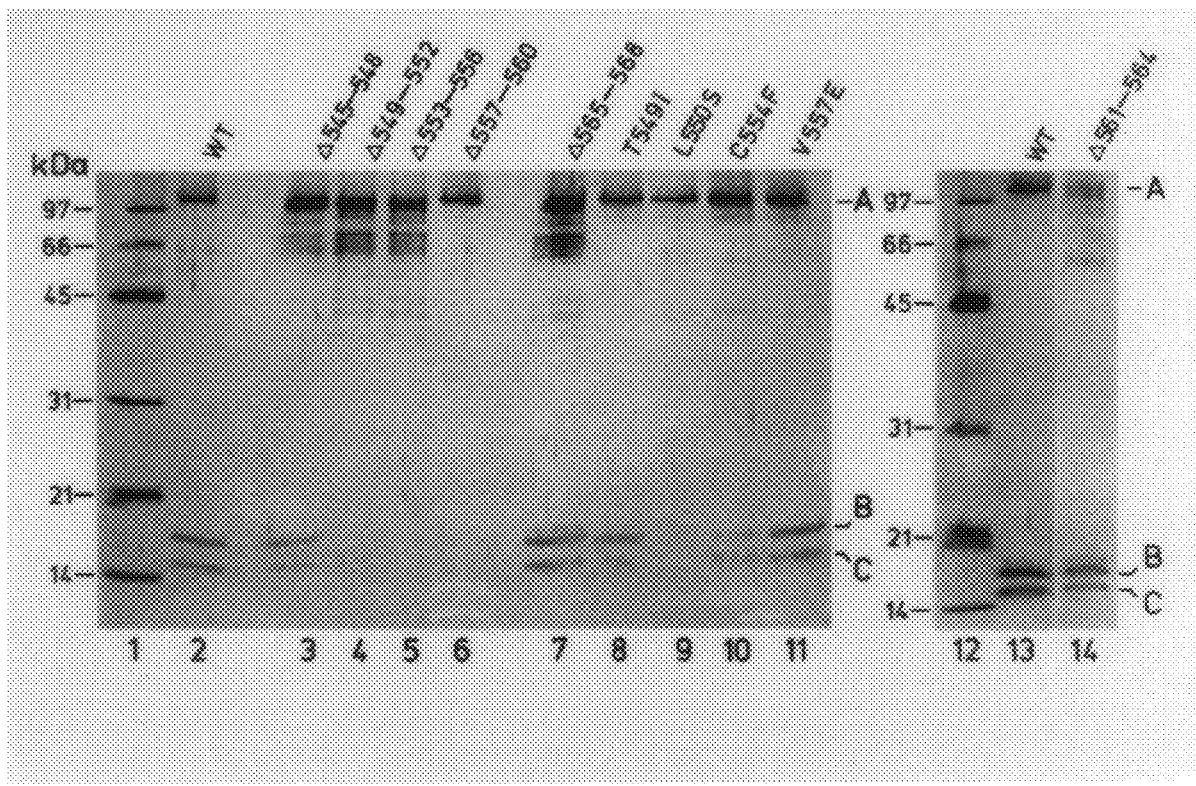
FIG. 4B. Elongin A internal deletion mutants were refolded together with wild type Elongin B and C and subjected to TSK SP-NPR HPLC as described. Aliquots containing ~100 ng of the peak column fractions were analyzed by SDS-PAGE, and proteins were visualized by silver staining.
FIG. 4C. Elongin A internal deletion mutant Δ561–564 was refolded together with wild type Elongin B and C and subjected to TSK SP-NPR HPLC as described. Aliquots containing ~100 ng of the peak column fractions were analyzed by SDS-PAGE, and proteins were visualized by silver staining.

As shown in FIG. 4B and 4C, Elongin A internal deletion mutants Δ545–548 (SEQ ID NO:35), Δ561Δ564 (SEQ ID NO:39), and Δ565–568 (SEQ ID NO:40) bound stably to Elongin B and C to form Elongin ABC complexes that could be purified by TSK SP-NPR HPLC. In contrast, Elongin A internal deletion mutants Δ549–552 (SEQ ID NO:36), Δ553–556 (SEQ ID NO:37), and Δ557–560 (SEQ ID NO:38), each of which lack Elongin A sequences within the region most similar to the Elongin BC binding site of the VHL protein, were impaired in their abilities to bind to Elongin B and C.

Figures 5A, 5B:
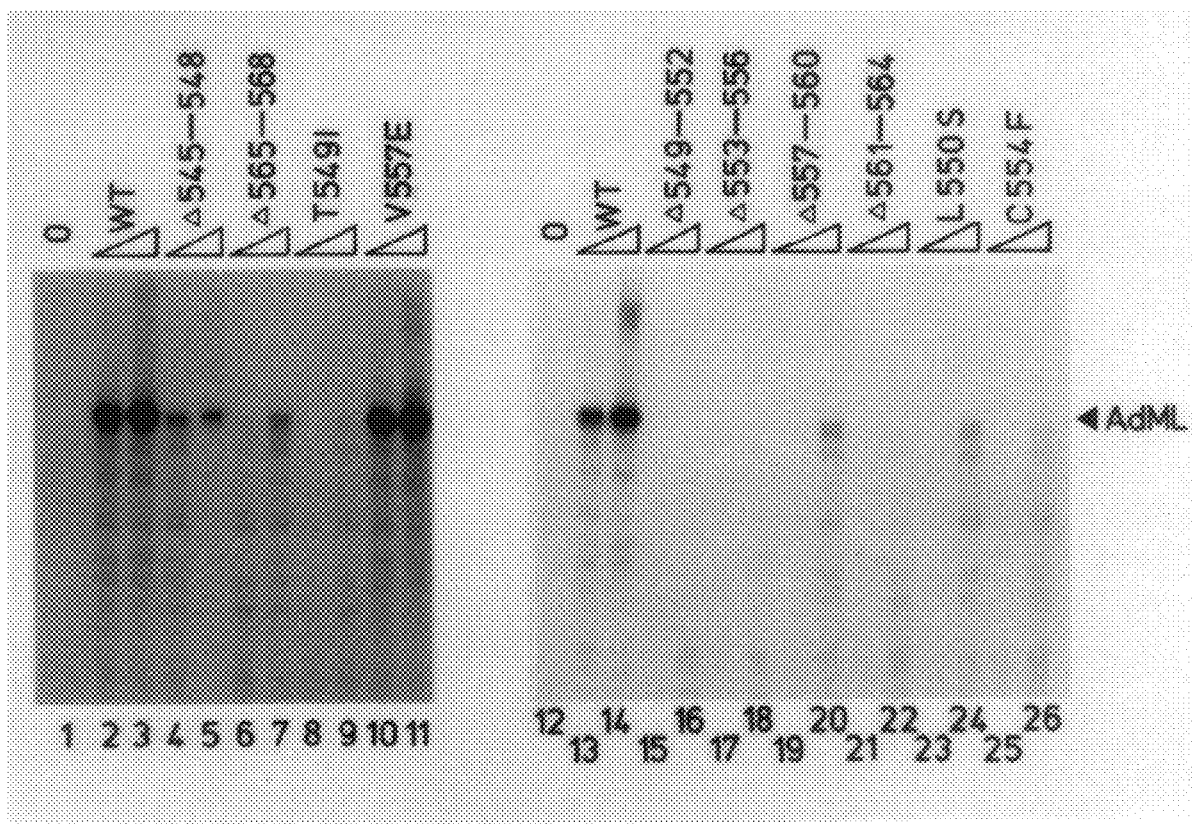
FIG. 5A. Transcription activity of Elongin A internal deletion and point mutants with mutations in the potential Elongin BC binding site. Runoff transcription assays were performed as described. Elongin complexes were present in reaction mixtures at the indicated relative molar concentrations; a relative molar concentration of 1 is equivalent to ~2 nM Elongin A.
FIG. 5B. Transcription activity of Elongin A internal deletion and point mutants with mutations in the potential Elongin BC binding site. Runoff transcription assays were performed as described. Elongin complexes were present in reaction mixtures at the indicated relative molar concentrations; a relative molar concentration of 1 is equivalent to ~2 nM Elongin A.
Figure 5C:
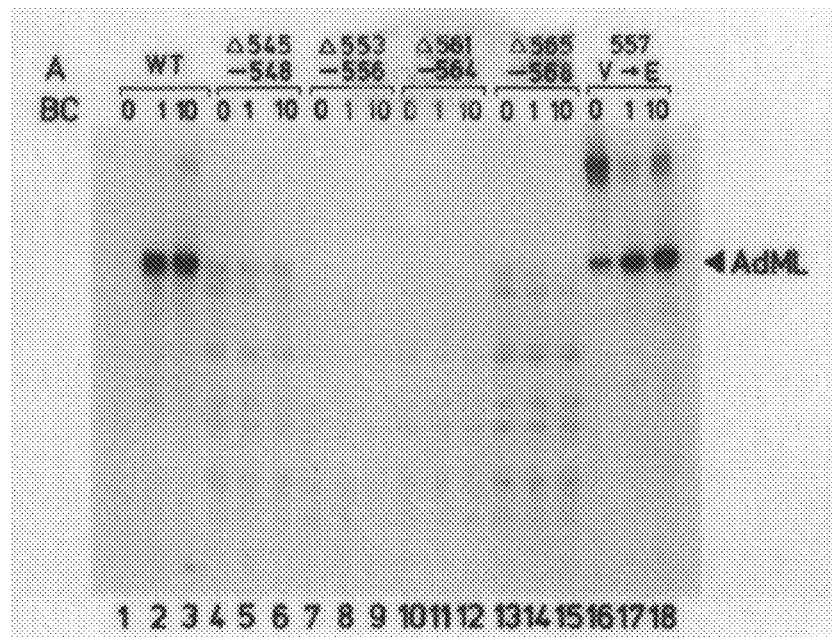
FIG. 5C. Runoff transcription assays were performed as described in the absence and presence of excess wild type Elongin BC. Runoff transcription assays were performed in the presence of 4 nM TSK SP-NPR purified Elongin complexes of the indicated relative molar concentrations of purified Elongin BC complex; a relative molar concentration of 1 is equivalent to ~4 nM Elongin BC. BC, purified Elongin BC complex.
Figure 5D:
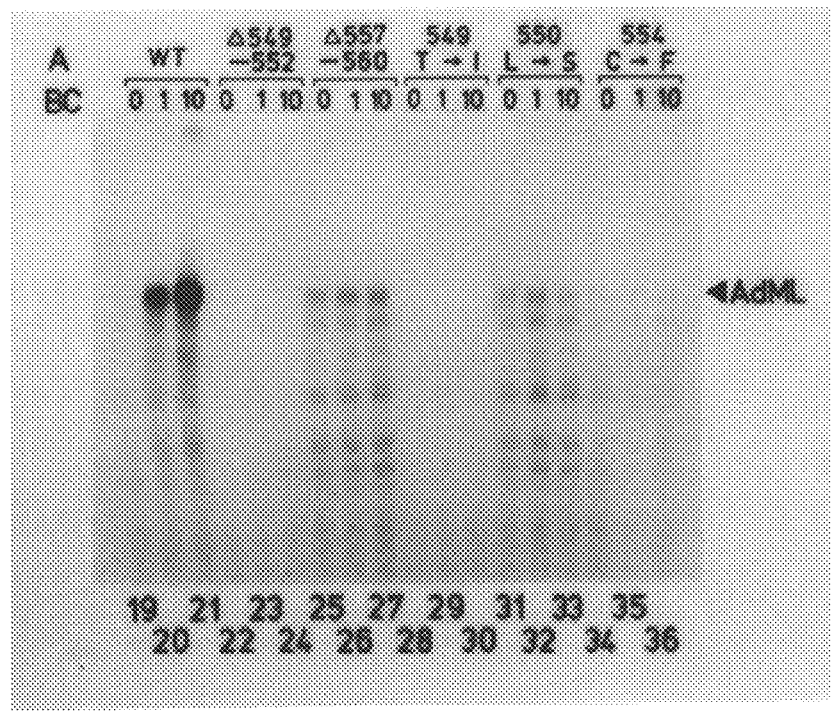
FIG. 5D. Runoff transcription assays were performed as described in the absence and presence of excess wild type Elongin BC. Runoff transcription assays were performed in the presence of 4 nM TSK SP-NPR purified Elongin complexes of the indicated relative molar concentrations of purified Elongin BC complex; a relative molar concentration of 1 is equivalent to ~4 nM Elongin BC. BC, purified Elongin BC complex.

To assess the transcriptional activities of the Elongin A internal deletion mutants, aliquots of peak fractions shown in FIG. 4B and 4C from TSK SP-NPR HPLC purification of mutant Elongin ABC complexes were assayed for their abilities to stimulate the rate of elongation by RNA Polymerase II. Because they co-purified with variable amounts of Elongin B and C, these mutants were assayed in the absence (FIG. 5A and 5B) and presence (FIG. 5C and 5D) of excess purified Elongin BC complex.

The results of these assays revealed that all Elongin A deletion mutants with mutations between amino acid residues 545 and 568 were transcriptionally impaired, although not all mutants were impaired to the same extent. Two Elongin A deletion mutants, Δ545–548 (SEQ ID NO:35) and Δ565–568 (SEQ ID NO:40), which efficiently formed isolable Elongin ABC complexes, exhibited reduced but readily detectable transcriptional activity, whereas Elongin A mutant Δ561–564 (SEQ ID NO:39), which could also bind Elongin B and C, exhibited little activity. In addition, two Elongin A deletion mutants, Δ549–552 (SEQ ID NO:36) and Δ553–556 (SEQ ID NO:37), which were severely impaired in their abilities to form isolable Elongin ABC complexes, exhibited little or no detectable transcriptional activity, whereas Elongin A mutant Δ557–560 (SEQ ID NO:38), which was also impaired in its ability to form an isolable Elongin ABC complex, exhibited detectable activity, raising the possibility that deletion of Elongin A residues between 556 to 561 (SEQ ID NO:41) may result in an increase in the basal activity of Elongin A.

Figure 6:
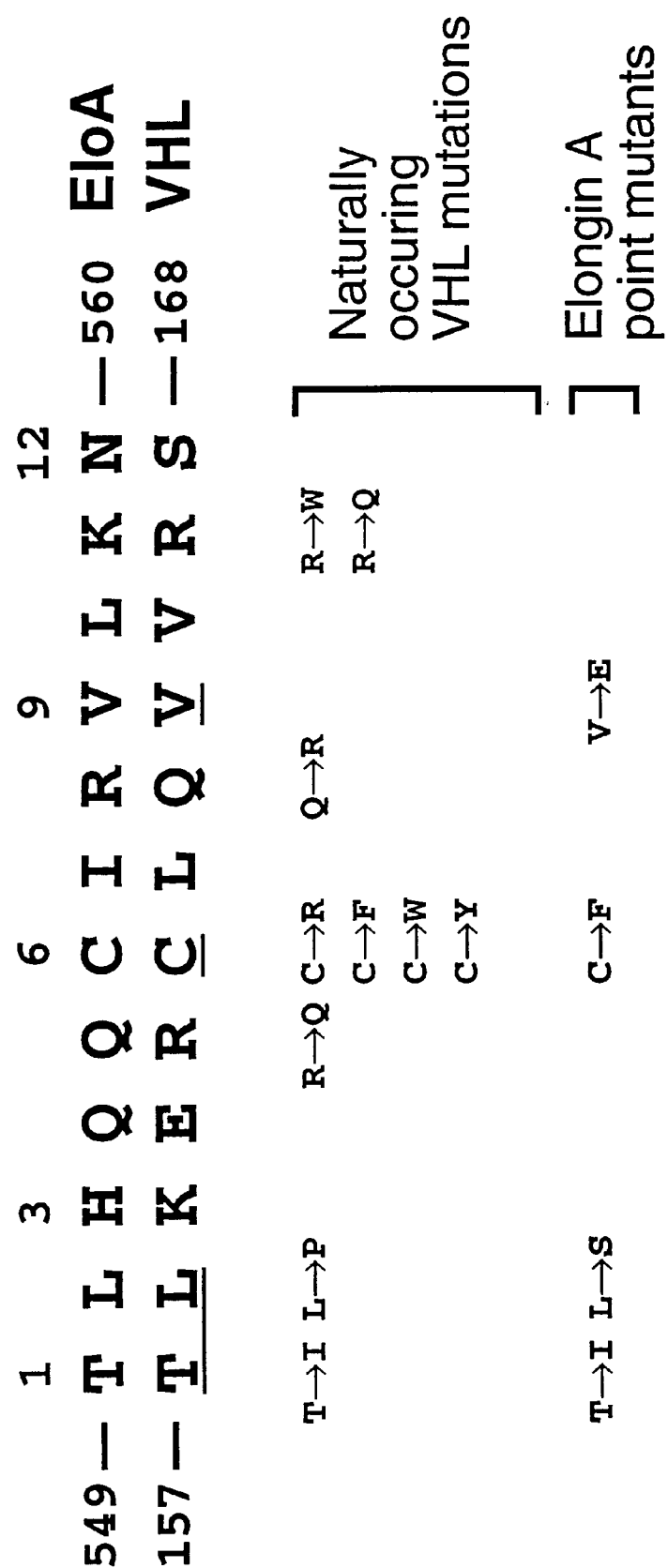
FIG. 6. Naturally occurring VHL mutants and synthetic Elongin A (SEQ ID NO:8) point mutants. EloA, Elongin A; VHL, VHL protein (amino acids 1–12 of SEQ ID NO:15).

The results described above indicate that Elongin A sequences most critical for binding to Elongin B and C fall within a 12 amino acid region between residues 549 and 560 (SEQ ID NO:8). Both Elongin A (SEQ ID NO:8) and the VHL protein (SEQ ID NO:15) share conserved threonine, leucine, cysteine, and valine residues in their Elongin BC binding region at the positions designated 1, 2, 6, and 9 in FIG. 6. The importance of these residues is further underscored by investigations of mutations found in VHL families and in clear-cell renal carcinoma which have identified naturally occurring VHL point mutations of the conserved threonine, leucine, and cysteine residues, but not of the conserved valine residue (Latif, et al., Science 260: 1317–1320 (1993); Gnarra, et al., Nature Genet 7: 85–90 (1994); Chen, et al., Hum Mutat 5: 66–75 (1995); Kanno, et al., Cancer Res 54: 4845–4847 (1994); Whaley, et al., Am J Hum Genet 55: 1092–1102 (1994); and Foster, et al., Hum Mol Genet 3: 2169–2173 (1994)).

To investigate the importance of these residues for Elongin A transcriptional activation activity, Elongin A mutants carrying point mutations of the conserved threonine, leucine, cysteine, and valine residues were constructed, expressed in E. coli, purified, and assayed for their abilities to form isolable Elongin ABC complexes and to stimulate the rate of elongation by RNA Polymerase II. As shown in FIG. 4B and 4C, each of the Elongin A point mutants, except L550S, formed readily detectable Elongin ABC complexes that could be purified by TSK SP-NPR HPLC, although Elongin A mutants T549I and C554F appeared somewhat impaired in their abilities to form Elongin ABC complexes.

To assess the transcriptional activities of the Elongin A point mutants, aliquots of peak fractions shown in FIG. 4B and 4C were assayed for their abilities to stimulate the rate of elongation by RNA Polymerase II in the absence (FIG. 5A and 5B) and presence (FIG. 5C and 5D) of excess purified Elongin BC complex. Only Elongin A point mutant V557E, which is mutated at a position where there are no corresponding naturally occurring VHL mutations, exhibited near wild type activity.

Evolutionary Conservation of the Elongin A Transcriptional Activation Domain

A TBLASTN search of the GenBank non-redundant database using rat Elongin A as the query sequence identified a predicted C. elegans ORF encoding a potential Elongin A homolog. By screening a C. elegans cDNA library with a probe derived from the predicted ORF, we isolated a cDNA encoding a highly basic, 434 amino acid protein (SEQ ID NO:42) with a calculated molecular mass of 49.2 kDa. Comparison of the predicted amino acid sequences of homolog revealed two conserved regions: an N-terminal region resembling the SIi-like N-terminus of mammalian Elongin A and a C-terminal region resembling the C-terminal transcriptional activation domain of mammalian Elongin A. Notably, the potential C. elegans Elongin A homolog exhibited the greatest similarity (33% identity, 53% similarity, alignment score 17.8 SD) to mammalian Elongin A residues 520 to 662 (SEQ ID NO:43), which includes the majority of the region most critical for transcriptional activity (FIG. 7). In addition, this region of the C. elegans protein includes a short sequence that resembles the Elongin BC binding site found in the VHL protein; however, it lacks the topoisomerase I catalytic site motif.

To determine the functional relationship between mammalian Elongin A and the potential C. elegans Elongin A homolog, the intact C. elegans ORF and two N-terminal deletion mutants C.e.EloA(94–434) (SEQ ID NO:44) and C.e.EloA(202–434) (SEQ ID NO:45) were constructed, expressed in E. coli, purified, and assayed for their abilities to interact with mammalian Elongin B and C and to stimulate the rate of elongation by mammalian RNA Polymerase II. Mutant C.e.EloA(94–434) (SEQ ID NO:44) lacks sequences related to SII, but contains sequences similar to the Elongin A transcriptional activation and Elongin BC binding site. Mutant C.e.EloA contains the potential Elongin BC binding site, but lacks sequences similar to the N-terminus of the transcriptional activation domain of mammalian Elongin A.

Figure 8A:
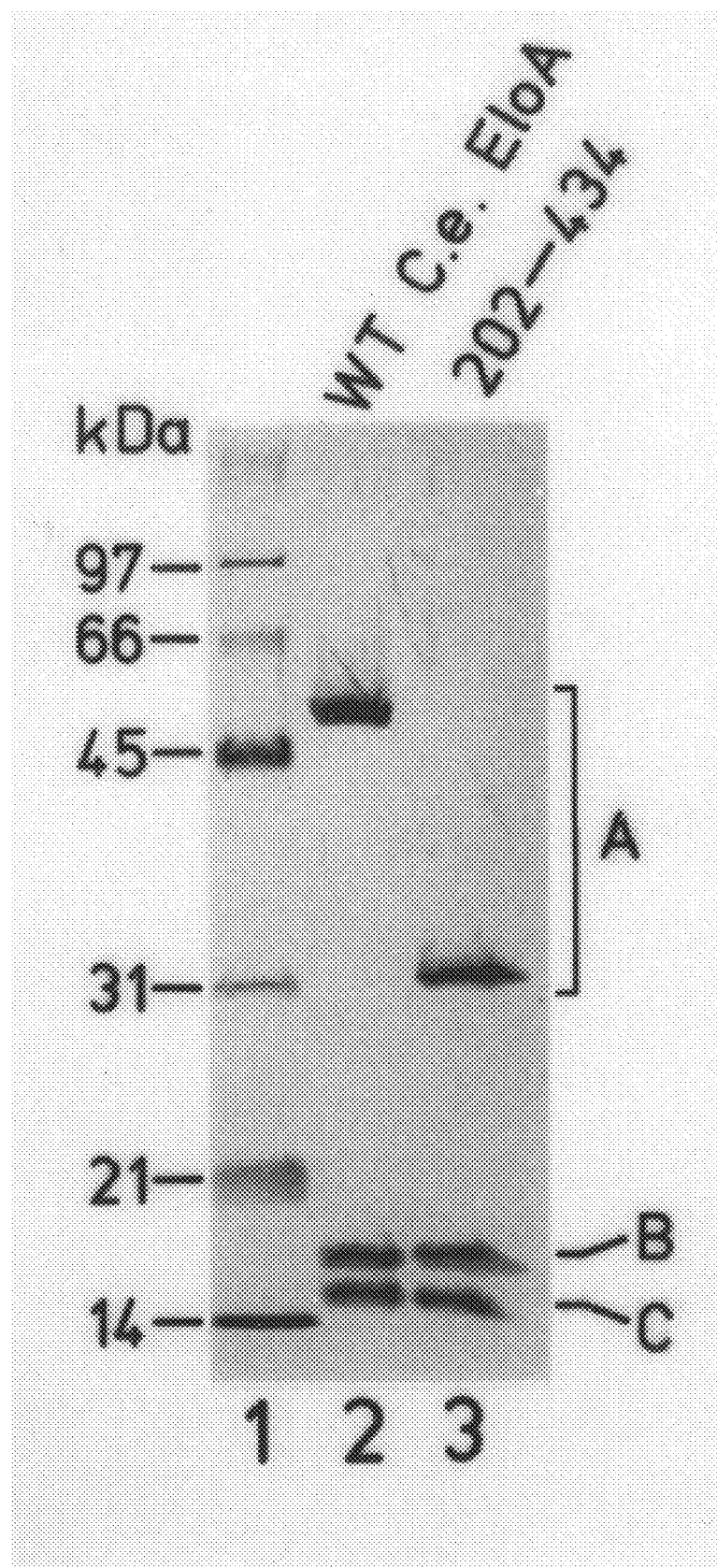
FIG. 8A. Analysis of wild type and mutant C. elegans Elongin A wherein wild type or mutant C. elegans Elongin A was refolded with rat Elongin B and C and subjected to TSK SP-NPR HPLC as described. Aliquots of the peak column fractions were analyzed by SDS-PAGE, and proteins were visualized by silver staining. WT C.e. EloA, wild type C. elegans Elongin A (SEQ ID NO:42); 202–434, C. elegans Elongin A mutant containing residues 202–434 (SEQ ID NO:45).
Figure 8B:
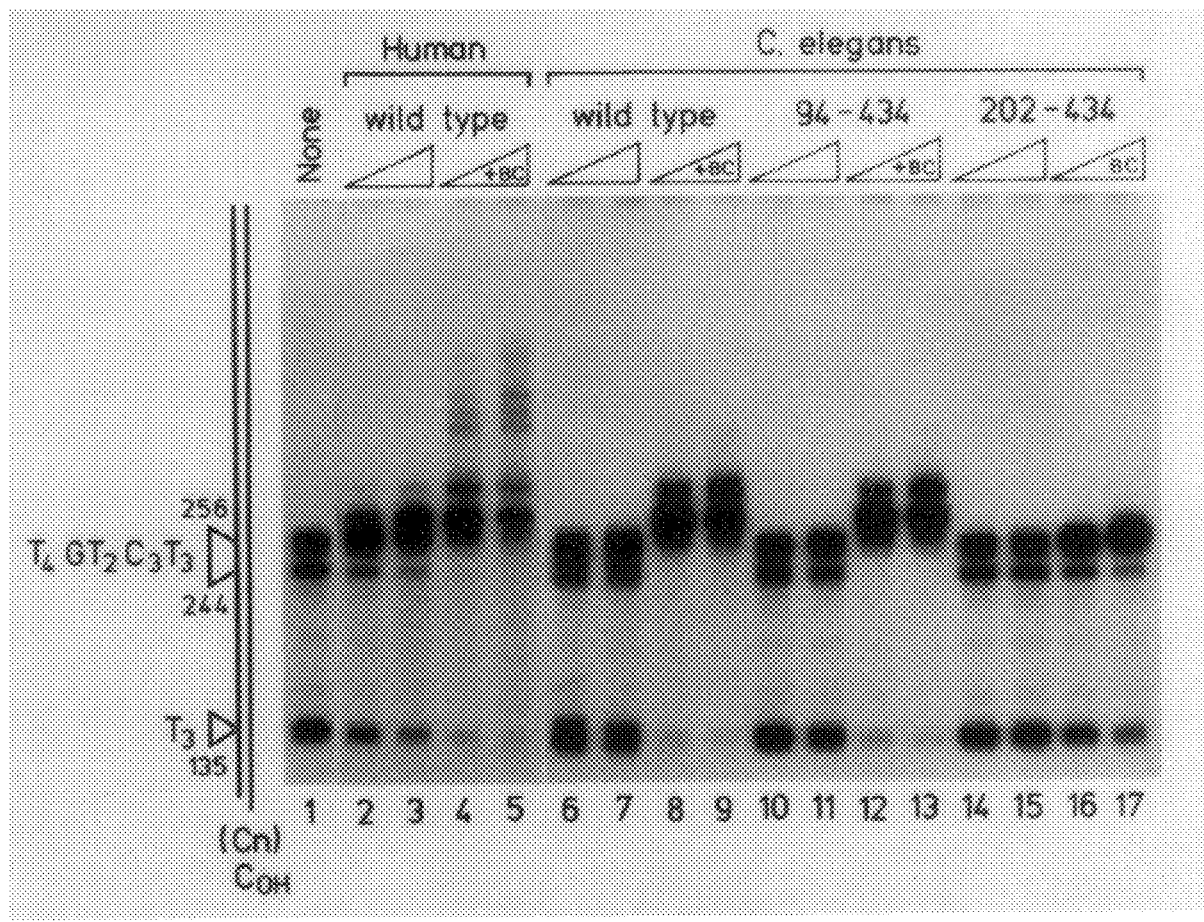
FIG. 8B. ~2 pmol of human or C. elegans Elongin A proteins were refolded as described (Bradsher, et al., *J Biol Chem* 268: 25587–25593 (1993)) in the presence or absence of ~2 pmol of rat Elongin B and C. Aliquots of refolded protein were assayed for transcriptional activity in oligo dc-tailed template assays performed as described. Reaction mixtures contained no Elongin (lane 1); 3 and 9 μl of renatured human Elongin A without (lanes 2 and 3) or with (lanes 4 and 5) Elongin B and C; 3 and 9 μl of renatured wild type C. elegans Elongin A without (lanes 6 and 7) or with (lanes 8 and 9) Elongin B and C; 3 and 9 μl of renatured C.e. EloA(94–434) (SEQ ID NO:44) without (lanes 10 and 11) or with (lanes 12 and 13) Elongin B and C; 3 and 9 μl of renatured C.e. EloA (202–434) (SEQ ID NO:45) with (lanes 14 and 15) or without (lanes 16, and 17) Elongin B and C.

Both the full-length C. elegans protein (SEQ ID NO:42) and mutants C.e.EloA(94–434) (SEQ ID NO:44) and C.e.EloA(202–434) (SEQ ID NO:45) were capable of binding to mammalian Elongin B and C (FIG. 8A and data not shown). In addition, the full-length C. elegans protein (SEQ ID NO:42) was capable of stimulating the rate of elongation by mammalian RNA Polymerase II in a reaction dependent on mammalian Elongin B and C (FIG. 8B). In these experiments, the transcriptional activities of mammalian Elongin A and the C. elegans protein were compared using an oligo(dC)-tailed template assay (Kadesch, T. R. and Chamberlin, M. J., J Biol Chem 257: 5286–5295 (1982); Tan, et al., Bio Techniques 16: 824–828 (1994)), which permits direct measurement of the effect of elongation factors on the rate of RNA chain elongation by RNA Polymerase II in the absence of initiation factors. Consistent with our results from analysis of mammalian Elongin A, mutant C.e.EloA(94–434)(SEQ ID NO:44), which contains the entire Elongin A-like transcriptional activation domain, was as active as the wild type C. elegans protein in stimulating the rate of elongation by mammalian RNA Polymerase II, whereas mutant C.e.EloA(202–434) (SEQ ID NO:45), which lacks the N-terminus of the Elongin A-like transcriptional activation domain, had significantly reduced activity.

Identification and Characterization of the Elongin C Domains Required for Interaction with Elongin B and Activation of Elongin A Elongin C is a 112 amino acid protein (SEQ ID NO:9) with a calculated mass of 12.4 kD as calculated from the amino acid sequence predicted from the cDNA. Elongin C is a regulatory subunit of the Elongin ABC which (i) functions as a potent stimulator of Elongin A transcriptional activation activity, (ii) interacts specifically with Elongin B to form an isolable Elongin BC complex, and (iii) is bound and negatively regulated in vitro by the product of the von Hippel-Lindau (VHL) tumor suppressor gene. As described herein, the Elongin C regions important for binding to Elongin B and for binding to and activating of Elongin A have now been localized.

Identification of an Elongin C Region Important for Binding to Elongin B

Figure 9A:
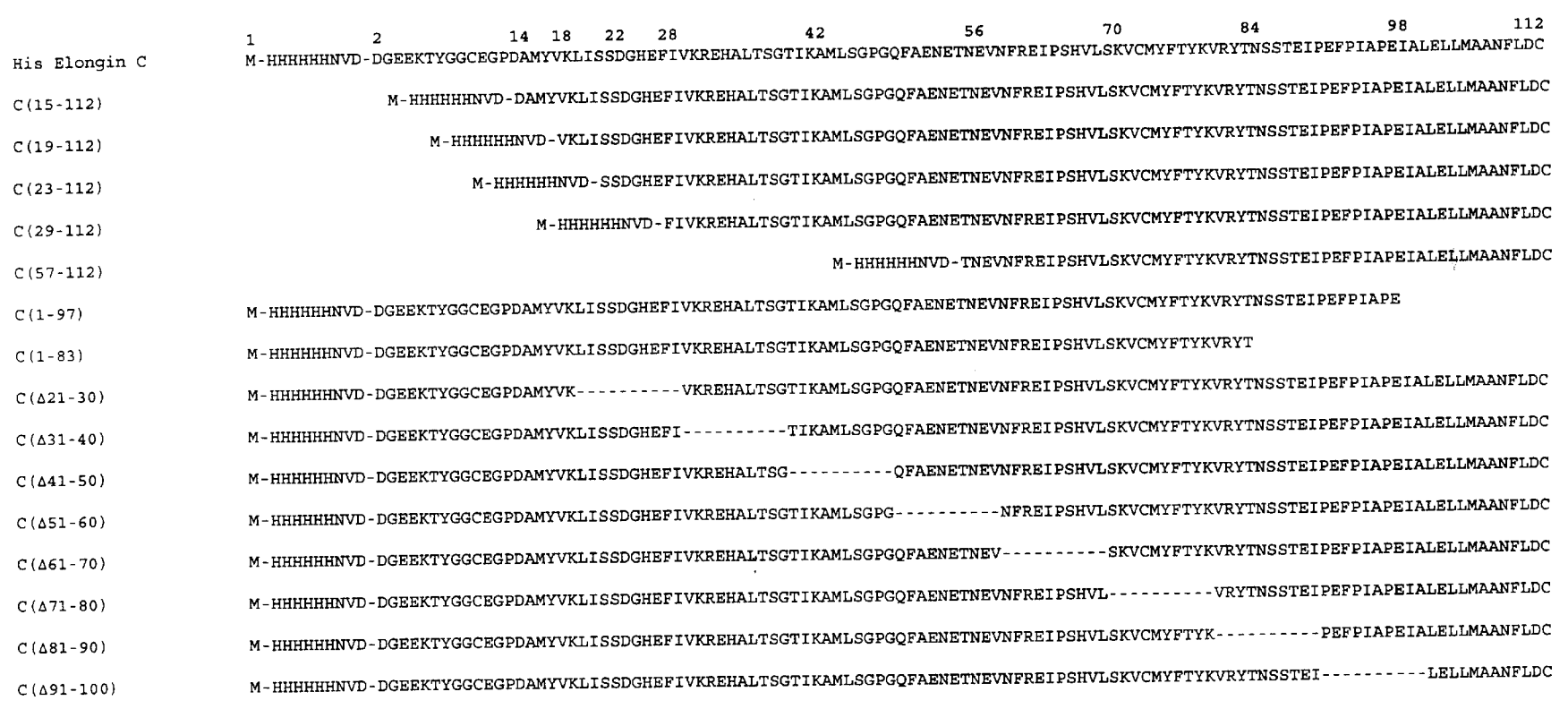

The regions of Elongin C which interact with Elongin B were localized using a systematic series of N-terminal, C-terminal, and internal Elongin C deletion mutants. These mutants (FIG. 9A and 9B) were constructed, expressed in E. coli, purified, and assayed for their abilities to form chromatographically isolable Elongin BC complexes. The mutants tested were: 15–112 (SEQ ID NO:46); 19–112 (SEQ ID NO:47); 23–112 (SEQ ID NO:48); 29–112 (SEQ ID NO:49); 57–112 (SEQ ID NO:50); 1–97 (SEQ ID NO:51); 1–83 (SEQ ID NO:52); Δ21–30 (SEQ ID NO:53); Δ31–40 (SEQ ID NO:54); Δ41–50 (SEQ ID NO:55); Δ51–60 (SEQ ID NO:56); Δ61–70 (SEQ ID NO:57); Δ71–80 (SEQ ID NO:58); Δ81–90 (SEQ ID NO:59); Δ91–100 (SEQ ID NO:60); Ala19–21 (SEQ ID NO:61); Ala22–24 (SEQ ID NO:62); Ala25–27 (SEQ ID NO:63); Ala28–30 (SEQ ID NO:64); Ala89–91 (SEQ ID NO:65); Ala92–94 (SEQ ID NO:66); Ala95–97 (SEQ ID NO:67); Ala98–100 (SEQ ID NO:68); Ala101–103 (SEQ ID NO:69); Ala104–106 (SEQ ID NO:70); Ala107–109 (SEQ ID NO:71); and Ala110–112 (SEQ ID NO:72).

Figure 10A:
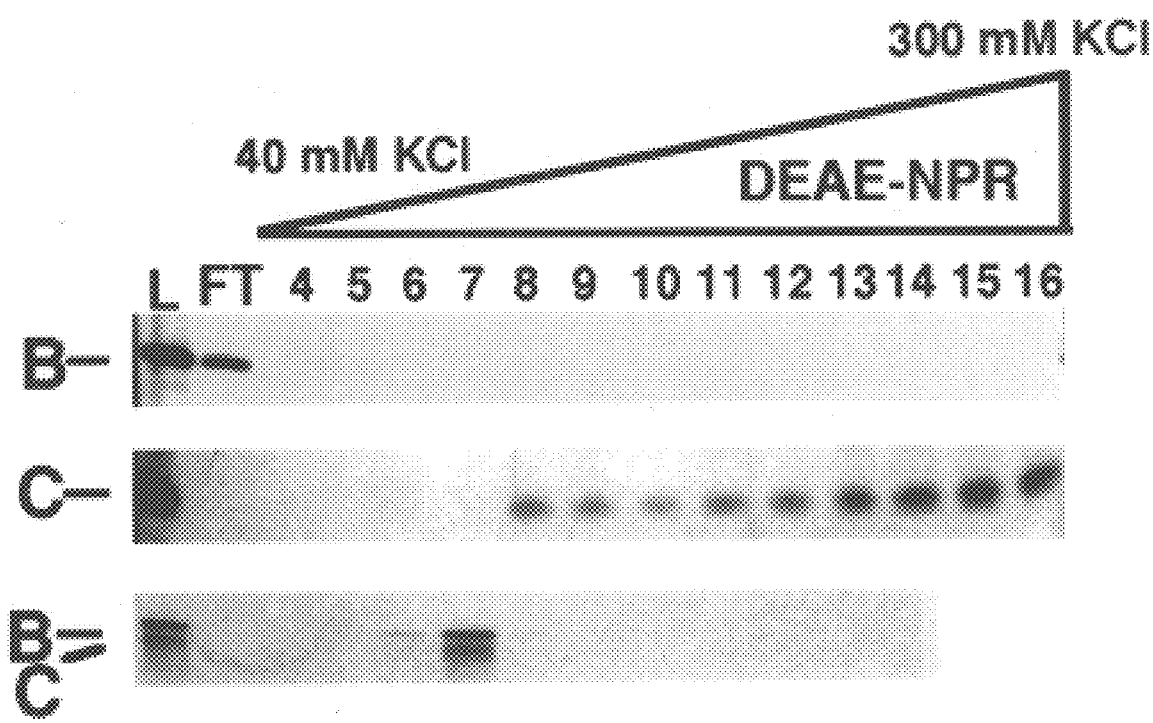
FIG. 10A. Assay of formation of Elongin BC complexes containing wild type and mutant Elongin C wherein wild type Elongin B (upper panel), wild type Elongin C (middle panel), or a mixture of wild type Elongin B and C were refolded and subjected to DEAE-NPR HPLC as described. Aliquots of the indicated column fractions were analyzed by SDS-PAGE, and proteins were visualized by silver staining.
Figure 10B:
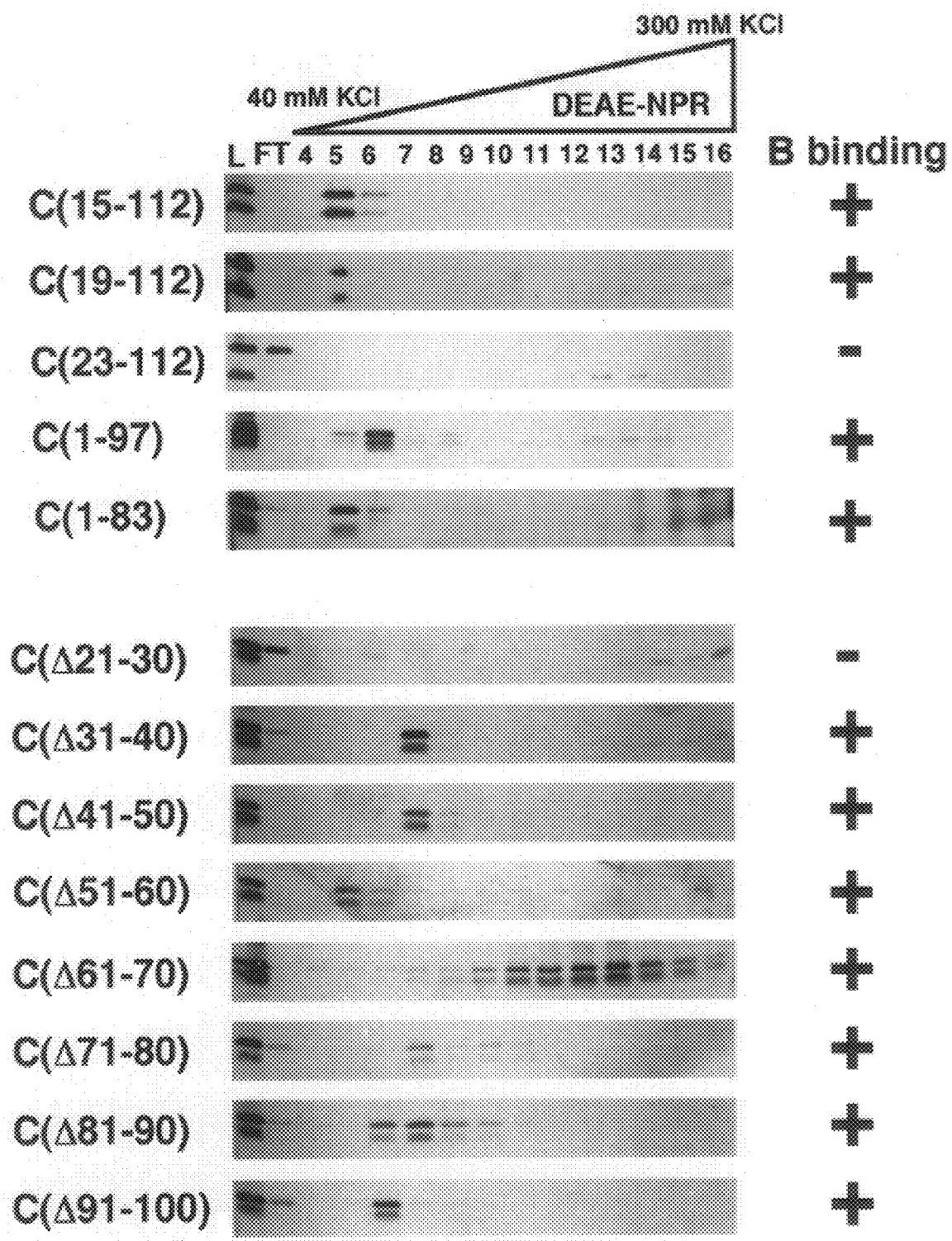
FIG. 10B. N-terminal, C-terminal, and internal Elongin C deletion mutants were assayed for their abilities to form Elongin BC complexes as described.

In these experiments, individual Elongin C mutants were refolded together with wild type Elongin B and subjected to TSK DEAE-NPR HPLC. The Elongin BC complex elutes from TSK DEAE-NPR as a discrete species with chromatographic properties distinct from those of both wild type Elongin B, which flows through TSK DEAE-NPR at low ionic strength, and wild type Elongin C, which binds tighter to this resin than the Elongin BC complex (FIG. 10A). As shown in FIG. 10B, deletion of as many as 29 amino acids from the C-terminus of Elongin C (SEQ ID NO:52) had no detectable effect on formation of isolable Elongin BC complexes. Likewise, deletion of as many as 18 amino acids from the N-terminus of Elongin C (SEQ ID NO:47) had no detectable effect on formation of isolable Elongin BC complexes.

Deletion of 22 amino acids (SEQ ID NO:48) from the N-terminus of Elongin C, however, abolished formation of isolable Elongin BC complexes. This suggests that Elongin C residues between 18 and 22 (SEQ ID NO:73) are critical for interaction of Elongin B and C. Consistent with this possibility, an Elongin C internal deletion mutant lacking residues 21 to 30 (SEQ ID NO:53) did not form an isolable Elongin BC complex (FIG. 10B). Notably, this mutant was the only Elongin C internal deletion mutant that failed to bind to Elongin B, suggesting that the Elongin C region between residues 18 and 30 (SEQ ID NO:74) either contains the Elongin B binding site or is crucial for proper folding of the protein.

Figure 10C:
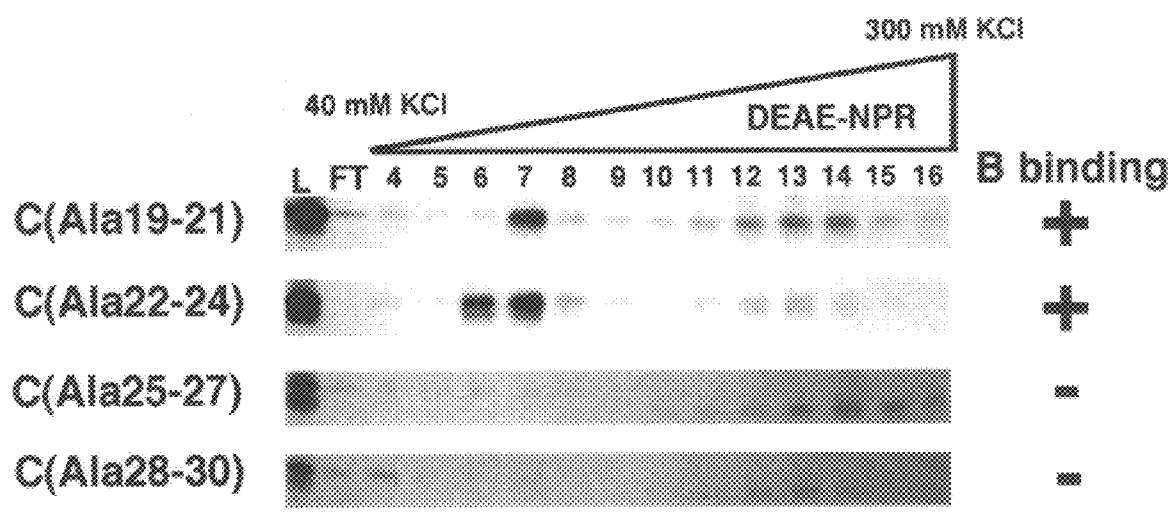

Further evidence supporting the importance of Elongin C sequences within this region, i.e., residues 18 to 30 (SEQ ID NO:74), for binding to Elongin B came from analysis of a set of clustered alanine scanning mutants in which Elongin C residues between amino acids 19 and 30 (SEQ ID NO:10) were mutated three at a time to alanines. As shown in FIG. 10C, although Elongin mutants C(Acanning mutants C(Ala19–21) (SEQ ID NO:61) and C(Ala22–24) (SEQ ID NO:62) were capable of assembling into isolable Elongin BC complexes, C(Ala25–27) (SEQ ID NO:63) and C(Ala28–30) (SEQ ID NO:64) were not.

Characterization of Elongin C Regions Important for Activation of Elongin A

Figure 11B:
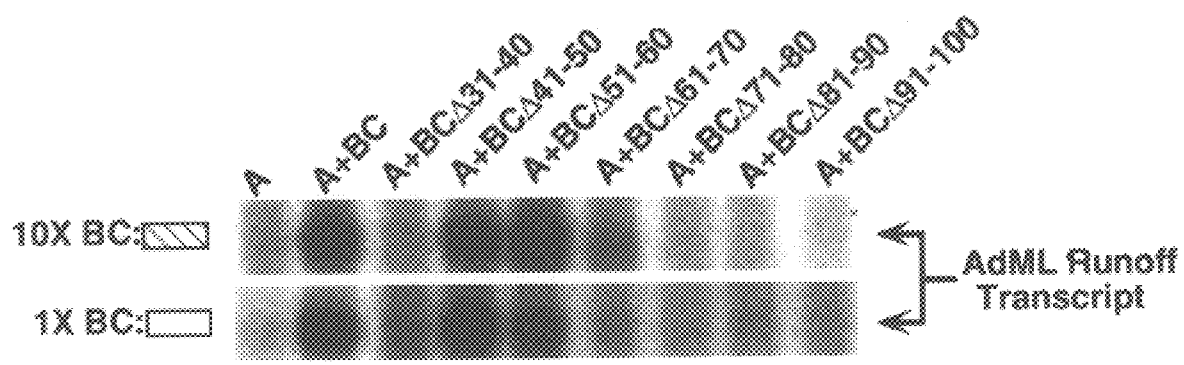
FIG. 11B. Runoff transcription assays were performed as described in the legend to FIG. 11A with Elongin BC complexes from the following DEAE-NPR fractions shown in FIG. 10B: wild type (SEQ ID NO:9), fraction 7, BC(Δ31–40) (SEQ ID NO:54), fraction 6; BC(Δ41–50) (SEQ ID NO:55), fraction 7; BC(Δ51–60) (SEQ ID NO:56), fraction 5; BC(Δ61–70) (SEQ ID NO:57), fraction 13; BC(Δ71–80) (SEQ ID NO:58), fraction 7; BC(Δ81–90) (SEQ ID NO:59), fraction 7; BC(Δ91–100) (SEQ ID NO:60), fraction 6.
Figure 11C:
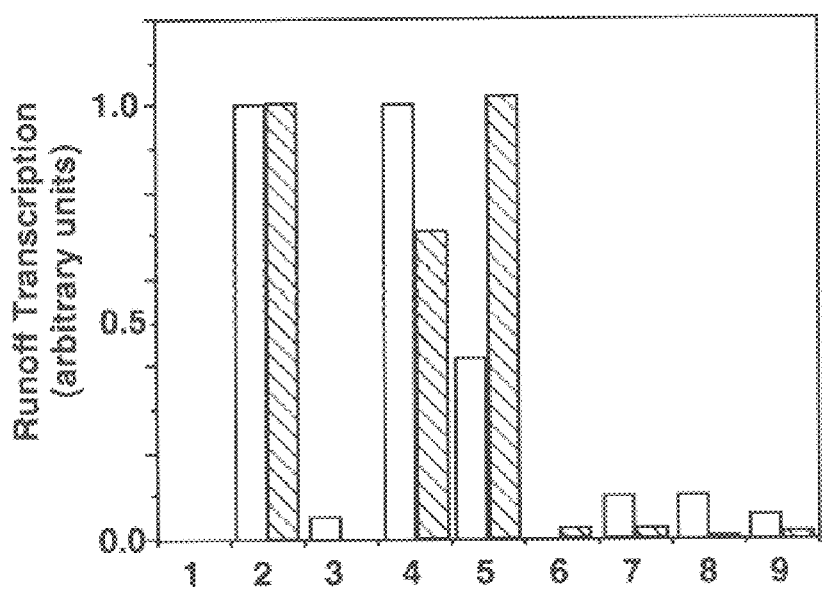
FIG. 11C. Runoff transcription assays were performed as described in the legend to FIG. 11A with Elongin BC complexes from the following DEAE-NPR fractions shown in FIG. 10B: wild type (SEQ ID NO:9), fraction 7, BC(Δ31–40) (SEQ ID NO:54), fraction 6; BC(Δ41–50) (SEQ ID NO:55), fraction 7; BC(Δ51–60) (SEQ ID NO:56), fraction 5; BC(Δ61–70) (SEQ ID NO:57), fraction 13; BC(Δ71–80) (SEQ ID NO:58), fraction 7; BC(Δ81–90) (SEQ ID NO:59), fraction 7; BC(Δ91–100) (SEQ ID NO:60), fraction 6. Runoff transcription is expressed in arbitrary units normalized to the amount of product synthesized in the presence of 1×(white boxes) or 10×(black boxes) wild type Elongin BC.

Pre-assembled Elongin BC complexes are capable of activating Elongin A. To investigate the requirements for activation of Elongin A by Elongin C, the isolated wild type and mutant Elongin BC complexes shown in FIG. 10A and FIG. 10B were assayed for their abilities to stimulate the rate of accumulation of runoff transcripts synthesized by RNA Polymerase II from the AdML promoter in a reconstituted transcription system containing purified Elongin A and the general initiation factors TBP, TFIIB, TFIIE, TFIIF, and TFIIH. As shown in FIGS. 11A, 11B, and 11C the entire C-terminal half of Elongin C is critical for activation of Elongin A by pre-assembled Elongin BC complexes. Elongin BC complexes containing Elongin C deletion mutants lacking up to 18 amino acids from their N-termini (SEQ ID NO:46; SEQ ID NO:47) or sequences between amino acids 41 and 60 (SEQ ID NO:55; SEQ ID NO:56) were capable of activating Elongin A. Elongin BC complexes containing Elongin C deletion mutants lacking as few as 15 amino acids from their C-terminal (SEQ ID NO:51) were inactive. (FIG. 11A) Furthermore, Elongin BC complexes containing Elongin C internal deletion mutants lacking sequences C-terminal to amino acid 61 (SEQ ID NO:57; SEQ ID NO:58; SEQ ID NO:59; SEQ ID NO:60) were inactive, and an Elongin BC complex containing the internal deletion mutant CΔ31–40 (SEQ ID NO:54), which lacks sequences immediately C-terminal to the region important for Elongin B binding, was also inactive.

Figure 12A:
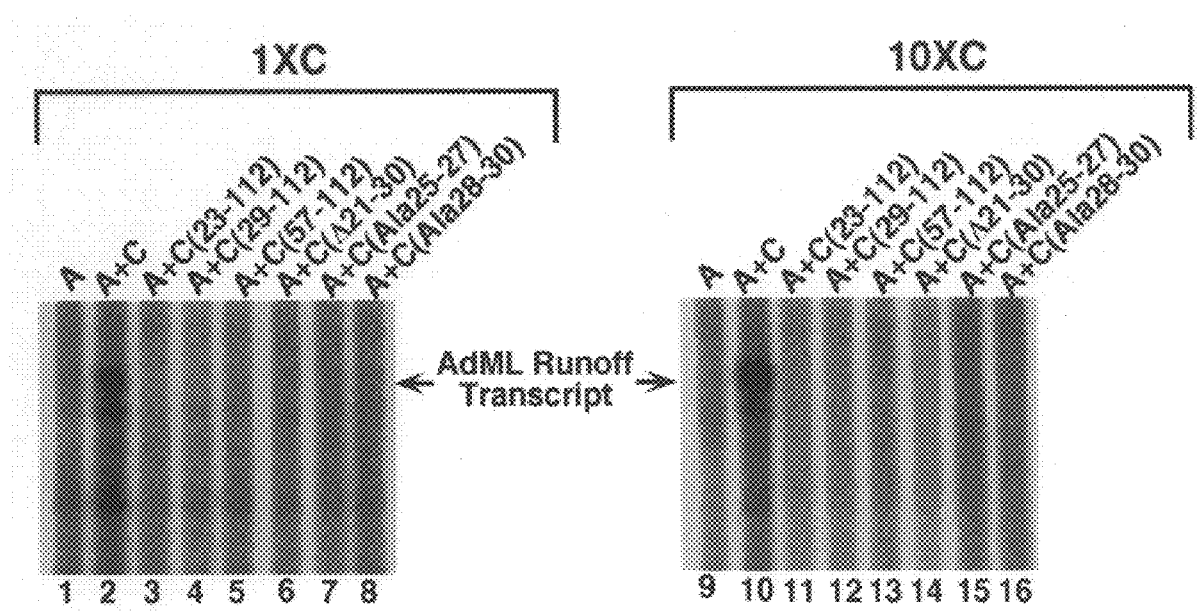
FIG. 12A. Assay of activation of Elongin A by Elongin C mutants that do not form isolable Elongin BC complexes. Runoff transcription assays were performed as described according to the protocol diagramed at the bottom of FIG. 11A. A mixture containing ~50 ng of SP-NPR purified Elongin A and ~5 ng (1×C) or ~50 ng (10×C) of $Ni^{2+}$-purified and refolded wild type or mutant Elongin C was preincubated on ice for 60 min and then added to reaction mixtures at ~10° C.
Figure 12B:
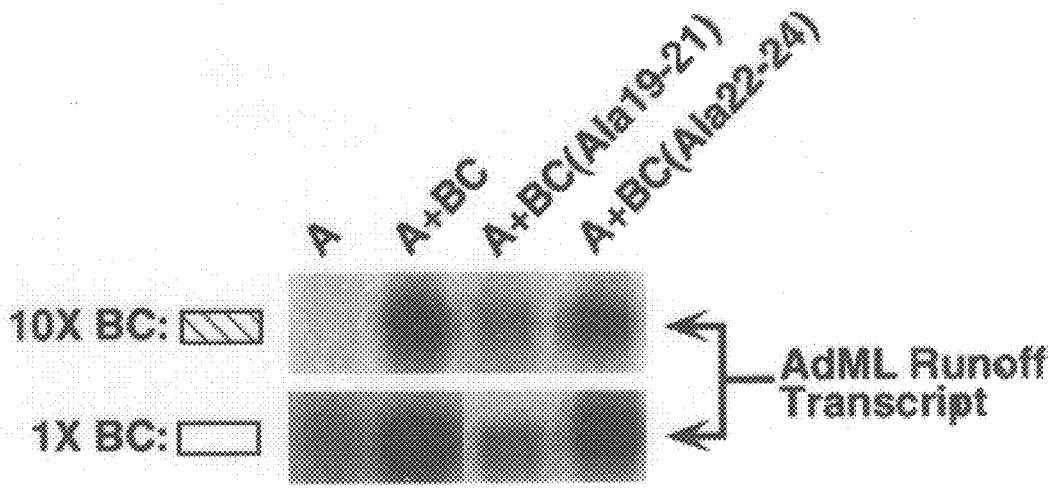
FIG. 12B. Assay of activation of Elongin A by C(Ala19–21) (SEQ ID NO:61) and C(Ala22–24) (SEQ ID NO:62). Runoff transcription assays were performed as described in the legend to FIG. 11A with Elongin BC complexes from the following DEAE-NPR fractions shown in FIG. 10C: wild type BC, fraction 7; BC(Ala19–21) (SEQ ID NO:61), fraction 7; BC(Ala22–24) (SEQ ID NO:62), fraction 7.
Figure 12C:
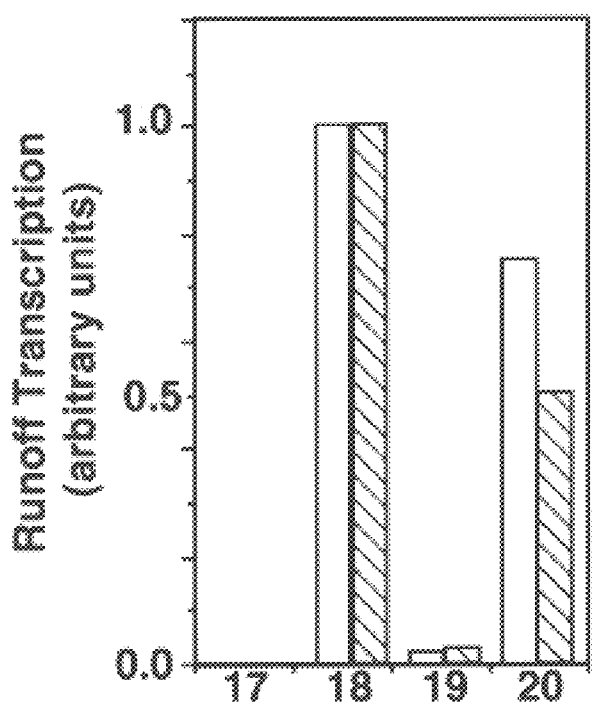
FIG. 12C. Assay of activation of Elongin A by C(Ala19–21) (SEQ ID NO:61) and C(Ala22–24) (SEQ ID NO:62). Runoff transcription assays were performed as described in the legend to FIG. 11A with Elongin BC complexes from the following DEAE-NPR fractions shown in FIG. 10C: wild type BC, fraction 7; BC(Ala19–21) (SEQ ID NO:61), fraction 7; BC(Ala22–24) (SEQ ID NO:62), fraction 7. Runoff transcription is expressed in arbitrary units normalized to the amount of product synthesized in the presence of 1×(white boxes) or 10×(black boxes) wild type Elongin BC.

Although Elongin B facilitates assembly and enhances stability of the Elongin ABC complex, it is not essential for activation of Elongin A by Elongin C. As described above, Elongin C mutants containing mutations in the region between amino acids 19 and 30 (SEQ ID NO:10) were unable to form isolable Elongin BC complexes. To investigate the ability of these Elongin C mutants to activate Elongin A, they were assayed for their abilities to stimulate the rate of accumulation of runoff transcripts synthesized by RNA Polymerase II from the AdML promoter in the presence of Elongin A and the general initiation factors, but in the absence of Elongin B. As shown in FIG. 12A, although wild type Elongin C strongly activated Elongin A, none of the Elongin C mutants containing mutations between amino acids 19 and 30 (SEQ ID NO:10), except alanine scanning mutant C(Ala22–24) (SEQ ID NO:62) (FIG. 12B and 12C), was capable of activating Elongin A. Thus, the Elongin C region between amino acids 19 and 30 (SEQ ID NO:10) is important for both Elongin B binding and activation of Elongin A.

To investigate whether Elongin C deletion mutants that fail to activate Elongin A are defective in their abilities to bind Elongin A, the Elongin C deletion mutants were assayed for their abilities to form chromatographically isolable Elongin ABC complexes. In these experiments, individual Elongin C deletion mutants were refolded together with wild type Elongin A and B and subjected to TSK SP-NPR HPLC. As described previously, Elongin A, Elongin AC and Elongin ABC complexes bind tightly to TSK SP-NPR and can all be eluted with ~0.3M KCl, whereas Elongin B and C flow through this resin at low ionic strength.

Figure 13:
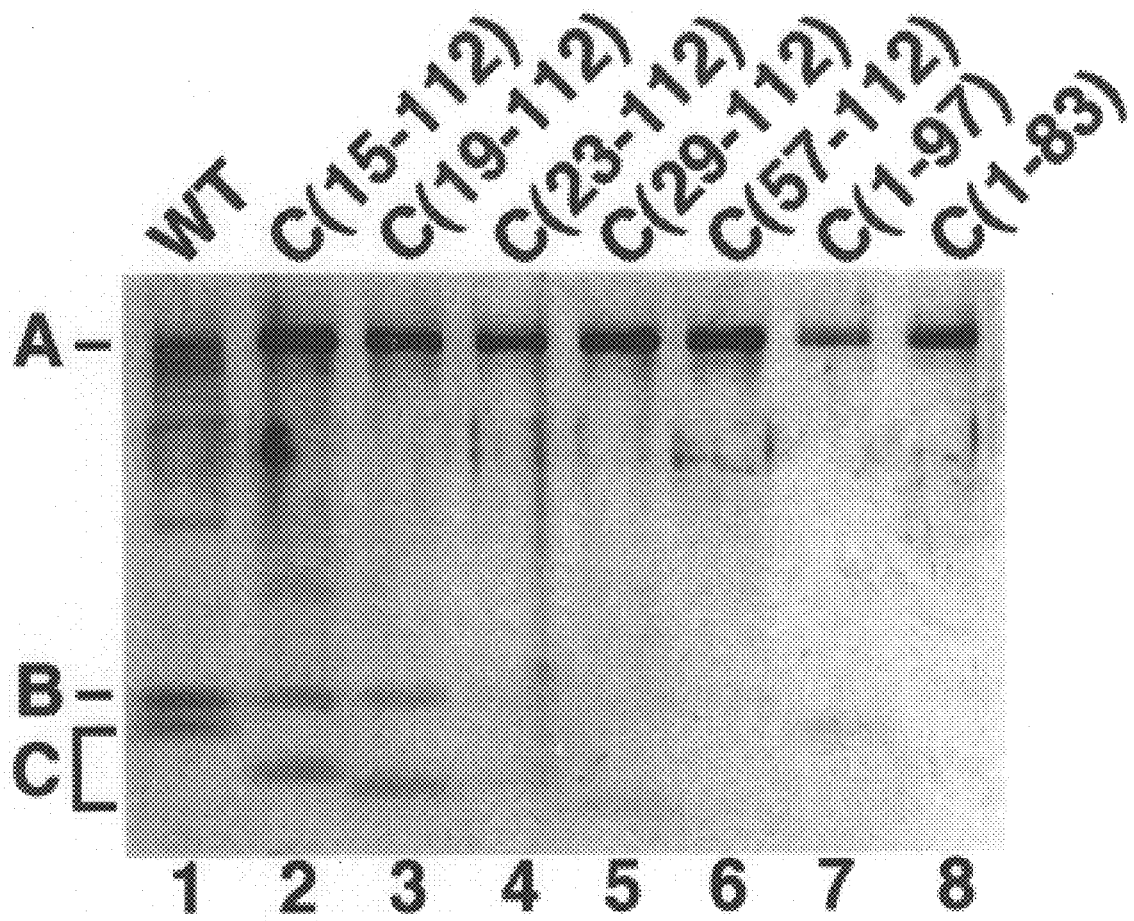
FIG. 13. Assay of formation of Elongin ABC complexes containing N-terminal and C-terminal Elongin C mutants. Mixtures containing wild type Elongin A and B and wild type or mutant Elongin C were refolded and subjected to SP-NPR HPLC as described. Aliquots of peak fractions from isolation of Elongin ABC complexes were analyzed by SDS-PAGE, and proteins were visualized by silver staining. A, Elongin A; B, Elongin B; C, wild type or mutant Elongin C.

As shown in FIG. 13, the N-terminal Elongin C deletion mutant C(15–112) (SEQ ID NO:46) and C(19–112) (SEQ ID NO:47), which form isolable Elongin BC complexes that activate Elongin A, were capable of assembling into isolable Elongin ABC complexes, whereas the remaining N-terminal and C-terminal Elongin C deletion mutants (C(23–112) (SEQ ID NO:48); C(29–112) (SEQ ID NO:49); C(57–112) (SEQ ID NO:50); C(1–97) (SEQ ID NO:51); and C(1–83) (SEQ ID NO:52)), each of which form inactive Elongin BC complexes, were unable to form isolable Elongin ABC complexes.

Figure 14A:
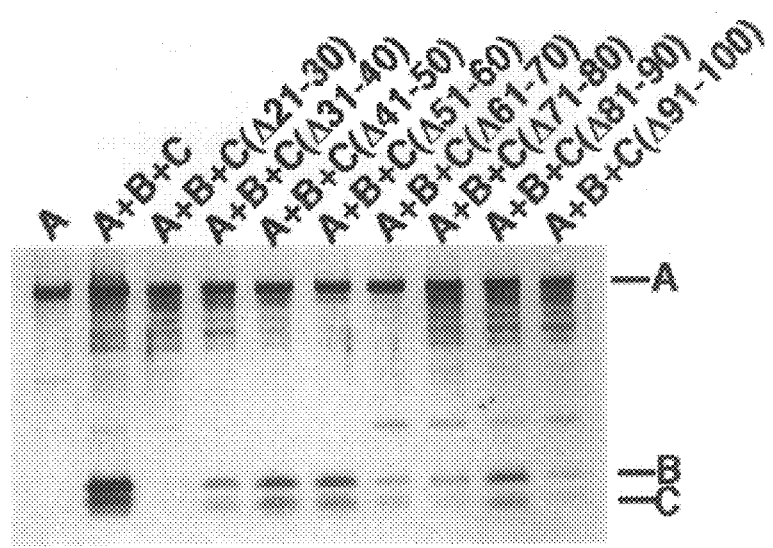
FIG. 14A. Assay of formation and activity of Elongin ABC complexes containing Elongin C internal deletion mutants wherein formation of Elongin ABC complexes was assayed as described in the legend to FIG. 13.

In contrast, with the exception of Elongin C internal deletion mutant, C(Δ21–30) (SEQ ID NO:53), which lacks residues 21 to 30 and does not form an isolable Elongin BC complex, each of the Elongin C internal deletion mutants (C(Δ31–40) (SEQ ID NO:54); C(Δ41–50) (SEQ ID NO:55); C(Δ51–60) (SEQ ID NO:56); C(Δ61–70) (SEQ ID NO:57); C(Δ71–80) (SEQ ID NO:58); C(Δ81–90) (SEQ ID NO:59); C(Δ91–100) (SEQ ID NO:60)) was capable of forming an isolable Elongin ABC complex (FIG. 14A). In these experiments, the yield of Elongin B and C in purified Elongin ABC complexes containing Elongin C internal deletion mutants was routinely less than their yield in purified Elongin ABC complexes containing wild type Elongin C, suggesting that Elongin ABC complexes containing the internal deletion mutants assemble less efficiently or are less stable than wild type Elongin ABC complexes.

Figure 14B:
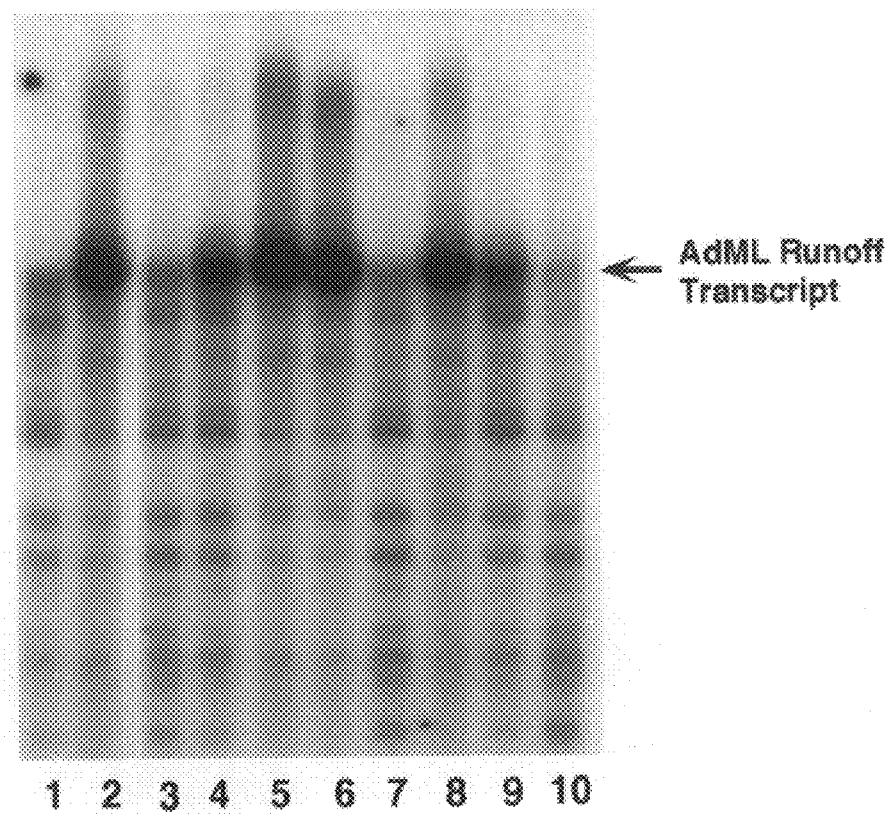
FIG. 14B. Runoff transcription assays were performed as described according to the protocol diagramed at the bottom of FIG. 11A. Isolated Elongin ABC complexes were added to reactions at −10° C. A, Elongin A; B, Elongin B; C, Elongin C.

Runoff transcription assays were used to compare the activities of the isolated wild type and mutant Elongin ABC complexes shown in FIG. 14A. The concentration of the wild type Elongin ABC complex in the reaction shown in lane 2 of FIG. 14B was sufficient to saturate the assay, and the concentrations of mutant Elongin ABC complexes were adjusted so that all reactions shown in FIG. 14B contained equivalent levels of Elongin A. Results of transcription assays highlighted the importance of sequences at the C-terminus of Elongin C for activation of Elongin A. Elongin ABC complexes containing Elongin C mutants Δ91–100 (SEQ ID NO:60), Δ61–70 (SEQ ID NO:57), and Δ21–30 (SEQ ID NO:53) were unable to stimulate the rate of elongation by RNA Polymerase II.

In addition, although Elongin BC complexes containing Elongin C internal deletion mutants C(Δ71–80) (SEQ ID NO:58) and C(Δ81–90) (SEQ ID NO:59) were unable to activate Elongin A, Elongin ABC complexes containing these same Elongin C mutants were capable of stimulating the rate of elongation by RNA Polymerase II, suggesting that the Elongin C region between amino acids 71 and 90 is not critical for activation of Elongin A in Elongin ABC complexes assembled by folding all three subunits together.

It is noteworthy that the activity of mutant Elongin ABC complexes does not, in all cases, correlate with the amount of Elongin B and C present. Elongin ABC complexes containing Elongin C internal deletion mutant C(Δ71–80) (SEQ ID NO:58) are considerably more active than those containing C(Δ81–90) (SEQ ID NO:59), even though Elongin ABC complexes containing C(Δ81–90) (SEQ ID NO:59) contain more Elongin B and C. Thus, the results of these experiments demonstrate that binding of Elongin C to Elongin A is not sufficient for activation of Elongin A, and they indicate the importance of the C-terminus of Elongin C for activation of Elongin A.

Figure 15A:
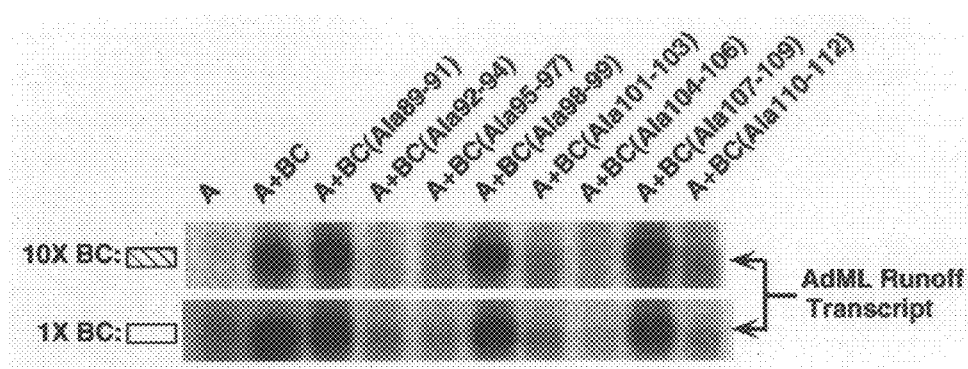
FIG. 15A. Assay of activation of Elongin A by isolated BC complexes containing Elongin C C-terminal alanine scanning mutants. Runoff transcription assays were performed as described in the legend to FIG. 11A.
Figure 15B:
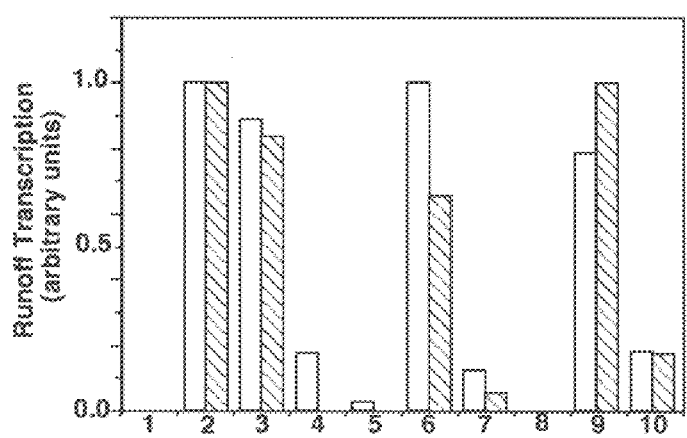
FIG. 15B. Assay of activation of complex by isolated BC complexes containing Elongin C C-terminal alanine scanning mutants. Runoff transcription assays were performed as described in the legend to FIG. 11A. Runoff transcription is expressed in arbitrary units normalized to the amount of product synthesized in the presence of 1×(white boxes) or 10×(black boxes) wild type Elongin BC.

Further evidence supporting the importance of the C-terminus of Elongin C in activation of Elongin A came from an analysis of a set of clustered alanine scanning mutants in which Elongin C residues between 89 and 112 (SEQ ID NO:75) were mutated three at a time to alanines. As predicted, all C-terminal alanine scanning mutants were capable of binding to Elongin B to form chromatographically isolable Elongin BC complexes (data not shown). In addition, although Elongin BC complexes containing three of these mutants, C(Ala89–91) (SEQ ID NO:65), C(Ala98–100) (SEQ ID NO:68), and C(Ala107–109) (SEQ ID NO:71), were nearly as active as wild type BC complexes, the activity of BC complexes containing C(Ala92–94) (SEQ ID NO:66), C(Ala95–97) (SEQ ID NO:67), C(Ala101–103) (SEQ ID NO:69), C(Ala104–106) (SEQ ID NO:70), and C(Ala110–112) (SEQ ID NO:72) was significantly impaired (FIG. 15A and 15B).

Figure 16:
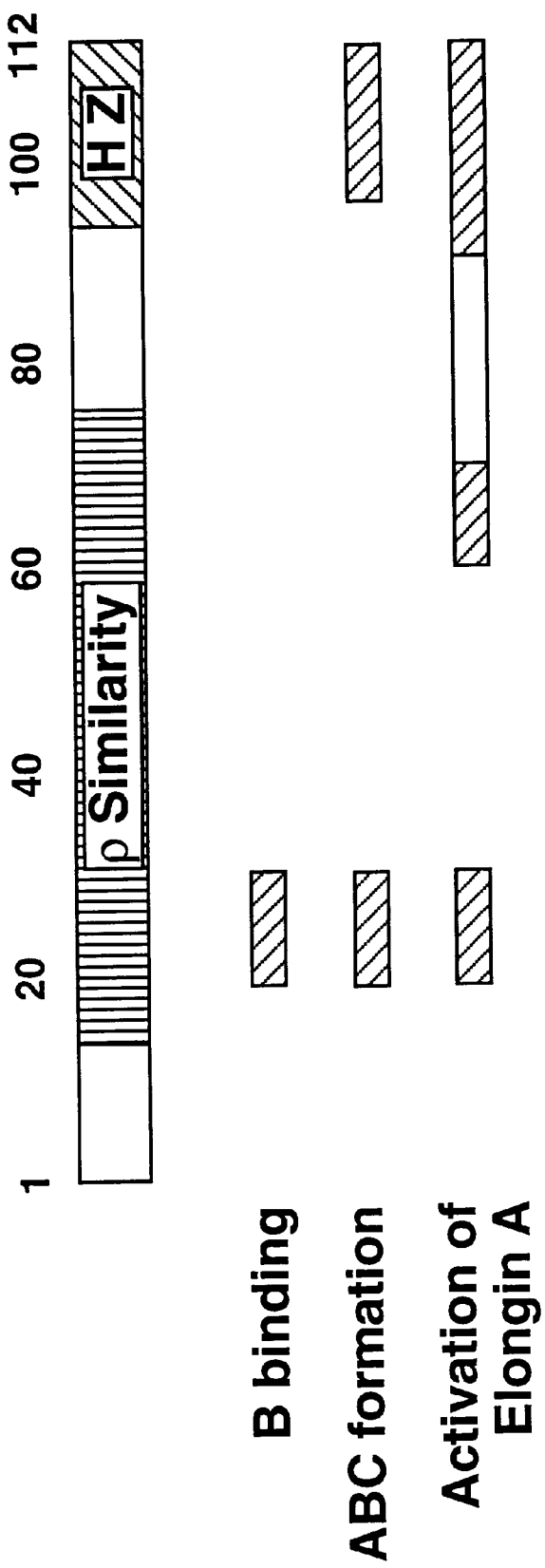
FIG. 16. Summary of Elongin C mutations that most strongly affect the ability of Elongin C to bind to Elongin B (B binding), to bind to Elongin A (A binding), and to activate Elongin A (Activation of Elongin A). Mutations in the region indicated by the open box strongly affect activation of Elongin A by isolated Elongin BC complexes but not of isolated Elongin ABC complexes. HZ, hydrophobic zipper.

Elongin C mutations fall into several classes based on their effects on Elongin C activities (FIG. 16). First, the only Elongin C mutations that had dramatic effects on Elongin B binding fell within a short Elongin C region between amino acids 19 and 30 (SEQ ID NO:10). This is consistent with the possibility that sequences within this region are directly involved in interactions with Elongin B. Deletion mutations in this region, however, were also found to affect the ability of Elongin C to assemble into isolable Elongin ABC complexes and to activate Elongin A transcriptional activity. Thus, it is also possible that some mutations in this region disrupt the overall tertiary structure of Elongin C.

Second, the only Elongin C mutations that had dramatic effects on formation of isolable Elongin ABC complexes without affecting formation of Elongin BC complexes were mutations in the extreme C-terminus of Elongin C. This result, together with our finding that all Elongin C internal deletion mutants (C(Δ31–40) (SEQ ID NO:54); C(Δ41–50) (SEQ ID NO:55); (CΔ51–60) (SEQ ID NO:56); C(Δ61–70) (SEQ ID NO:57); C(Δ71–80) (SEQ ID NO:58); C(Δ81–90) (SEQ ID NO:59); and C(Δ91–100) (SEQ ID NO:60), except C(Δ21–30) (SEQ ID NO:53), were capable of forming isolable Elongin ABC complexes, suggests that the C-terminus of Elongin C plays a crucial role in binding Elongin A.

Third, Elongin C mutations that affect formation of Elongin ABC complexes are only a subset of those mutations that affect the elongation activation activity of Elongin A, indicating that binding of Elongin C by Elongin A is not sufficient for activation of Elongin A. Interestingly, the size of the Elongin C region sensitive to mutations that affect activation of Elongin A was dependent on the assay used to measure activation. In one assay, which measured the ability of Elongin C or Elongin BC complexes to stimulate the rate of elongation by RNA Polymerase II in the presence of Elongin A, Elongin C mutations that fell within the entire C-terminal half of the protein (residues 61–112) (SEQ ID NO:76) drastically reduced Elongin C activity. In contrast, in a second assay, which measured the ability of preassembled Elongin ABC complexes to stimulate the rate of elongation by RNA Polymerase II, Elongin C mutations that fell between residues 71 and 90 had a significantly reduced effect on Elongin A activity, indicating that sequences within this Elongin C region are not essential for activation of Elongin A.

EXAMPLES

Identification of Elongin A Domains

Example 1

Materials

Unlabeled ultrapure ribonucleoside 5'-triphosphates were purchased from Pharmacia Biotech Inc. (Piscata way, N.J.) [$\alpha$-$^{32}$P] CTP (>400 Ci/mmol) was obtained from Amersham Corp. (Arlington Heights, Ill). Phenylmethylsulfonyl fluoride (PMSF), heparin, and polyvinyl alcohol type II were from Sigma Chemical Co. (St. Louis, Mo.). Bovine serum albumin (Pentex fraction V) was purchased from ICN ImmunoBiologicals (Costa, Mesa, Calif.). Glycerol (Spectranlyzed grade) and guanidine hydrochloride (electrophoresis grade) were obtained from Fisher Scientific (Pittsburgh, Pa.).

Example 2

Expression and Purification of Wild Type and Mutant Rat Elongin A

Overexpression of rat Elongin A mutants in *E. coli* was accomplished using an M13mpET bacteriophage expression system Garrett et al., *Proc Natl Acad Sci USA* 91: 5237–5241(1994); Garrett, et al., *Proc Natl Acad Sci USA* 92: 7172–7176 (1995)). Constructs for expression of 6-histidine-tagged N- and C-terminal Elongin A deletion mutants, were prepared by inserting PCR generated fragments of the Elongin A cDNA into the Sal I and Bam HI sites of M13mpET. Constructs for expression of Elongin A internal deletion and point mutants were prepared by oligonucleotide-directed mutagenesis (Kunkel, T.A., *Proc Natl Acad Sci USA* 82: 488–492 (1985) using the MUTA-GENE® M13 in vitro mutagenesis kit (Bio-Rad). Elongin A mutants were sequenced by the dideoxy chain-termination method using a SEQUENASE kit (United States Biochemicals).

To prepare Elongin A mutants, 500 ml cultures of *E. coli* strain JM109(DE3) were grown to an OD$_{600}$ of 0.6 in Luria broth containing 2.5 mM MgCl$_2$ at 37° C. with gentle shaking. Cells were infected with M13mpET vectors carrying mutant Elongin A cDNAs at a multiplicity of infection of 20. After an additional 2 hours at 37° C., cells were induced with 0.4 mM isopropyl $\beta$-D-thiogalactoside, and cultures were incubated for an additional 2.5 hours. Cells were harvested by centrifugation at 2000×g for 10 min at 4° C. The cell pellets were resuspended in 25 ml of ice-cold 20 mM Tris-HCl (pH 8.0), 10 mM imidazole (pH 8.0), and 1 mg/ml lysozyme and incubated on ice for 30 min. After 2 cycles of freeze-thaw, the suspension was centrifuged at 100,000×g for 35 min at 4° C. Inclusion bodies were solubilized by resuspension in 25 ml of ice-cold 50 mM Tris-HCl (pH 8.0) containing 6M guanidine hydrochloride, and the resulting suspension was clarified by centrifugation at 50,000×g for 20 min at 4° C. Recombinant Elongin A mutants were purified from the supernatant by Ni$^{2+}$-nitrilotriacetic acid-agarose (Invitrogen) affinity chromatography as described (Garrett, et al., *Proc Natl Acad Sci USA* 91: 5237–5241 (1994); Aso, et al., *Science* 269: 1439–1443 (1995)).

Example 3

Reconstitution and Purification of Elongin Complexes Containing Elongin A Mutants Recombinant Elongin B and C were expressed in *E. coli* using the M13mpET bacteriophage expression system and purified as described previously (Garrett, et al., *Proc Natl Acad Sci USA* 91: 5237–5241 (1994); Garrett, et al., *Proc Natl Acad Sci USA* 92: 7172–7176 (1995)). Reconstitution of Elongin complexes was carried out essentially as described (Aso, et al., *Science* 269: 1439–1443 (1995)) by refolding ~50 $\mu$g of wild type or mutant Elongin A, ~8 $\mu$g of Elongin B, and ~8 $\mu$g of Elongin C. Following dialysis, the mixtures were centrifuged at 60,000×g for 15 min at 4° C. The resulting supernatant were applied to TSK SP-NPR columns (35 mm×4.6 mm, Hewlett-Packard) equilibrated in 40 mM Hepes-NaOH (pH 7.9), 0.1 mM EDTA, 1 mM DTT, 10% (v/v) glycerol; and 0.1M KCl and fractionated using a SMART microchromatography system (Pharmacia) at 8° C. The columns were eluted at 0.6 ml/min with a 9 ml linear gradient from 0.1 to 0.8M KCl in the same buffer.

Aliquots of each column fraction were analyzed by 12% SDS-polyacrylainide gel electrophoresis (PAGE), and the proteins were visualized by silver staining.

Example 4

Preparation of RNA Polymerase II and Initiation Factors

RNA Polymerase II (Conaway, J. W. and Conaway, R. C, *Science* 248: 1550–1553 (1990)) and TFIIH (rat $\delta$, TSK DEAE 5-PW fraction) (Conaway et al. *J Biol Chem* 267: 10142–10148 (1992)) were purified as described from rat liver nuclear extracts. Recombinant yeast TBP (Conaway, et al., *J Biol Chem* 266: 7804–7811 (1991) and rat TFIIB (rat $\alpha$) (Tsuboi, et al., *Nucle Acids Res* 20: 3250 (1992) were expressed in *E. coli* and purified as described. Recombinant TFIIE was prepared as described (Peterson, et al., *Nature* 354: 369–373 (1991), except that the 56 kDa subunit was expressed in BL21(DE3)-pLysS. Recombinant TFIIF was purified as described (Tan, et al., *Bio Techniques* 16: 824–828 (1994)) from *E. coli* strain JM109 (DE3) infected with M13mpET-RAP30 and M13mpET-RAP74.

Example 5

Runoff Transcription Assays

Unless indicated otherwise, preinitiation complexes were assembled as described (Gerrett, et al., *Proc Natl Acad Sci*

USA 92: 7172–7176 (1995) by preincubation of 50 ng of the EcoRl to Ndel fragment from pDN-AdML (Conaway, R. C. and Conaway, J. W., *J Biol Chem* 263: 2962–2968 (1988) and approximately 10 ng of recombinant TFIIB, 10 ng of recombinant TFIIF, 7 ng of recombinant TFIIE, 40 ng of TFIIH (rat δ, fraction VI), 50 ng of recombinant yeast TBP (AcA 44 fraction), and 0.01 units of RNA Polymerase II. Transcription was initiated by addition of 7 mM $MgCl_2$, 50 μM ATP, 2 μM UTP, 10 μM CTP, 50 μM GTP, and 10 μCi [α-$^{32}$P] CTP, either in the presence or absence of Elongin preparations. After incubation at 28° C. for the times indicated in the legends, runoff transcripts were analysed by electrophoresis through 6% polyacrylamide, 7.0M urea gels. Transcription was quantitated using a Molecular Dynamics PHOSPHOIMAGER™.

Example 6

Oligo(dC)-Tailed Template Assay of Elongation by RNA Polymerase II

Pulse-chase assays were carried out essentially as described (Aso et al., *Science* 269: 1439–1443 (1995). 0.01 unit of RNA Polymerase III and 100 ng of pCpGR22OS/P/X were incubated at 28° C. in the presence of 20 mM Hepes-NaOH, pH 7.9, 20 mM Tris-HCl, pH 7.9, 2% (w/v) polyvinyl alcohol, 0.5 mg/ml bovine serum albumin, 60 mM KCl, 50 μM $ZnSO_4$, 7 mM $MgCl_2$, 0.2 mM dithiothreitol, 3% (v/v) glycerol, 3 units of recombinant RNASIN (Promega), 50 μM ATP, 50 μM GTP, 2 μM CTP, and 10 μCi of [α-$^{32}$P] CTP. After 25 min of labeling, the reactions were chased for 7.5 min following addition of 100 μM non-radioactive CTP, 2 μM UTP, and the indicated amounts of Elongin preparations. Transcripts were analysed by electrophoresis through 6% polyacrylamide, 7.0M urea gels.

Example 7

Isolation of CDNA Encoding *C. elegans* Elongin A

A homology search of the GeneBank database using rat Elongin A protein sequence as the query revealed that nucleotides 19335 through 21154 of *C. elegans* cosmid R03D7 contained a predicted ORF encoding a protein highly homologous to portions of Elongin A. A λ ZAP C. elegans cDNA library was constructed and screened with the 5'-$^{32}$P-labeled oligonucleotide 5'-GAG TTG GTC AGT GCT CGC GTG GTC AAG AAC AGG CTT CAG TAG ATC AAA TGG-3' (SEQ ID NO:77), which corresponds to a portion of the predicted ORF. Hybridization was performed at 65° C. for 20 hours in 5×standard saline citrate, 5×Denhardt's solution, 100 mM sodium phosphate, 0.1% sodium dodecyl sulfate, 10% dextran sulfate containing denatured salmon testis DNA (100 μg/ml). Three overlapping cDNA clones with inserts of up to 1.8 kb were isolated. Clone CE22, which contained the longest insert, was sequenced on both strands by the dideoxy chain termination method using a SEQUENASE kit (United States Biochemicals (Cleveland, Ohio).

Example 8

Expression and Purification of *C. elegans* Elongin A

Histidine-tagged *C. elegans* Elongin A was overexpressed in *E. coli* using a pET16b expression vector (Novagen (Madison Wis.). The pET16b constructs for expression of histidine-tagged wild type and mutant *C. elegans* Elongin A were prepared by insertion of PCR-generated fragments of the *C. elegans* ORF into the Nde I and Bam HI sites of the pET16b vector. A 100 ml culture of *E. coli* strain BL21 (DE3) transformed with pET16b carrying the *C. elegans* Elongin A cDNA was grown to an $OD_{600}$ of 0.6 in Luria broth containing 50 μg/ml ampicillin at 37° C. Following induction with 1 mM isopropyl β-D-thiogalactoside, the culture was incubated for an additional 2.5 hours at 37° C. Cells were harvested by centrifugation at 2000×g for 10 min at 4° C. The cell pellet was resuspended in 5 ml of ice-cold 20 mM Tris-HCl (pH 8.0), 10 mM imidazole (pH 8.0), and 1 mg/ml lysozyme and incubated on ice for 30 min. After 2 cycles of freeze-thaw, the suspension was centrifuged at 100,000×g for 35 min at 4° C. Inclusion bodies were solubilized by resuspension in 5 ml of ice-cold 50 mM Tris-HCl (pH 8.0) containing 6M guanidine hydrochloride, and the resulting suspension was clarified by centrifugation at 50,000×g for 20 min at 4° C. Recombinant wild type and mutant *C. elegans* Elongin A were purified from the supernatant by $Ni^{2+}$-nitrilotriacetic acid-agarose (Invitrogen, San Diego, Calif.) affinity chromatography as described (Garrett et al., *Proc Natl Acad Sci USA* 91: 5437–5241 (1994).

Identification of Elongin C Domains

Example 9

Materials

Unlabeled ultrapure ribonucleoside 5'-triphosphates were purchased from Pharmacia Biotech Inc. Restriction enzymes were obtained from American Allied Biochemicals (Aurora, Colo.) or Promega (Madison, Wis.). [α-$^{32}$P] CTP (>650 Ci/mmol) was from Amersham Corp. Proteinase K and isopropyl β-D-thiogalactoside (IPTG) were purchased from Sigma Chemical Co. Bovine serum albumin (Pentex fraction V, reagent grade) was obtained from ICN Immunobiologicals. Guanidine hydrochloride (Sequanal grade) was obtained from Pierce Chemical Co. (Rockfrod, Ill.) Phenyl-methylsulfonyl fluoride (PMSF) was from Sigma Chemical Co. and was dissolved in dimethylsulfoxide to 1M. Polyvinyl alcohol (average molecular weight 30,000–70,000) was from Sigma Chemical Co. and was dissolved in water to 20% (w/v) and centrifuged or filtered through a 0.2μ filter prior to use.

Example 10

DNA Template for Transcription pDN-AdML plasmid DNA was isolated from *E. coli* using the Triton-lysozyme method. Plasmid DNA was banded twice in CsCl-ethidium bromide density gradients, precipitated with ethanol, and dissolved in TE buffer (20 mM Tris-HCl, pH 7.6, 1 mM EDTA). A restriction fragment prepared by digestion of pDN-AdML DNA with EcoRI and NdeI was used as the template in transcription reactions. The fragment was purified from a 1.0% low melting temperature agarose gel using GELASE™ (Epicentre Technologies) according to the manufacturer's instructions. After phenol-chloroform extraction and ethanol precipitation, purified DNA fragments were resuspended in TE buffer.

Example 11

Preparation of RNA Polymerase II and Transcription Factors

RNA Polymerase II and TFIIH (rat δ, TSK DEAE 5-PW fraction) were purified as previously described from rat liver nuclear extracts. Recombinant yeast TBP and rat TFIIB (rat δ) were expressed in E. coli and purified as previously described. Recombinant TFIIE was prepared as previously described, except that the 56-kDa subunit was expressed in BL21(DE3)-pLysS. Recombinant TFIIF was purified as previously described from E. coli strain JM109(DE3) infected with M13mpET-RAP30 and M13mpET-RAP74.

Example 12

Runoff Transcription Assays

All reaction mixtures were 60 µl. Preinitiation complexes were assembled by preincubation of approximately 10 ng template DNA (EcoRI to NdeI fragment from pDN-AdML), ~10 ng of recombinant TFIIB, ~10 ng of recombinant TFIIF, ~7 ng of recombinant TFIIE, ~40 ng of rat TFIIH, ~20 ng of TBP, ~0.01 unit of RNA Polymerase II, and ~8 units of RNAsin in 20 mM Hepes-NaOH (pH 7.9), 20 mM Tris-HCl (pH 7.9), 60 mM KCl, 2 mM DTT, 0.5 mg/ml bovine serum albumin, 2% (w/v) polyvinyl alcohol, and 3% (v/v) glycerol for 30 min at 28° C. Elongin, Elongin subassemblies, or Elongin subunits were then added to reaction mixtures in the amounts and at the times indicated in the figure legends. Transcription was initiated by addition of 7 mM $MgCl_2$ and 50 µM ATP, 50 µM GTP, 10 µM CTP, 2 µM UTP and 10 µCi [α-$^{32}$P] CTP. After incubation of reaction mixtures for 9 min at 28° C., runoff transcripts were analyzed by electrophoresis through 6% polyacrylamide gels containing 7.0M urea. Transcription was quantitated using a Molecular Dynamics PHOSPHOIMAGER™.

Example 13

Construction of Elongin C Mutants

Elongin C mutants were constructed by oligonucleotide-directed mutagenesis of M13mpET-Elongin C with the MUTA-GENE® M13 in vitro mutagenesis kit (Bio-Rad, Herculer, Ga.) and confirmed by dideoxy DNA sequencing with the fmol DNA Sequencing System (Promega). Mutagenic oligonucleotides included 15 nucleotides from the parental rat Elongin C sequence on either side of the deletion point. Mutagenic oligonucleotides for alanine scanning mutagenesis included 12 nucleotides from the parental rat Elongin C on either side of the alanine substitution point.

Example 14

Expression and Purification of Elongin Subunits

Histidine-tagged Elongin A was overexpressed in E. coli using a pET16b expression vector (Novagen). The pET16b-Elongin A construct for expression of histidine-tagged Elongin A was prepared by insertion of a PCR-generated fragment containing the entire rat Elongin A open reading frame into the NdeI and BamHI sites of the pET-16b vector. A 1L culture of E. coli strain BL21(DE3) transformed with pET16b-Elongin A was grown to an $OD_{600}$ of 0.6 in Luria broth (LB) containing 100 µg/ml carbenicillin at 37° C. Following induction with 0.5 mM IPTG, the culture was incubated for an additional 3 hours at 37° C. Cells were harvested by centrifugation at 2000×g for 10 min at 4° C. The cell pellet was resuspended in 50 ml of ice-cold 20 mM Tris-HCl (pH 8.0), 10 mM imidazole (pH 8.0), and 1 mg/ml lysozyme and incubated on ice for 30 min. After 2 cycles of freeze-thaw, the suspension was centrifuged at 100,000×g for 35 min. Inclusion bodies were solubilized by resuspension in 50 ml of ice-cold 6M guanidine hydrochloride, 40 mM Tris-HCl (pH 8.0), 10 mM imidazole (pH 8.0), 0.5 mM PMSF, and 0.5M KCl, and the resulting suspension was clarified by centrifugation at 100,000×g for 35 min.

Recombinant Elongin A was purified from the supernatants by $Ni^{2+}$-nitrilotriacetic acid-agarose (Invitrogen) affinity chromatography. $Ni^{2+}$ chromatography was performed at 4° C. 10 ml of supernatant was applied to a 2 ml $Ni^{2+}$-column pre-equilibrated with 6M guanidine hydrochloride, 20 mM Tris-HCl (pH 7.9), 10 mM imidazole (pH 8.0), 0.5M KCl, and 0.5 mM PMSF. The column was washed with 10 ml of 5.7M guanidine hydrochloride, 40 mM Tris-HCl (pH 7.9), 40 mM imidazole (pH 8.0), and 0.5 mM PMSF, and recombinant Elongin A was eluted with 4.2M guanidine hydrochloride, 40 mM Tris-HCl (pH 7.9), 300 mM imidazole (pH 8.0), and 0.5 mM PMSF.

Overexpression of Elongin B and wild type and mutant Elongin C was accomplished using the M13mpET bacteriophage expression system. A 100 ml culture of E. coli strain JM109 (DE3) (Promega) was grown to an $OD_{600}$ of 0.6 in Luria broth at 37° C. Cells were infected with M13pET bacteriophage carrying the wild type rat Elongin B or wild type or mutant rat Elongin C cDNAs at a multiplicity of infection of 10–20. After an additional 2 hours at 37° C., cells were induced with 0.5 mM IPTG, and cultures were incubated an additional 3 hours. Cells were harvested by centrifugation at 2000×g for 10 min at 4° C. The cell pellet was resuspended in 7 ml of 20 mM Tris-HCl (pH 8.0), 10 mM imidazole (pH 8.0), and 1 mg/ml lysozyme and incubated on ice for 30 min. After 2 cycles of freeze-thaw, the suspension was centrifuged at 100,000×g for 35 min. Inclusion bodies were solubilized by resuspension in 7 ml of ice-cold 6M guanidine hydrochloride, 40 mM Tris-HCl (pH 8.0), 10 mM imidazole (pH 8.0), 0.5 mM PMSF, and 0.5M KCl, and the resulting suspension was clarified by centrifugation at 100,000×g for 35 min. Wild type Elongin B and wild type and mutant Elongin C were purified using $Ni^{2+}$-column chromatography as described above.

Example 15

Assay of Elongin BC Complex Formation

~6 µg of Elongin B was mixed with ~6 µg of either wild type or mutant Elongin C and diluted 5-fold with 40 mM Hepes-NaOH (pH 7.9), 100 mM KCl, 2 mM DTT, 50 µM $ZnSO_4$, 0.1 mM EDTA, and 10% (v/v) glycerol. After incubation for 90 min on ice, the mixtures were dialyzed at 4° C. overnight against 40 mM Tris-HCl (pH 7.9), 0.1 mM EDTA, 10% (v/v) glycerol, and 40 mM KCl. Following dialysis, the mixtures were centrifuged at 60,000×g for 15 min at 4° C. The resulting supernatants were applied to TSK DEAE-NPR columns (35 mm×4.6 mm, Toso-Haas) pre-equilibrated in 40 mM Tris-HCl (pH 7.9), 0.1 mM EDTA, 1 mM DTT, 10% (v/v) glycerol, and 40 mM KCl and fractionated using a SMART microchromatography system (Pharmacia) at 8° C. The columns were eluted at 0.3 ml/min with a 3 ml linear gradient from 0.04 to 0.5M KCl in 40 mM Tris-HCl (pH 7.9), 0.1 mM EDTA, 1 mM DTT, and 10% (v/v) glycerol. Aliquots of each column fraction were analyzed by 10% Tris-Tricine SDS-polyacrylamide gel electrophoresis, and the proteins were visualized by silver staining.

Example 16

Assay of Elongin ABC Complex Formation

~45 µg of Elongin A, ~6 µg of Elongin B, and ~6 µg of either wild type or mutant Elongin C were diluted 5-fold with 40 mM Hepes-NaOH (pH 7.9), 100 mM KCl, 50 µm ZnSO₄, and 10% (v/v) glycerol. After incubation for 90 min on ice, the mixtures were dialyzed at 4° C. overnight against 40 mM Tris-HCl (pH 7.9), 0.1 mM EDTA, 10% (v/v) glycerol, and 40 mM KCl. Following dialysis, the mixtures were centrifuged at 60,000×g for 15. min at 4° C. The resulting supernatants were applied to TSK SP-NPR columns (35 mm×4.6 mm, Toso-Haas) pre-equilibrated in 40 mM Hepes-NaOH (pH 7.9), 1 mM DTT, 10% (v/v) glycerol, and 0.1M KCl and fractionated using a SMART microchromatography system (Pharmacia) at 8° C. The columns were eluted at 0.6 ml/min with a 9 ml linear gradient from 0.1 to 0.8M KCl in 40 mM Hepes-NaOH (pH 7.9), 1 mM DTT, and 10% (v/v) glycerol. Aliquots of each column fraction were analyzed by 10% Tris-Tricine SDS-polyacrylamide gel electrophoresis, and the proteins were visualized by silver staining.

We claim:

1. A transcription regulation peptide which is a fragment of Elongin A wherein said fragment binds to Elongin B and Elongin C to form Elongin ABC complexes, and to stimulate the elongation activity of RNA Polymerase II.

2. The transcription regulation peptide of claim 1 wherein said peptide comprises an amino acid sequence as depicted in SEQ ID NO:2.

3. The transcription regulation peptide of claim 1 wherein said peptide comprises an amino acid sequence as depicted in SEQ ID NO:3.

4. The transcription regulation peptide of claim 1 wherein said peptide comprises an amino acid sequence as depicted in SEQ ID NO:4.

5. The transcription regulation peptide of claim 1 wherein said peptide comprises an amino acid sequence as depicted in SEQ ID NO:5.

6. The transcription regulation peptide of claim 1 wherein said peptide comprises an amino acid sequence as depicted in SEQ ID NO:6.

7. The transcription regulation peptide of claim 1 comprising an amino acid sequence as depicted in SEQ ID NO:42.

8. A transcription regulation peptide wherein said transcription regulation peptide consisting of an amino acid sequence as depicted in SEQ ID NO:16.

9. A transcription regulation peptide wherein said peptide comprises an amino acid sequence as depicted in SEQ ID NO:17.

10. A transcription regulation peptide which is a fragment of Elongin C wherein said fragment binds to Elongin A and/or Elongin B to activate Elongin A transcriptional activity, and to interact with Elongin B to form an Elongin BC complex.

11. The transcription regulation peptide of claim 10 wherein said peptide comprises an amino acid sequence as depicted in SEQ ID NO:46.

12. The transcription regulation peptide of claim 10 wherein said peptide comprises an amino acid sequence as depicted in SEQ ID NO:47.

13. A transcription regulation peptide wherein said peptide comprises an amino acid sequence selected from the group consisting of SEQ ID NO:10, SEQ ID NO:12 and SEQ ID NO:13.

* * * * *

UNITED STATES PATENT AND TRADEMARK OFFICE
CERTIFICATE OF CORRECTION

PATENT NO : 6,084,068
DATED : July 4, 2000
INVENTOR(S): Ronald C. Conaway, et al.

It is certified that error appears in the above-identified patent and that said Letters Patent is hereby corrected as shown below:

Column 4, line 33, after "(SEQ ID NO:78" insert ")".

Column 6, line 64, change " ~10°C" to "-10°C".

Column 10, line 26, change "Δ611.650" to "Δ611-650".

Column 12, line 47, change "SIi-like" to "SII-like".

Column 14, line 34, change "Elongin mutants C(Acanning mutants" to "Elongin C alanine scanning mutants".

Column 17, line 29, change "Piscata way" to "Piscataway".

Column 18, line 67, change "Gerrett" to "Garrett".

Column 19, line 4 , change "C.elegans" to "*C.elegans*".

Column 20, line 38, change "Rockfrod" to "Rockford".

Column 21, line 39, change "Herculer, Ga." to "Hercules, CA".

Signed and Sealed this

Eighth Day of May, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO. : 6,084,068
DATED : July 4, 2000
INVENTOR(S) : Ronald C. Conaway and Joan W. Conaway It is certified that error appears in the above-identified patent and that said Letters Patent is hereby corrected as shown below:

<u>Column 1,</u>
Line 3, insert the following:

--                 GOVERNMENT RIGHTS
      The invention described herein was supported, in part, by funding from the National Institutes of Health (Grant/Contract No. NIH GM41628). The U.S. Government has certain rights in this invention. --

Signed and Sealed this

Twenty-fourth Day of August, 2004

JON W. DUDAS
*Director of the United States Patent and Trademark Office*

SEQUENCE LISTING (1) GENERAL INFORMATION:

(iii) NUMBER OF SEQUENCES: 79

(2) INFORMATION FOR SEQ ID NO:1:

(i) SEQUENCE CHARACTERISTICS:
      (A) LENGTH: 773 amino acids
      (B) TYPE: amino acid
      (C) STRANDEDNESS: Not Relevant
      (D) TOPOLOGY: Not Relevant (ii) MOLECULE TYPE: protein (ix) FEATURE:
      (A) NAME/KEY: Protein
      (B) LOCATION: 1..773
      (D) OTHER INFORMATION: /note= "entire amino acid sequence
         of Elongin A"

(xi) SEQUENCE DESCRIPTION: SEQ ID NO:1:

```
Met Ala Ala Glu Ser Ala Leu Gln Val Val Glu Lys Leu Gln Ala Arg
 1               5                  10                  15

Leu Ala Ala Asn Pro Asp Pro Lys Lys Leu Leu Lys Tyr Leu Lys Lys
             20                  25                  30

Leu Ser Val Leu Pro Ile Thr Val Asp Ile Leu Val Glu Thr Gly Val
         35                  40                  45

Gly Lys Thr Val Asn Ser Phe Arg Lys His Glu Gln Val Gly Asn Phe
     50                  55                  60

Ala Arg Asp Leu Val Ala Gln Trp Lys Lys Leu Val Pro Val Glu Arg
65                  70                  75                  80

Asn Asn Glu Ala Glu Asp Gln Asp Phe Glu Lys Ser Asn Ser Arg Lys
                 85                  90                  95

Arg Pro Arg Asp Val Pro Gln Gln Glu Glu Ala Glu Gly Asn Tyr
            100                 105                 110

Gln Glu Ser Trp Gln Ala Ser Gly Ser Gln Pro Tyr Ser Pro Glu His
        115                 120                 125

Arg Gln Lys Lys His Arg Lys Leu Pro Glu Leu Glu Arg Pro His Lys
    130                 135                 140

Val Ala His Gly His Glu Arg Arg Asp Glu Arg Lys Arg Cys His Lys
145                 150                 155                 160

Val Ser Pro Pro Tyr Ser Ser Asp Pro Glu Ser Ser Asp Tyr Gly His
                165                 170                 175

Val Gln Ser Pro Pro Ser Ser Pro His Gln Met Tyr Thr Asp Leu
            180                 185                 190

Ser Arg Ser Pro Glu Met Asp Gln Glu Pro Ile Val Ser His Pro Lys
        195                 200                 205

Pro Gly Lys Val His Ser Asn Thr Phe Gln Asp Arg Leu Gly Val Ser
    210                 215                 220
```

-continued

```
His Leu Gly Glu His Gln Gly Lys Gly Ala Val Ser Gln Asn Lys Pro
225                 230                 235                 240

His Lys Ser Ser His Lys Glu Lys Arg Pro Val Asp Ala Arg Gly Asp
            245                 250                 255

Glu Lys Ser Ser Val Met Gly Arg Glu Lys Ser His Lys Ala Ser Ser
        260                 265                 270

Lys Glu Glu Ser Arg Arg Leu Leu Ser Glu Asp Ser Ala Lys Glu Lys
    275                 280                 285

Leu Pro Ser Ser Val Val Lys Lys Glu Lys Asp Arg Glu Gly Asn Ser
290                 295                 300

Leu Lys Lys Lys Leu Ser Pro Ala Leu Asp Val Ala Ser Asp Asn His
305                 310                 315                 320

Phe Lys Lys Pro Lys His Lys Asp Ser Glu Lys Ile Lys Ser Asp Lys
            325                 330                 335

Asn Lys Gln Ser Val Asp Ser Val Asp Ser Gly Arg Gly Thr Gly Asp
        340                 345                 350

Pro Leu Pro Arg Ala Lys Asp Lys Val Pro Asn Asn Leu Lys Ala Gln
    355                 360                 365

Glu Gly Lys Val Arg Thr Asn Ser Asp Arg Lys Ser Pro Gly Ser Leu
370                 375                 380

Pro Lys Val Glu Glu Met Asp Met Asp Glu Phe Glu Gln Pro Thr
385                 390                 395                 400

Met Ser Phe Glu Ser Tyr Leu Ser Tyr Asp Gln Pro Arg Lys Lys Lys
            405                 410                 415

Lys Lys Val Val Lys Thr Ser Gly Thr Ala Leu Gly Leu Lys Gly Leu
        420                 425                 430

Lys Lys Lys Asp Ser Lys Ser Thr Ser Lys Asn Leu Asn Ser Ala Gln
    435                 440                 445

Lys Leu Pro Lys Ala Asn Glu Asn Lys Ser Asp Lys Leu Gln Pro Ala
450                 455                 460

Gly Ala Glu Pro Thr Arg Pro Arg Lys Val Pro Thr Asp Val Leu Pro
465                 470                 475                 480

Ala Leu Pro Asp Ile Pro Leu Pro Ala Ile Gln Thr Asn Tyr Arg Pro
            485                 490                 495

Leu Pro Ser Leu Glu Leu Ile Ser Ser Phe Gln Pro Lys Arg Lys Ala
        500                 505                 510

Phe Ser Ser Pro Gln Glu Glu Glu Ala Gly Phe Thr Gly Arg Arg
    515                 520                 525

Met Asn Ser Lys Met Gln Val Tyr Ser Gly Ser Lys Cys Ala Tyr Leu
530                 535                 540

Pro Lys Met Met Thr Leu His Gln Gln Cys Ile Arg Val Leu Lys Asn
545                 550                 555                 560

Asn Ile Asp Ser Ile Phe Glu Val Gly Gly Val Pro Tyr Ser Val Leu
            565                 570                 575

Glu Pro Val Leu Glu Arg Cys Thr Pro Asp Gln Leu Tyr Arg Ile Glu
        580                 585                 590

Glu Cys Asn His Val Leu Ile Glu Glu Thr Asp Gln Leu Trp Lys Val
    595                 600                 605

His Cys His Arg Asp Phe Lys Glu Glu Arg Pro Glu Glu Tyr Glu Ser
610                 615                 620

Trp Arg Glu Met Tyr Leu Arg Leu Gln Asp Ala Arg Glu Gln Arg Leu
625                 630                 635                 640
```

-continued

```
Arg Leu Leu Thr Asn Asn Ile Arg Ser Ala His Ala Asn Lys Pro Lys
                645                 650                 655

Gly Arg Gln Ala Lys Met Ala Phe Val Asn Ser Val Ala Lys Pro Pro
            660                 665                 670

Arg Asp Val Arg Arg Gln Glu Lys Phe Gly Thr Gly Gly Ala Ala
        675                 680                 685

Val Pro Glu Lys Val Arg Ile Lys Pro Ala Pro Tyr Thr Thr Gly Ser
    690                 695                 700

Ser His Val Pro Ala Ser Asn Ser Ser Ser Phe His Ser Ser Pro
705                 710                 715                 720

Glu Glu Leu Ala Tyr Glu Gly Pro Ser Thr Ser Ser Ala His Leu Ala
                725                 730                 735

Pro Val Ala Ser Ser Val Ser Tyr Asp Pro Arg Lys Pro Ala Val
            740                 745                 750

Lys Lys Ile Ala Pro Met Met Ala Lys Thr Ile Lys Ala Phe Lys Asn
        755                 760                 765

Arg Phe Ser Arg Arg
    770
```

(2) INFORMATION FOR SEQ ID NO:2:

(i) SEQUENCE CHARACTERISTICS:
      (A) LENGTH: 730 amino acids
      (B) TYPE: amino acid
      (C) STRANDEDNESS: Not Relevant
      (D) TOPOLOGY: Not Relevant (ii) MOLECULE TYPE: peptide (ix) FEATURE:
      (A) NAME/KEY: Peptide
      (B) LOCATION: 1..730
      (D) OTHER INFORMATION: /note= "amino acids 1-730 of
          Elongin A"

(xi) SEQUENCE DESCRIPTION: SEQ ID NO:2:

```
Met Ala Ala Glu Ser Ala Leu Gln Val Val Glu Lys Leu Gln Ala Arg
1               5                   10                  15

Leu Ala Ala Asn Pro Asp Pro Lys Lys Leu Leu Lys Tyr Leu Lys Lys
                20                  25                  30

Leu Ser Val Leu Pro Ile Thr Val Asp Ile Leu Val Glu Thr Gly Val
            35                  40                  45

Gly Lys Thr Val Asn Ser Phe Arg Lys His Glu Gln Val Gly Asn Phe
        50                  55                  60

Ala Arg Asp Leu Val Ala Gln Trp Lys Lys Leu Val Pro Val Glu Arg
65                  70                  75                  80

Asn Asn Glu Ala Glu Asp Gln Asp Phe Glu Lys Ser Asn Ser Arg Lys
                85                  90                  95

Arg Pro Arg Asp Val Pro Gln Glu Glu Ala Glu Gly Asn Tyr
            100                 105                 110

Gln Glu Ser Trp Gln Ala Ser Gly Ser Gln Pro Tyr Ser Pro Glu His
        115                 120                 125

Arg Gln Lys Lys His Arg Lys Leu Pro Glu Leu Glu Arg Pro His Lys
    130                 135                 140

Val Ala His Gly His Glu Arg Arg Asp Glu Arg Lys Arg Cys His Lys
145                 150                 155                 160

Val Ser Pro Pro Tyr Ser Ser Asp Pro Glu Ser Ser Asp Tyr Gly His
                165                 170                 175
```

-continued

```
Val Gln Ser Pro Pro Ser Pro His Gln Met Tyr Thr Asp Leu
        180             185             190

Ser Arg Ser Pro Glu Met Asp Gln Glu Pro Ile Val Ser His Pro Lys
        195             200             205

Pro Gly Lys Val His Ser Asn Thr Phe Gln Asp Arg Leu Gly Val Ser
        210             215             220

His Leu Gly Glu His Gln Gly Lys Gly Ala Val Ser Gln Asn Lys Pro
225             230             235             240

His Lys Ser Ser His Lys Glu Lys Arg Pro Val Asp Ala Arg Gly Asp
                245             250             255

Glu Lys Ser Ser Val Met Gly Arg Glu Lys Ser His Lys Ala Ser Ser
                260             265             270

Lys Glu Glu Ser Arg Arg Leu Leu Ser Glu Asp Ser Ala Lys Glu Lys
        275             280             285

Leu Pro Ser Ser Val Val Lys Lys Glu Lys Asp Arg Glu Gly Asn Ser
        290             295             300

Leu Lys Lys Lys Leu Ser Pro Ala Leu Asp Val Ala Ser Asp Asn His
305             310             315             320

Phe Lys Lys Pro Lys His Lys Asp Ser Glu Lys Ile Lys Ser Asp Lys
                325             330             335

Asn Lys Gln Ser Val Asp Ser Val Asp Ser Gly Arg Gly Thr Gly Asp
                340             345             350

Pro Leu Pro Arg Ala Lys Asp Lys Val Pro Asn Asn Leu Lys Ala Gln
        355             360             365

Glu Gly Lys Val Arg Thr Asn Ser Asp Arg Lys Ser Pro Gly Ser Leu
        370             375             380

Pro Lys Val Glu Glu Met Asp Met Asp Glu Phe Glu Gln Pro Thr
385             390             395             400

Met Ser Phe Glu Ser Tyr Leu Ser Tyr Asp Gln Pro Arg Lys Lys Lys
                405             410             415

Lys Lys Val Val Lys Thr Ser Gly Thr Ala Leu Gly Leu Lys Gly Leu
                420             425             430

Lys Lys Lys Asp Ser Lys Ser Thr Ser Lys Asn Leu Asn Ser Ala Gln
        435             440             445

Lys Leu Pro Lys Ala Asn Glu Asn Lys Ser Asp Lys Leu Gln Pro Ala
        450             455             460

Gly Ala Glu Pro Thr Arg Pro Arg Lys Val Pro Thr Asp Val Leu Pro
465             470             475             480

Ala Leu Pro Asp Ile Pro Leu Pro Ala Ile Gln Thr Asn Tyr Arg Pro
                485             490             495

Leu Pro Ser Leu Glu Leu Ile Ser Ser Phe Gln Pro Lys Arg Lys Ala
        500             505             510

Phe Ser Ser Pro Gln Glu Glu Glu Ala Gly Phe Thr Gly Arg Arg
        515             520             525

Met Asn Ser Lys Met Gln Val Tyr Ser Gly Ser Lys Cys Ala Tyr Leu
        530             535             540

Pro Lys Met Met Thr Leu His Gln Gln Cys Ile Arg Val Leu Lys Asn
545             550             555             560

Asn Ile Asp Ser Ile Phe Glu Val Gly Gly Val Pro Tyr Ser Val Leu
                565             570             575

Glu Pro Val Leu Glu Arg Cys Thr Pro Asp Gln Leu Tyr Arg Ile Glu
        580             585             590

Glu Cys Asn His Val Leu Ile Glu Glu Thr Asp Gln Leu Trp Lys Val
```

-continued

```
                595                 600                      605
    His Cys His Arg Asp Phe Lys Glu Glu Arg Pro Glu Glu Tyr Glu Ser
        610             615                 620
    Trp Arg Glu Met Tyr Leu Arg Leu Gln Asp Ala Arg Glu Gln Arg Leu
    625             630                 635                 640
    Arg Leu Leu Thr Asn Asn Ile Arg Ser Ala His Ala Asn Lys Pro Lys
                645                 650                 655
    Gly Arg Gln Ala Lys Met Ala Phe Val Asn Ser Val Ala Lys Pro Pro
                660                 665                 670
    Arg Asp Val Arg Arg Gln Glu Lys Phe Gly Thr Gly Gly Ala Ala
                675                 680                 685
    Val Pro Glu Lys Val Arg Ile Lys Pro Ala Pro Tyr Thr Thr Gly Ser
        690                 695                 700
    Ser His Val Pro Ala Ser Asn Ser Ser Ser Ser Phe His Ser Ser Pro
    705                 710                 715                 720
    Glu Glu Leu Ala Tyr Glu Gly Pro Ser Thr
                        725                 730
```

(2) INFORMATION FOR SEQ ID NO:3:

(i) SEQUENCE CHARACTERISTICS:
        (A) LENGTH: 680 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..680
        (D) OTHER INFORMATION: /note= "amino acids 1-680 of
            Elongin A"

(xi) SEQUENCE DESCRIPTION: SEQ ID NO:3:

```
    Met Ala Ala Glu Ser Ala Leu Gln Val Val Glu Lys Leu Gln Ala Arg
    1               5                   10                  15
    Leu Ala Ala Asn Pro Asp Pro Lys Lys Leu Leu Lys Tyr Leu Lys Lys
                20                  25                  30
    Leu Ser Val Leu Pro Ile Thr Val Asp Ile Leu Val Glu Thr Gly Val
                35                  40                  45
    Gly Lys Thr Val Asn Ser Phe Arg Lys His Glu Gln Val Gly Asn Phe
            50                  55                  60
    Ala Arg Asp Leu Val Ala Gln Trp Lys Lys Leu Val Pro Val Glu Arg
    65                  70                  75                  80
    Asn Asn Glu Ala Glu Asp Gln Asp Phe Glu Lys Ser Asn Ser Arg Lys
                    85                  90                  95
    Arg Pro Arg Asp Val Pro Gln Gln Glu Glu Ala Glu Gly Asn Tyr
                100                 105                 110
    Gln Glu Ser Trp Gln Ala Ser Gly Ser Gln Pro Tyr Ser Pro Glu His
                115                 120                 125
    Arg Gln Lys Lys His Arg Lys Leu Pro Glu Leu Glu Arg Pro His Lys
            130                 135                 140
    Val Ala His Gly His Glu Arg Arg Asp Glu Arg Lys Arg Cys His Lys
    145                 150                 155                 160
    Val Ser Pro Pro Tyr Ser Ser Asp Pro Glu Ser Ser Asp Tyr Gly His
                    165                 170                 175
    Val Gln Ser Pro Pro Pro Ser Ser Pro His Gln Met Tyr Thr Asp Leu
```

-continued

```
                180             185             190
Ser Arg Ser Pro Glu Met Asp Gln Glu Pro Ile Val Ser His Pro Lys
            195             200             205
Pro Gly Lys Val His Ser Asn Thr Phe Gln Asp Arg Leu Gly Val Ser
            210             215             220
His Leu Gly Glu His Gln Gly Lys Gly Ala Val Ser Gln Asn Lys Pro
225             230             235             240
His Lys Ser Ser His Lys Glu Lys Arg Pro Val Asp Ala Arg Gly Asp
            245             250             255
Glu Lys Ser Ser Val Met Gly Arg Glu Lys Ser His Lys Ala Ser Ser
            260             265             270
Lys Glu Glu Ser Arg Arg Leu Leu Ser Glu Asp Ser Ala Lys Glu Lys
            275             280             285
Leu Pro Ser Ser Val Val Lys Lys Glu Lys Asp Arg Glu Gly Asn Ser
            290             295             300
Leu Lys Lys Lys Leu Ser Pro Ala Leu Asp Val Ala Ser Asp Asn His
305             310             315             320
Phe Lys Lys Pro Lys His Lys Asp Ser Glu Lys Ile Lys Ser Asp Lys
            325             330             335
Asn Lys Gln Ser Val Asp Ser Val Asp Ser Gly Arg Gly Thr Gly Asp
            340             345             350
Pro Leu Pro Arg Ala Lys Asp Lys Val Pro Asn Asn Leu Lys Ala Gln
            355             360             365
Glu Gly Lys Val Arg Thr Asn Ser Asp Arg Lys Ser Pro Gly Ser Leu
            370             375             380
Pro Lys Val Glu Glu Met Asp Met Asp Asp Glu Phe Glu Gln Pro Thr
385             390             395             400
Met Ser Phe Glu Ser Tyr Leu Ser Tyr Asp Gln Pro Arg Lys Lys Lys
            405             410             415
Lys Lys Val Val Lys Thr Ser Gly Thr Ala Leu Gly Glu Lys Gly Leu
            420             425             430
Lys Lys Lys Asp Ser Lys Ser Thr Ser Lys Asn Leu Asn Ser Ala Gln
            435             440             445
Lys Leu Pro Lys Ala Asn Glu Asn Lys Ser Asp Lys Leu Gln Pro Ala
            450             455             460
Gly Ala Glu Pro Thr Arg Pro Arg Lys Val Pro Thr Asp Val Leu Pro
465             470             475             480
Ala Leu Pro Asp Ile Pro Leu Pro Ala Ile Gln Thr Asn Tyr Arg Pro
            485             490             495
Leu Pro Ser Leu Glu Leu Ile Ser Ser Phe Gln Pro Lys Arg Lys Ala
            500             505             510
Phe Ser Ser Pro Gln Glu Glu Glu Ala Gly Phe Thr Gly Arg Arg
            515             520             525
Met Asn Ser Lys Met Gln Val Tyr Ser Gly Ser Lys Cys Ala Tyr Leu
530             535             540
Pro Lys Met Met Thr Leu His Gln Gln Cys Ile Arg Val Leu Lys Asn
545             550             555             560
Asn Ile Asp Ser Ile Phe Glu Val Gly Gly Val Pro Tyr Ser Val Leu
            565             570             575
Glu Pro Val Leu Glu Arg Cys Thr Pro Asp Gln Leu Tyr Arg Ile Glu
            580             585             590
Glu Cys Asn His Val Leu Ile Glu Glu Thr Asp Gln Leu Trp Lys Val
            595             600             605
```

```
            His Cys His Arg Asp Phe Lys Glu Glu Arg Pro Glu Glu Tyr Glu Ser
                610                 615                 620

Trp Arg Glu Met Tyr Leu Arg Leu Gln Asp Ala Arg Glu Gln Arg Leu
            625                 630                 635                 640

Arg Leu Leu Thr Asn Asn Ile Arg Ser Ala His Ala Asn Lys Pro Lys
                            645                 650                 655

Gly Arg Gln Ala Lys Met Ala Phe Val Asn Ser Val Ala Lys Pro Pro
                            660                 665                 670

Arg Asp Val Arg Arg Arg Gln Glu
                        675                 680

(2) INFORMATION FOR SEQ ID NO:4:

(i) SEQUENCE CHARACTERISTICS:
        (A) LENGTH: 374 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..374
        (D) OTHER INFORMATION: /note= "amino acids 400-773 of
            Elongin A"

(xi) SEQUENCE DESCRIPTION: SEQ ID NO:4:

Thr Met Ser Phe Glu Ser Tyr Leu Ser Tyr Asp Gln Pro Arg Lys Lys
            1               5                  10                  15

Lys Lys Lys Val Val Lys Thr Ser Gly Thr Ala Leu Gly Glu Lys Gly
                            20                  25                  30

Leu Lys Lys Lys Asp Ser Lys Ser Thr Ser Lys Asn Leu Asn Ser Ala
                        35                  40                  45

Gln Lys Leu Pro Lys Ala Asn Glu Asn Lys Ser Asp Lys Leu Gln Pro
                    50                  55                  60

Ala Gly Ala Glu Pro Thr Arg Pro Arg Lys Val Pro Thr Asp Val Leu
            65                  70                  75                  80

Pro Ala Leu Pro Asp Ile Pro Leu Pro Ala Ile Gln Thr Asn Tyr Arg
                            85                  90                  95

Pro Leu Pro Ser Leu Glu Leu Ile Ser Ser Phe Gln Pro Lys Arg Lys
                        100                 105                 110

Ala Phe Ser Ser Pro Gln Glu Glu Glu Ala Gly Phe Thr Gly Arg
                    115                 120                 125

Arg Met Asn Ser Lys Met Gln Val Tyr Ser Gly Ser Lys Cys Ala Tyr
                130                 135                 140

Leu Pro Lys Met Met Thr Leu His Gln Gln Cys Ile Arg Val Leu Lys
            145                 150                 155                 160

Asn Asn Ile Asp Ser Ile Phe Glu Val Gly Gly Val Pro Tyr Ser Val
                            165                 170                 175

Leu Glu Pro Val Leu Glu Arg Cys Thr Pro Asp Gln Leu Tyr Arg Ile
                        180                 185                 190

Glu Glu Cys Asn His Val Leu Ile Glu Glu Thr Asp Gln Leu Trp Lys
                    195                 200                 205

Val His Cys His Arg Asp Phe Lys Glu Glu Arg Pro Glu Glu Tyr Glu
                210                 215                 220

Ser Trp Arg Glu Met Tyr Leu Arg Leu Gln Asp Ala Arg Glu Gln Arg
            225                 230                 235                 240
```

```
Leu Arg Leu Leu Thr Asn Asn Ile Arg Ser Ala His Ala Asn Lys Pro
                245                 250                 255

Lys Gly Arg Gln Ala Lys Met Ala Phe Val Asn Ser Val Ala Lys Pro
            260                 265                 270

Pro Arg Asp Val Arg Arg Gln Glu Lys Phe Gly Thr Gly Gly Ala
        275                 280                 285

Ala Val Pro Glu Lys Val Arg Ile Lys Pro Ala Pro Tyr Thr Thr Gly
        290                 295                 300

Ser Ser His Val Pro Ala Ser Asn Ser Ser Ser Phe His Ser Ser
305                 310                 315                 320

Pro Glu Glu Leu Ala Tyr Glu Gly Pro Ser Thr Ser Ser Ala His Leu
                325                 330                 335

Ala Pro Val Ala Ser Ser Val Ser Tyr Asp Pro Arg Lys Pro Ala
                340                 345                 350

Val Lys Lys Ile Ala Pro Met Met Ala Lys Thr Ile Lys Ala Phe Lys
                355                 360                 365

Asn Arg Phe Ser Arg Arg
        370
```

(2) INFORMATION FOR SEQ ID NO:5:

(i) SEQUENCE CHARACTERISTICS:
        (A) LENGTH: 331 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..331
        (D) OTHER INFORMATION: /note= "amino acids 400-730 of
            Elongin A"

(xi) SEQUENCE DESCRIPTION: SEQ ID NO:5:

```
Thr Met Ser Phe Glu Ser Tyr Leu Ser Tyr Asp Gln Pro Arg Lys Lys
1               5                   10                  15

Lys Lys Lys Val Val Lys Thr Ser Gly Thr Ala Leu Gly Glu Lys Gly
            20                  25                  30

Leu Lys Lys Lys Asp Ser Lys Ser Thr Ser Lys Asn Leu Asn Ser Ala
            35                  40                  45

Gln Lys Leu Pro Lys Ala Asn Glu Asn Lys Ser Asp Lys Leu Gln Pro
        50                  55                  60

Ala Gly Ala Glu Pro Thr Arg Pro Arg Lys Val Pro Thr Asp Val Leu
65                  70                  75                  80

Pro Ala Leu Pro Asp Ile Pro Leu Pro Ala Ile Gln Thr Asn Tyr Arg
                85                  90                  95

Pro Leu Pro Ser Leu Glu Leu Ile Ser Ser Phe Gln Pro Lys Arg Lys
                100                 105                 110

Ala Phe Ser Ser Pro Gln Glu Glu Glu Ala Gly Phe Thr Gly Arg
                115                 120                 125

Arg Met Asn Ser Lys Met Gln Val Tyr Ser Gly Ser Lys Cys Ala Tyr
        130                 135                 140

Leu Pro Lys Met Met Thr Leu His Gln Gln Cys Ile Arg Val Leu Lys
145                 150                 155                 160

Asn Asn Ile Asp Ser Ile Phe Glu Val Gly Val Pro Tyr Ser Val
                165                 170                 175
```

```
           Leu Glu Pro Val Leu Glu Arg Cys Thr Pro Asp Gln Leu Tyr Arg Ile
                       180                 185                 190

Glu Glu Cys Asn His Val Leu Ile Glu Glu Thr Asp Gln Leu Trp Lys
                   195                 200                 205

Val His Cys His Arg Asp Phe Lys Glu Glu Arg Pro Glu Glu Tyr Glu
                   210                 215                 220

Ser Trp Arg Glu Met Tyr Leu Arg Leu Gln Asp Ala Arg Glu Gln Arg
           225                 230                 235                 240

Leu Arg Leu Leu Thr Asn Asn Ile Arg Ser Ala His Ala Asn Lys Pro
                           245                 250                 255

Lys Gly Arg Gln Ala Lys Met Ala Phe Val Asn Ser Val Ala Lys Pro
                       260                 265                 270

Pro Arg Asp Val Arg Arg Gln Glu Lys Phe Gly Thr Gly Gly Ala
                       275                 280                 285

Ala Val Pro Glu Lys Val Arg Ile Lys Pro Ala Pro Tyr Thr Thr Gly
                       290                 295                 300

Ser Ser His Val Pro Ala Ser Asn Ser Ser Ser Phe His Ser Ser
           305                 310                 315                 320

Pro Glu Glu Leu Ala Tyr Glu Gly Pro Ser Thr
                           325                 330

(2) INFORMATION FOR SEQ ID NO:6:

(i) SEQUENCE CHARACTERISTICS:
          (A) LENGTH: 281 amino acids
          (B) TYPE: amino acid
          (C) STRANDEDNESS: Not Relevant
          (D) TOPOLOGY: Not Relevant (ii) MOLECULE TYPE: peptide (ix) FEATURE:
          (A) NAME/KEY: Peptide
          (B) LOCATION: 1..281
          (D) OTHER INFORMATION: /note= "amino acids 400-680 of
              Elongin A"

(xi) SEQUENCE DESCRIPTION: SEQ ID NO:6:

Thr Met Ser Phe Glu Ser Tyr Leu Ser Tyr Asp Gln Pro Arg Lys Lys
           1               5                  10                  15

Lys Lys Lys Val Val Lys Thr Ser Gly Thr Ala Leu Gly Glu Lys Gly
                       20                  25                  30

Leu Lys Lys Lys Asp Ser Lys Ser Thr Ser Lys Asn Leu Asn Ser Ala
                       35                  40                  45

Gln Lys Leu Pro Lys Ala Asn Glu Asn Lys Ser Asp Lys Leu Gln Pro
                50                  55                  60

Ala Gly Ala Glu Pro Thr Arg Pro Arg Lys Val Pro Thr Asp Val Leu
           65                  70                  75                  80

Pro Ala Leu Pro Asp Ile Pro Leu Pro Ala Ile Gln Thr Asn Tyr Arg
                           85                  90                  95

Pro Leu Pro Ser Leu Glu Leu Ile Ser Ser Phe Gln Pro Lys Arg Lys
                       100                 105                 110

Ala Phe Ser Ser Pro Gln Glu Glu Glu Ala Gly Phe Thr Gly Arg
                       115                 120                 125

Arg Met Asn Ser Lys Met Gln Val Tyr Ser Gly Ser Lys Cys Ala Tyr
                       130                 135                 140

Leu Pro Lys Met Met Thr Leu His Gln Gln Cys Ile Arg Val Leu Lys
           145                 150                 155                 160
```

```
         Asn Asn Ile Asp Ser Ile Phe Glu Val Gly Val Pro Tyr Ser Val
                         165                 170                 175

Leu Glu Pro Val Leu Glu Arg Cys Thr Pro Asp Gln Leu Tyr Arg Ile
                     180                 185                 190

Glu Glu Cys Asn His Val Leu Ile Glu Glu Thr Asp Gln Leu Trp Lys
                     195                 200                 205

Val His Cys His Arg Asp Phe Lys Glu Glu Arg Pro Glu Glu Tyr Glu
                 210                 215                 220

Ser Trp Arg Glu Met Tyr Leu Arg Leu Gln Asp Ala Arg Glu Gln Arg
         225                 230                 235                 240

Leu Arg Leu Leu Thr Asn Asn Ile Arg Ser Ala His Ala Asn Lys Pro
                         245                 250                 255

Lys Gly Arg Gln Ala Lys Met Ala Phe Val Asn Ser Val Ala Lys Pro
                     260                 265                 270

Pro Arg Asp Val Arg Arg Arg Gln Glu
                     275                 280
```

(2) INFORMATION FOR SEQ ID NO:7:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..20
        (D) OTHER INFORMATION: /note= "amino acids 546-565 of
            Elongin A"

(xi) SEQUENCE DESCRIPTION: SEQ ID NO:7:

```
         Lys Met Met Thr Leu His Gln Gln Cys Ile Arg Val Leu Lys Asn Asn
         1               5                   10                  15

Ile Asp Ser Ile
                     20
```

(2) INFORMATION FOR SEQ ID NO:8:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..12
        (D) OTHER INFORMATION: /note= "amino acids 549-560 of
            Elongin A"

(xi) SEQUENCE DESCRIPTION: SEQ ID NO:8:

```
         Thr Leu His Gln Gln Cys Ile Arg Val Leu Lys Asn
         1               5                   10
```

(2) INFORMATION FOR SEQ ID NO:9:

(i) SEQUENCE CHARACTERISTICS:
        (A) LENGTH: 112 amino acids
        (B) TYPE: amino acid
        (C) STRANDEDNESS: Not Relevant (D) TOPOLOGY: Not Relevant (ii) MOLECULE TYPE: peptide (ix) FEATURE:
            (A) NAME/KEY: Protein
            (B) LOCATION: 1..112
            (D) OTHER INFORMATION: /note= "entire amino acid sequence
                of Elongin C"

(xi) SEQUENCE DESCRIPTION: SEQ ID NO:9:

Met Asp Gly Glu Glu Lys Thr Tyr Gly Gly Cys Glu Gly Pro Asp Ala
    1               5                   10                  15

Met Tyr Val Lys Leu Ile Ser Ser Asp Gly His Glu Phe Ile Val Lys
                    20                  25                  30

Arg Glu His Ala Leu Thr Ser Gly Thr Ile Lys Ala Met Leu Ser Gly
                35                  40                  45

Pro Gly Gln Phe Ala Glu Asn Glu Thr Asn Glu Val Asn Phe Arg Glu
        50                  55                  60

Ile Pro Ser His Val Leu Ser Lys Val Cys Met Tyr Phe Thr Tyr Lys
    65                  70                  75                  80

Val Arg Tyr Thr Asn Ser Ser Thr Glu Ile Pro Glu Phe Pro Ile Ala
                    85                  90                  95

Pro Glu Ile Ala Leu Glu Leu Leu Met Ala Ala Asn Phe Leu Asp Cys
                    100                 105                 110

(2) INFORMATION FOR SEQ ID NO:10:

(i) SEQUENCE CHARACTERISTICS:
            (A) LENGTH: 12 amino acids
            (B) TYPE: amino acid
            (C) STRANDEDNESS: Not Relevant
            (D) TOPOLOGY: Not Relevant (ii) MOLECULE TYPE: peptide (ix) FEATURE:
            (A) NAME/KEY: Peptide
            (B) LOCATION: 1..12
            (D) OTHER INFORMATION: /note= "amino acids 19-30 of
                Elongin C"

(xi) SEQUENCE DESCRIPTION: SEQ ID NO:10:

Val Lys Leu Ile Ser Ser Asp Gly His Glu Phe Ile
    1               5                   10

(2) INFORMATION FOR SEQ ID NO:11:

(i) SEQUENCE CHARACTERISTICS:
            (A) LENGTH: 13 amino acids
            (B) TYPE: amino acid
            (C) STRANDEDNESS: Not Relevant
            (D) TOPOLOGY: Not Relevant (ii) MOLECULE TYPE: peptide (ix) FEATURE:
            (A) NAME/KEY: Protein
            (B) LOCATION: 1..13
            (D) OTHER INFORMATION: /note= "amino acids 100-112 of
                Elongin C"

(xi) SEQUENCE DESCRIPTION: SEQ ID NO:11:

Ala Leu Glu Leu Leu Met Ala Ala Asn Phe Leu Asp Cys
    1               5                   10

(2) INFORMATION FOR SEQ ID NO:12:

```
    (i) SEQUENCE CHARACTERISTICS:
        (A) LENGTH: 12 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..12
        (D) OTHER INFORMATION: /note= "amino acids 60-71 of
            Elongin C"

(xi) SEQUENCE DESCRIPTION: SEQ ID NO:12:

Val Asn Phe Arg Glu Ile Pro Ser His Val Leu Ser
  1               5                  10

(2) INFORMATION FOR SEQ ID NO:13:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..22
        (D) OTHER INFORMATION: /note= "amino acids 91-112 of
            Elongin C"

(xi) SEQUENCE DESCRIPTION: SEQ ID NO:13:

Pro Glu Phe Pro Ile Ala Pro Glu Ile Ala Leu Glu Leu Leu Met Ala
  1               5                  10                  15

Ala Asn Phe Leu Asp Cys
                20

(2) INFORMATION FOR SEQ ID NO:14:

(i) SEQUENCE CHARACTERISTICS:
        (A) LENGTH: 171 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Peptide
        (B) LOCATION: 1..171
        (D) OTHER INFORMATION: /note= "amino acids 520-690 of
            Elongin A"

(xi) SEQUENCE DESCRIPTION: SEQ ID NO:14:

Glu Glu Ala Gly Phe Thr Gly Arg Arg Met Asn Ser Lys Met Gln Val
  1               5                  10                  15

Tyr Ser Gly Ser Lys Cys Ala Tyr Leu Pro Lys Met Met Thr Leu His
                20                  25                  30

Gln Gln Cys Ile Arg Val Leu Lys Asn Asn Ile Asp Ser Ile Phe Glu
                35                  40                  45

Val Gly Gly Val Pro Tyr Ser Val Leu Glu Pro Val Leu Glu Arg Cys
          50                  55                  60

Thr Pro Asp Gln Leu Tyr Arg Ile Glu Glu Cys Asn His Val Leu Ile
  65                  70                  75                  80
```

```
          Glu Glu Thr Asp Gln Leu Trp Lys Val His Cys His Arg Asp Phe Lys
                      85                  90                  95

Glu Glu Arg Pro Glu Glu Tyr Glu Ser Trp Arg Glu Met Tyr Leu Arg
                     100                 105                 110

Leu Gln Asp Ala Arg Glu Gln Arg Leu Arg Leu Leu Thr Asn Asn Ile
                     115                 120                 125

Arg Ser Ala His Ala Asn Lys Pro Lys Gly Arg Gln Ala Lys Met Ala
                 130                 135                 140

Phe Val Asn Ser Val Ala Lys Pro Pro Arg Asp Val Arg Arg Arg Gln
          145                 150                 155                 160

Glu Lys Phe Gly Thr Gly Gly Ala Ala Val Pro
                         165                 170
```

(2) INFORMATION FOR SEQ ID NO:15:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..16
        (D) OTHER INFORMATION: /note= "amino acids 157-172 of VHL
            protein"

(xi) SEQUENCE DESCRIPTION: SEQ ID NO:15:

```
          Thr Leu Lys Glu Arg Cys Leu Gln Val Val Arg Ser Leu Val Lys Pro
          1               5                  10                  15
```

(2) INFORMATION FOR SEQ ID NO:16:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..12
        (D) OTHER INFORMATION: /note= "consensus sequence"

(xi) SEQUENCE DESCRIPTION: SEQ ID NO:16:

```
          Thr Leu Xaa Xaa Xaa Cys Xaa Xaa Val Xaa Xaa Xaa
          1               5                  10
```

(2) INFORMATION FOR SEQ ID NO:17:

(i) SEQUENCE CHARACTERISTICS:
        (A) LENGTH: 630 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..630
        (D) OTHER INFORMATION: /note= "amino acids 1-630 of
            Elongin A"

(xi) SEQUENCE DESCRIPTION: SEQ ID NO:17:

-continued

```
Met Ala Ala Glu Ser Ala Leu Gln Val Val Glu Lys Leu Gln Ala Arg
1               5                   10                  15
Leu Ala Ala Asn Pro Asp Pro Lys Lys Leu Leu Lys Tyr Leu Lys Lys
            20                  25                  30
Leu Ser Val Leu Pro Ile Thr Val Asp Ile Leu Val Glu Thr Gly Val
        35                  40                  45
Gly Lys Thr Val Asn Ser Phe Arg Lys His Glu Gln Val Gly Asn Phe
    50                  55                  60
Ala Arg Asp Leu Val Ala Gln Trp Lys Lys Leu Val Pro Val Glu Arg
65                  70                  75                  80
Asn Asn Glu Ala Glu Asp Gln Asp Phe Glu Lys Ser Asn Ser Arg Lys
                85                  90                  95
Arg Pro Arg Asp Val Pro Gln Gln Glu Glu Ala Glu Gly Asn Tyr
                100                 105                 110
Gln Glu Ser Trp Gln Ala Ser Gly Ser Gln Pro Tyr Ser Pro Glu His
            115                 120                 125
Arg Gln Lys Lys His Arg Lys Leu Pro Glu Leu Glu Arg Pro His Lys
            130                 135                 140
Val Ala His Gly His Glu Arg Arg Asp Glu Arg Lys Arg Cys His Lys
145                 150                 155                 160
Val Ser Pro Pro Tyr Ser Ser Asp Pro Glu Ser Ser Asp Tyr Gly His
                165                 170                 175
Val Gln Ser Pro Pro Ser Ser Pro His Gln Met Tyr Thr Asp Leu
            180                 185                 190
Ser Arg Ser Pro Glu Met Asp Gln Glu Pro Ile Val Ser His Pro Lys
            195                 200                 205
Pro Gly Lys Val His Ser Asn Thr Phe Gln Asp Arg Leu Gly Val Ser
210                 215                 220
His Leu Gly Glu His Gln Gly Lys Gly Ala Val Ser Gln Asn Lys Pro
225                 230                 235                 240
His Lys Ser Ser His Lys Glu Lys Arg Pro Val Asp Ala Arg Gly Asp
                245                 250                 255
Glu Lys Ser Ser Val Met Gly Arg Glu Lys Ser His Lys Ala Ser Ser
            260                 265                 270
Lys Glu Glu Ser Arg Arg Leu Leu Ser Glu Asp Ser Ala Lys Glu Lys
            275                 280                 285
Leu Pro Ser Ser Val Val Lys Lys Glu Lys Asp Arg Glu Gly Asn Ser
            290                 295                 300
Leu Lys Lys Lys Leu Ser Pro Ala Leu Asp Val Ala Ser Asp Asn His
305                 310                 315                 320
Phe Lys Lys Pro Lys His Lys Asp Ser Glu Lys Ile Lys Ser Asp Lys
                325                 330                 335
Asn Lys Gln Ser Val Asp Ser Val Asp Ser Gly Arg Gly Thr Gly Asp
            340                 345                 350
Pro Leu Pro Arg Ala Lys Asp Lys Val Pro Asn Asn Leu Lys Ala Gln
            355                 360                 365
Glu Gly Lys Val Arg Thr Asn Ser Asp Arg Lys Ser Pro Gly Ser Leu
370                 375                 380
Pro Lys Val Glu Glu Met Asp Met Asp Glu Phe Glu Gln Pro Thr
385                 390                 395                 400
Met Ser Phe Glu Ser Tyr Leu Ser Tyr Asp Gln Pro Arg Lys Lys Lys
                405                 410                 415
```

```
Lys Lys Val Val Lys Thr Ser Gly Thr Ala Leu Gly Glu Lys Gly Leu
                420                 425                 430

Lys Lys Lys Asp Ser Lys Ser Thr Ser Lys Asn Leu Asn Ser Ala Gln
            435                 440                 445

Lys Leu Pro Lys Ala Asn Glu Asn Lys Ser Asp Lys Leu Gln Pro Ala
        450                 455                 460

Gly Ala Glu Pro Thr Arg Pro Arg Lys Val Pro Thr Asp Val Leu Pro
465                 470                 475                 480

Ala Leu Pro Asp Ile Pro Leu Pro Ala Ile Gln Thr Asn Tyr Arg Pro
                485                 490                 495

Leu Pro Ser Leu Glu Leu Ile Ser Ser Phe Gln Pro Lys Arg Lys Ala
                500                 505                 510

Phe Ser Ser Pro Gln Glu Glu Glu Ala Gly Phe Thr Gly Arg Arg
                515                 520                 525

Met Asn Ser Lys Met Gln Val Tyr Ser Gly Ser Lys Cys Ala Tyr Leu
                530                 535                 540

Pro Lys Met Met Thr Leu His Gln Gln Cys Ile Arg Val Leu Lys Asn
545                 550                 555                 560

Asn Ile Asp Ser Ile Phe Glu Val Gly Gly Val Pro Tyr Ser Val Leu
                565                 570                 575

Glu Pro Val Leu Glu Arg Cys Thr Pro Asp Gln Leu Tyr Arg Ile Glu
                580                 585                 590

Glu Cys Asn His Val Leu Ile Glu Glu Thr Asp Gln Leu Trp Lys Val
                595                 600                 605

His Cys His Arg Asp Phe Lys Glu Glu Arg Pro Glu Glu Tyr Glu Ser
                610                 615                 620

Trp Arg Glu Met Tyr Leu
625                 630
```

(2) INFORMATION FOR SEQ ID NO:18:

(i) SEQUENCE CHARACTERISTICS:
        (A) LENGTH: 535 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..535
        (D) OTHER INFORMATION: /note= "amino acids 1-535 of
            Elongin A"

(xi) SEQUENCE DESCRIPTION: SEQ ID NO:18:

```
Met Ala Ala Glu Ser Ala Leu Gln Val Val Glu Lys Leu Gln Ala Arg
1               5                   10                  15

Leu Ala Ala Asn Pro Asp Pro Lys Lys Leu Leu Lys Tyr Leu Lys Lys
                20                  25                  30

Leu Ser Val Leu Pro Ile Thr Val Asp Ile Leu Val Glu Thr Gly Val
                35                  40                  45

Gly Lys Thr Val Asn Ser Phe Arg Lys His Glu Gln Val Gly Asn Phe
            50                  55                  60

Ala Arg Asp Leu Val Ala Gln Trp Lys Lys Leu Val Pro Val Glu Arg
65                  70                  75                  80

Asn Asn Glu Ala Glu Asp Gln Asp Phe Glu Lys Ser Asn Ser Arg Lys
                85                  90                  95
```

-continued

```
Arg Pro Arg Asp Val Pro Gln Gln Glu Glu Ala Glu Gly Asn Tyr
            100                 105                 110

Gln Glu Ser Trp Gln Ala Ser Gly Ser Gln Pro Tyr Ser Pro Glu His
        115                 120                 125

Arg Gln Lys Lys His Arg Lys Leu Pro Glu Leu Glu Arg Pro His Lys
    130                 135                 140

Val Ala His Gly His Glu Arg Asp Glu Arg Lys Arg Cys His Lys
145                 150                 155                 160

Val Ser Pro Pro Tyr Ser Ser Asp Pro Glu Ser Ser Asp Tyr Gly His
                165                 170                 175

Val Gln Ser Pro Pro Ser Ser Pro His Gln Met Tyr Thr Asp Leu
        180                 185                 190

Ser Arg Ser Pro Glu Met Asp Gln Glu Pro Ile Val Ser His Pro Lys
    195                 200                 205

Pro Gly Lys Val His Ser Asn Thr Phe Gln Asp Arg Leu Gly Val Ser
    210                 215                 220

His Leu Gly Glu His Gln Gly Lys Gly Ala Val Ser Gln Asn Lys Pro
225                 230                 235                 240

His Lys Ser Ser His Lys Glu Lys Arg Pro Val Asp Ala Arg Gly Asp
                245                 250                 255

Glu Lys Ser Ser Val Met Gly Arg Glu Lys Ser His Lys Ala Ser Ser
            260                 265                 270

Lys Glu Glu Ser Arg Arg Leu Leu Ser Glu Asp Ser Ala Lys Glu Lys
        275                 280                 285

Leu Pro Ser Ser Val Val Lys Lys Glu Lys Asp Arg Glu Gly Asn Ser
    290                 295                 300

Leu Lys Lys Lys Leu Ser Pro Ala Leu Asp Val Ala Ser Asp Asn His
305                 310                 315                 320

Phe Lys Lys Pro Lys His Lys Asp Ser Glu Lys Ile Lys Ser Asp Lys
                325                 330                 335

Asn Lys Gln Ser Val Asp Ser Val Asp Ser Gly Arg Gly Thr Gly Asp
            340                 345                 350

Pro Leu Pro Arg Ala Lys Asp Lys Val Pro Asn Asn Leu Lys Ala Gln
        355                 360                 365

Glu Gly Lys Val Arg Thr Asn Ser Asp Arg Lys Ser Pro Gly Ser Leu
    370                 375                 380

Pro Lys Val Glu Glu Met Asp Met Asp Asp Glu Phe Glu Gln Pro Thr
385                 390                 395                 400

Met Ser Phe Glu Ser Tyr Leu Ser Tyr Asp Gln Pro Arg Lys Lys
                405                 410                 415

Lys Lys Val Val Lys Thr Ser Gly Thr Ala Leu Gly Glu Lys Gly Leu
            420                 425                 430

Lys Lys Lys Asp Ser Lys Ser Thr Ser Lys Asn Leu Asn Ser Ala Gln
        435                 440                 445

Lys Leu Pro Lys Ala Asn Glu Asn Lys Ser Asp Lys Leu Gln Pro Ala
    450                 455                 460

Gly Ala Glu Pro Thr Arg Pro Arg Lys Val Pro Thr Asp Val Leu Pro
465                 470                 475                 480

Ala Leu Pro Asp Ile Pro Leu Pro Ala Ile Gln Thr Asn Tyr Arg Pro
                485                 490                 495

Leu Pro Ser Leu Glu Leu Ile Ser Ser Phe Gln Pro Lys Arg Lys Ala
            500                 505                 510

Phe Ser Ser Pro Gln Glu Glu Glu Ala Gly Phe Thr Gly Arg Arg
```

```
                        515                 520                 525

Met Asn Ser Lys Met Gln Val
        530                 535

(2) INFORMATION FOR SEQ ID NO:19:

(i) SEQUENCE CHARACTERISTICS:
        (A) LENGTH: 400 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..400
        (D) OTHER INFORMATION: /note= "amino acids 1-400 of
            Elongin A"

(xi) SEQUENCE DESCRIPTION: SEQ ID NO:19:

Met Ala Ala Glu Ser Ala Leu Gln Val Val Glu Lys Leu Gln Ala Arg
    1               5                   10                  15

Leu Ala Ala Asn Pro Asp Pro Lys Lys Leu Leu Lys Tyr Leu Lys Lys
                    20                  25                  30

Leu Ser Val Leu Pro Ile Thr Val Asp Ile Leu Val Glu Thr Gly Val
                35                  40                  45

Gly Lys Thr Val Asn Ser Phe Arg Lys His Glu Gln Val Gly Asn Phe
    50                  55                  60

Ala Arg Asp Leu Val Ala Gln Trp Lys Lys Leu Val Pro Val Glu Arg
    65                  70                  75                  80

Asn Asn Glu Ala Glu Asp Gln Asp Phe Glu Lys Ser Asn Ser Arg Lys
                    85                  90                  95

Arg Pro Arg Asp Val Pro Gln Gln Glu Glu Ala Glu Gly Asn Tyr
                100                 105                 110

Gln Glu Ser Trp Gln Ala Ser Gly Ser Gln Pro Tyr Ser Pro Glu His
                115                 120                 125

Arg Gln Lys Lys His Arg Lys Leu Pro Glu Leu Glu Arg Pro His Lys
    130                 135                 140

Val Ala His Gly His Glu Arg Arg Asp Glu Arg Lys Arg Cys His Lys
    145                 150                 155                 160

Val Ser Pro Pro Tyr Ser Ser Asp Pro Glu Ser Ser Asp Tyr Gly His
                    165                 170                 175

Val Gln Ser Pro Pro Pro Ser Ser Pro His Gln Met Tyr Thr Asp Leu
                180                 185                 190

Ser Arg Ser Pro Glu Met Asp Gln Glu Pro Ile Val Ser His Pro Lys
                195                 200                 205

Pro Gly Lys Val His Ser Asn Thr Phe Gln Asp Arg Leu Gly Val Ser
    210                 215                 220

His Leu Gly Glu His Gln Gly Lys Gly Ala Val Ser Gln Asn Lys Pro
    225                 230                 235                 240

His Lys Ser Ser His Lys Glu Lys Arg Pro Val Asp Ala Arg Gly Asp
                    245                 250                 255

Glu Lys Ser Ser Val Met Gly Arg Glu Lys Ser His Lys Ala Ser Ser
                    260                 265                 270

Lys Glu Glu Ser Arg Arg Leu Leu Ser Glu Asp Ser Ala Lys Glu Lys
                275                 280                 285

Leu Pro Ser Ser Val Val Lys Lys Glu Lys Asp Arg Glu Gly Asn Ser
```

```
                       290                 295                 300

Leu Lys Lys Lys Leu Ser Pro Ala Leu Asp Val Ala Ser Asp Asn His
305                 310                 315                 320

Phe Lys Lys Pro Lys His Lys Asp Ser Glu Lys Ile Lys Ser Asp Lys
                325                 330                 335

Asn Lys Gln Ser Val Asp Ser Val Asp Ser Gly Arg Gly Thr Gly Asp
            340                 345                 350

Pro Leu Pro Arg Ala Lys Asp Lys Val Pro Asn Asn Leu Lys Ala Gln
        355                 360                 365

Glu Gly Lys Val Arg Thr Asn Ser Asp Arg Lys Ser Pro Gly Ser Leu
    370                 375                 380

Pro Lys Val Glu Glu Met Asp Met Asp Asp Glu Phe Glu Gln Pro Thr
385                 390                 395                 400
```

(2) INFORMATION FOR SEQ ID NO:20:

(i) SEQUENCE CHARACTERISTICS:
        (A) LENGTH: 94 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Peptide
        (B) LOCATION: 1..94
        (D) OTHER INFORMATION: /note= "amino acids 680-773 of
           Elongin A"

(xi) SEQUENCE DESCRIPTION: SEQ ID NO:20:

```
Glu Lys Phe Gly Thr Gly Gly Ala Ala Val Pro Glu Lys Val Arg Ile
1               5                   10                  15

Lys Pro Ala Pro Tyr Thr Thr Gly Ser Ser His Val Pro Ala Ser Asn
            20                  25                  30

Ser Ser Ser Ser Phe His Ser Ser Pro Glu Glu Leu Ala Tyr Glu Gly
        35                  40                  45

Pro Ser Thr Ser Ser Ala His Leu Ala Pro Val Ala Ser Ser Ser Val
50                  55                  60

Ser Tyr Asp Pro Arg Lys Pro Ala Val Lys Ile Ala Pro Met Met
65                  70                  75                  80

Ala Lys Thr Ile Lys Ala Phe Lys Asn Arg Phe Ser Arg Arg
                85                  90
```

(2) INFORMATION FOR SEQ ID NO:21:

(i) SEQUENCE CHARACTERISTICS:
        (A) LENGTH: 733 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..733
        (D) OTHER INFORMATION: /note= "amino acids 1-400 and
           441-773 of Elongin A"

(xi) SEQUENCE DESCRIPTION: SEQ ID NO:21:

```
Met Ala Ala Glu Ser Ala Leu Gln Val Val Glu Lys Leu Gln Ala Arg
1               5                   10                  15
```

-continued

```
Leu Ala Ala Asn Pro Asp Pro Lys Lys Leu Leu Lys Tyr Leu Lys Lys
                 20                  25                  30

Leu Ser Val Leu Pro Ile Thr Val Asp Ile Leu Val Glu Thr Gly Val
         35                  40                  45

Gly Lys Thr Val Asn Ser Phe Arg Lys His Glu Gln Val Gly Asn Phe
     50                  55                  60

Ala Arg Asp Leu Val Ala Gln Trp Lys Lys Leu Val Pro Val Glu Arg
65                  70                  75                  80

Asn Asn Glu Ala Glu Asp Gln Asp Phe Glu Lys Ser Asn Ser Arg Lys
                 85                  90                  95

Arg Pro Arg Asp Val Pro Gln Gln Glu Glu Ala Glu Gly Asn Tyr
                100                 105                 110

Gln Glu Ser Trp Gln Ala Ser Gly Ser Gln Pro Tyr Ser Pro Glu His
            115                 120                 125

Arg Gln Lys Lys His Arg Lys Leu Pro Glu Leu Glu Arg Pro His Lys
            130                 135                 140

Val Ala His Gly His Glu Arg Arg Asp Glu Arg Lys Arg Cys His Lys
145                 150                 155                 160

Val Ser Pro Pro Tyr Ser Ser Asp Pro Glu Ser Ser Asp Tyr Gly His
                165                 170                 175

Val Gln Ser Pro Pro Ser Ser Pro His Gln Met Tyr Thr Asp Leu
            180                 185                 190

Ser Arg Ser Pro Glu Met Asp Gln Glu Pro Ile Val Ser His Pro Lys
        195                 200                 205

Pro Gly Lys Val His Ser Asn Thr Phe Gln Asp Arg Leu Gly Val Ser
    210                 215                 220

His Leu Gly Glu His Gln Gly Lys Gly Ala Val Ser Gln Asn Lys Pro
225                 230                 235                 240

His Lys Ser Ser His Lys Glu Lys Arg Pro Val Asp Ala Arg Gly Asp
                245                 250                 255

Glu Lys Ser Ser Val Met Gly Arg Glu Lys Ser His Lys Ala Ser Ser
                260                 265                 270

Lys Glu Glu Ser Arg Arg Leu Leu Ser Glu Asp Ser Ala Lys Glu Lys
            275                 280                 285

Leu Pro Ser Ser Val Val Lys Lys Glu Lys Asp Arg Glu Gly Asn Ser
    290                 295                 300

Leu Lys Lys Lys Leu Ser Pro Ala Leu Asp Val Ala Ser Asp Asn His
305                 310                 315                 320

Phe Lys Lys Pro Lys His Lys Asp Ser Glu Lys Ile Lys Ser Asp Lys
                325                 330                 335

Asn Lys Gln Ser Val Asp Ser Val Asp Ser Gly Arg Gly Thr Gly Asp
            340                 345                 350

Pro Leu Pro Arg Ala Lys Asp Lys Val Pro Asn Asn Leu Lys Ala Gln
    355                 360                 365

Glu Gly Lys Val Arg Thr Asn Ser Asp Arg Lys Ser Pro Gly Ser Leu
    370                 375                 380

Pro Lys Val Glu Glu Met Asp Met Asp Glu Phe Glu Gln Pro Thr
385                 390                 395                 400

Ser Lys Asn Leu Asn Ser Ala Gln Lys Leu Pro Lys Ala Asn Glu Asn
                405                 410                 415

Lys Ser Asp Lys Leu Gln Pro Ala Gly Ala Glu Pro Thr Arg Pro Arg
            420                 425                 430

Lys Val Pro Thr Asp Val Leu Pro Ala Leu Pro Asp Ile Pro Leu Pro
```

-continued

```
                435                 440                 445
    Ala Ile Gln Thr Asn Tyr Arg Pro Leu Pro Ser Leu Glu Leu Ile Ser
        450                 455                 460

Ser Phe Gln Pro Lys Arg Lys Ala Phe Ser Ser Pro Gln Glu Glu Glu
    465                 470                 475                 480

Glu Ala Gly Phe Thr Gly Arg Arg Met Asn Ser Lys Met Gln Val Tyr
                    485                 490                 495

Ser Gly Ser Lys Cys Ala Tyr Leu Pro Lys Met Met Thr Leu His Gln
                500                 505                 510

Gln Cys Ile Arg Val Leu Lys Asn Asn Ile Asp Ser Ile Phe Glu Val
                515                 520                 525

Gly Gly Val Pro Tyr Ser Val Leu Glu Pro Val Leu Glu Arg Cys Thr
            530                 535                 540

Pro Asp Gln Leu Tyr Arg Ile Glu Glu Cys Asn His Val Leu Ile Glu
    545                 550                 555                 560

Glu Thr Asp Gln Leu Trp Lys Val His Cys His Arg Asp Phe Lys Glu
                    565                 570                 575

Glu Arg Pro Glu Glu Tyr Glu Ser Trp Arg Glu Met Tyr Leu Arg Leu
                580                 585                 590

Gln Asp Ala Arg Glu Gln Arg Leu Arg Leu Leu Thr Asn Asn Ile Arg
                595                 600                 605

Ser Ala His Ala Asn Lys Pro Lys Gly Arg Gln Ala Lys Met Ala Phe
    610                 615                 620

Val Asn Ser Val Ala Lys Pro Pro Arg Asp Val Arg Arg Gln Glu
    625                 630                 635                 640

Lys Phe Gly Thr Gly Gly Ala Ala Val Pro Glu Lys Val Arg Ile Lys
                    645                 650                 655

Pro Ala Pro Tyr Thr Thr Gly Ser Ser His Val Pro Ala Ser Asn Ser
                660                 665                 670

Ser Ser Ser Phe His Ser Ser Pro Glu Glu Leu Ala Tyr Glu Gly Pro
                675                 680                 685

Ser Thr Ser Ser Ala His Leu Ala Pro Val Ala Ser Ser Val Ser
                690                 695                 700

Tyr Asp Pro Arg Lys Pro Ala Val Lys Lys Ile Ala Pro Met Met Ala
    705                 710                 715                 720

Lys Thr Ile Lys Ala Phe Lys Asn Arg Phe Ser Arg Arg
                    725                 730
```

(2) INFORMATION FOR SEQ ID NO:22:

(i) SEQUENCE CHARACTERISTICS:
        (A) LENGTH: 733 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..733
        (D) OTHER INFORMATION: /note= "amino acids 1-440 and
           481-773 of Elongin A"

(xi) SEQUENCE DESCRIPTION: SEQ ID NO:22:

```
Met Ala Ala Glu Ser Ala Leu Gln Val Val Glu Lys Leu Gln Ala Arg
1               5                   10                  15

Leu Ala Ala Asn Pro Asp Pro Lys Lys Leu Leu Lys Tyr Leu Lys Lys
```

```
                20                  25                  30
Leu Ser Val Leu Pro Ile Thr Val Asp Ile Leu Val Glu Thr Gly Val
             35                  40                  45
Gly Lys Thr Val Asn Ser Phe Arg Lys His Glu Gln Val Gly Asn Phe
 50                  55                  60
Ala Arg Asp Leu Val Ala Gln Trp Lys Lys Leu Val Pro Val Glu Arg
 65                  70                  75                  80
Asn Asn Glu Ala Glu Asp Gln Asp Phe Glu Lys Ser Asn Ser Arg Lys
             85                  90                  95
Arg Pro Arg Asp Val Pro Gln Glu Glu Ala Glu Gly Asn Tyr
            100                 105                 110
Gln Glu Ser Trp Gln Ala Ser Gly Ser Gln Pro Tyr Ser Pro Glu His
            115                 120                 125
Arg Gln Lys Lys His Arg Lys Leu Pro Glu Leu Glu Arg Pro His Lys
            130                 135                 140
Val Ala His Gly His Glu Arg Arg Asp Glu Arg Lys Arg Cys His Lys
145                 150                 155                 160
Val Ser Pro Pro Tyr Ser Ser Asp Pro Glu Ser Ser Asp Tyr Gly His
                165                 170                 175
Val Gln Ser Pro Pro Pro Ser Ser Pro His Gln Met Tyr Thr Asp Leu
                180                 185                 190
Ser Arg Ser Pro Glu Met Asp Gln Glu Pro Ile Val Ser His Pro Lys
                195                 200                 205
Pro Gly Lys Val His Ser Asn Thr Phe Gln Asp Arg Leu Gly Val Ser
            210                 215                 220
His Leu Gly Glu His Gln Gly Lys Gly Ala Val Ser Gln Asn Lys Pro
225                 230                 235                 240
His Lys Ser Ser His Lys Glu Lys Arg Pro Val Asp Ala Arg Gly Asp
                245                 250                 255
Glu Lys Ser Ser Val Met Gly Arg Glu Lys Ser His Lys Ala Ser Ser
            260                 265                 270
Lys Glu Glu Ser Arg Arg Leu Leu Ser Glu Asp Ser Ala Lys Glu Lys
            275                 280                 285
Leu Pro Ser Ser Val Val Lys Lys Glu Lys Asp Arg Glu Gly Asn Ser
            290                 295                 300
Leu Lys Lys Lys Leu Ser Pro Ala Leu Asp Val Ala Ser Asp Asn His
305                 310                 315                 320
Phe Lys Lys Pro Lys His Lys Asp Ser Glu Lys Ile Lys Ser Asp Lys
                325                 330                 335
Asn Lys Gln Ser Val Asp Ser Val Asp Ser Gly Arg Gly Thr Gly Asp
            340                 345                 350
Pro Leu Pro Arg Ala Lys Asp Lys Val Pro Asn Asn Leu Lys Ala Gln
            355                 360                 365
Glu Gly Lys Val Arg Thr Asn Ser Asp Arg Lys Ser Pro Gly Ser Leu
            370                 375                 380
Pro Lys Val Glu Glu Met Asp Met Asp Glu Phe Glu Gln Pro Thr
385                 390                 395                 400
Met Ser Phe Glu Ser Tyr Leu Ser Tyr Asp Gln Pro Arg Lys Lys Lys
                405                 410                 415
Lys Lys Val Val Lys Thr Ser Gly Thr Ala Leu Gly Glu Lys Gly Leu
            420                 425                 430
Lys Lys Lys Asp Ser Lys Ser Thr Ala Leu Pro Asp Ile Pro Leu Pro
            435                 440                 445
```

```
        Ala Ile Gln Thr Asn Tyr Arg Pro Leu Pro Ser Leu Glu Leu Ile Ser
            450                 455                 460

Ser Phe Gln Pro Lys Arg Lys Ala Phe Ser Ser Pro Gln Glu Glu Glu
        465                 470                 475                 480

Glu Ala Gly Phe Thr Gly Arg Arg Met Asn Ser Lys Met Gln Val Tyr
                        485                 490                 495

Ser Gly Ser Lys Cys Ala Tyr Leu Pro Lys Met Met Thr Leu His Gln
                    500                 505                 510

Gln Cys Ile Arg Val Leu Lys Asn Asn Ile Asp Ser Ile Phe Glu Val
                515                 520                 525

Gly Gly Val Pro Tyr Ser Val Leu Glu Pro Val Leu Glu Arg Cys Thr
            530                 535                 540

Pro Asp Gln Leu Tyr Arg Ile Glu Glu Cys Asn His Val Leu Ile Glu
        545                 550                 555                 560

Glu Thr Asp Gln Leu Trp Lys Val His Cys His Arg Asp Phe Lys Glu
                        565                 570                 575

Glu Arg Pro Glu Glu Tyr Glu Ser Trp Arg Glu Met Tyr Leu Arg Leu
                    580                 585                 590

Gln Asp Ala Arg Glu Gln Arg Leu Arg Leu Thr Asn Asn Ile Arg
                595                 600                 605

Ser Ala His Ala Asn Lys Pro Lys Gly Arg Gln Ala Lys Met Ala Phe
            610                 615                 620

Val Asn Ser Val Ala Lys Pro Pro Arg Asp Val Arg Arg Gln Glu
        625                 630                 635                 640

Lys Phe Gly Thr Gly Gly Ala Val Pro Glu Lys Val Arg Ile Lys
                        645                 650                 655

Pro Ala Pro Tyr Thr Thr Gly Ser Ser His Val Pro Ala Ser Asn Ser
                    660                 665                 670

Ser Ser Ser Phe His Ser Ser Pro Glu Glu Leu Ala Tyr Glu Gly Pro
                675                 680                 685

Ser Thr Ser Ser Ala His Leu Ala Pro Val Ala Ser Ser Ser Val Ser
            690                 695                 700

Tyr Asp Pro Arg Lys Pro Ala Val Lys Lys Ile Ala Pro Met Met Ala
        705                 710                 715                 720

Lys Thr Ile Lys Ala Phe Lys Asn Arg Phe Ser Arg Arg
                        725                 730

(2) INFORMATION FOR SEQ ID NO:23:

(i) SEQUENCE CHARACTERISTICS:
        (A) LENGTH: 733 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..733
        (D) OTHER INFORMATION: /note= "amino acids 1-480 and
            521-773 of Elongin A"

(xi) SEQUENCE DESCRIPTION: SEQ ID NO:23:

Met Ala Ala Glu Ser Ala Leu Gln Val Val Glu Lys Leu Gln Ala Arg
1               5                   10                  15

Leu Ala Ala Asn Pro Asp Pro Lys Lys Leu Leu Lys Tyr Leu Lys Lys
                20                  25                  30
```

```
Leu Ser Val Leu Pro Ile Thr Val Asp Ile Leu Val Glu Thr Gly Val
         35                  40                  45

Gly Lys Thr Val Asn Ser Phe Arg Lys His Glu Gln Val Gly Asn Phe
 50                  55                  60

Ala Arg Asp Leu Val Ala Gln Trp Lys Lys Leu Val Pro Val Glu Arg
 65                  70                  75                  80

Asn Asn Glu Ala Glu Asp Gln Asp Phe Glu Lys Ser Asn Ser Arg Lys
                 85                  90                  95

Arg Pro Arg Asp Val Pro Gln Gln Glu Glu Ala Glu Gly Asn Tyr
                100                 105                 110

Gln Glu Ser Trp Gln Ala Ser Gly Ser Gln Pro Tyr Ser Pro Glu His
        115                 120                 125

Arg Gln Lys Lys His Arg Lys Leu Pro Glu Leu Glu Arg Pro His Lys
    130                 135                 140

Val Ala His Gly His Glu Arg Arg Asp Glu Arg Lys Arg Cys His Lys
145                 150                 155                 160

Val Ser Pro Pro Tyr Ser Ser Asp Pro Glu Ser Ser Asp Tyr Gly His
                165                 170                 175

Val Gln Ser Pro Pro Ser Ser Pro His Gln Met Tyr Thr Asp Leu
                180                 185                 190

Ser Arg Ser Pro Glu Met Asp Gln Glu Pro Ile Val Ser His Pro Lys
        195                 200                 205

Pro Gly Lys Val His Ser Asn Thr Phe Gln Asp Arg Leu Gly Val Ser
    210                 215                 220

His Leu Gly Glu His Gln Gly Lys Gly Ala Val Ser Gln Asn Lys Pro
225                 230                 235                 240

His Lys Ser Ser His Lys Glu Lys Arg Pro Val Asp Ala Arg Gly Asp
                245                 250                 255

Glu Lys Ser Ser Val Met Gly Arg Glu Lys Ser His Lys Ala Ser Ser
                260                 265                 270

Lys Glu Glu Ser Arg Arg Leu Leu Ser Glu Asp Ser Ala Lys Glu Lys
        275                 280                 285

Leu Pro Ser Ser Val Val Lys Lys Glu Lys Asp Arg Glu Gly Asn Ser
    290                 295                 300

Leu Lys Lys Lys Leu Ser Pro Ala Leu Asp Val Ala Ser Asp Asn His
305                 310                 315                 320

Phe Lys Lys Pro Lys His Lys Asp Ser Glu Lys Ile Lys Ser Asp Lys
                325                 330                 335

Asn Lys Gln Ser Val Asp Ser Val Asp Ser Gly Arg Gly Thr Gly Asp
                340                 345                 350

Pro Leu Pro Arg Ala Lys Asp Lys Val Pro Asn Asn Leu Lys Ala Gln
        355                 360                 365

Glu Gly Lys Val Arg Thr Asn Ser Asp Arg Lys Ser Pro Gly Ser Leu
    370                 375                 380

Pro Lys Val Glu Glu Met Asp Met Asp Glu Phe Glu Gln Pro Thr
385                 390                 395                 400

Met Ser Phe Glu Ser Tyr Leu Ser Tyr Asp Gln Pro Arg Lys Lys Lys
                405                 410                 415

Lys Lys Val Val Lys Thr Ser Gly Thr Ala Leu Gly Glu Lys Gly Leu
                420                 425                 430

Lys Lys Lys Asp Ser Lys Ser Thr Ser Lys Asn Leu Asn Ser Ala Gln
        435                 440                 445
```

-continued

```
Lys Leu Pro Lys Ala Asn Glu Asn Lys Ser Asp Lys Leu Gln Pro Ala
    450                 455                 460
Gly Ala Glu Pro Thr Arg Pro Arg Lys Val Pro Thr Asp Val Leu Pro
465                 470                 475                 480
Glu Ala Gly Phe Thr Gly Arg Arg Met Asn Ser Lys Met Gln Val Tyr
                    485                 490                 495
Ser Gly Ser Lys Cys Ala Tyr Leu Pro Lys Met Met Thr Leu His Gln
                500                 505                 510
Gln Cys Ile Arg Val Leu Lys Asn Asn Ile Asp Ser Ile Phe Glu Val
            515                 520                 525
Gly Gly Val Pro Tyr Ser Val Leu Glu Pro Val Leu Glu Arg Cys Thr
        530                 535                 540
Pro Asp Gln Leu Tyr Arg Ile Glu Glu Cys Asn His Val Leu Ile Glu
545                 550                 555                 560
Glu Thr Asp Gln Leu Trp Lys Val His Cys His Arg Asp Phe Lys Glu
                    565                 570                 575
Glu Arg Pro Glu Glu Tyr Glu Ser Trp Arg Glu Met Tyr Leu Arg Leu
                580                 585                 590
Gln Asp Ala Arg Glu Gln Arg Leu Arg Leu Leu Thr Asn Asn Ile Arg
            595                 600                 605
Ser Ala His Ala Asn Lys Pro Lys Gly Arg Gln Ala Lys Met Ala Phe
        610                 615                 620
Val Asn Ser Val Ala Lys Pro Pro Arg Asp Val Arg Arg Arg Gln Glu
625                 630                 635                 640
Lys Phe Gly Thr Gly Gly Ala Ala Val Pro Glu Lys Val Arg Ile Lys
                    645                 650                 655
Pro Ala Pro Tyr Thr Thr Gly Ser Ser His Val Pro Ala Ser Asn Ser
                660                 665                 670
Ser Ser Ser Phe His Ser Ser Pro Glu Glu Leu Ala Tyr Glu Gly Pro
            675                 680                 685
Ser Thr Ser Ser Ala His Leu Ala Pro Val Ala Ser Ser Ser Val Ser
        690                 695                 700
Tyr Asp Pro Arg Lys Pro Ala Val Lys Lys Ile Ala Pro Met Met Ala
705                 710                 715                 720
Lys Thr Ile Lys Ala Phe Lys Asn Arg Phe Ser Arg Arg
                    725                 730
```

(2) INFORMATION FOR SEQ ID NO:24:

(i) SEQUENCE CHARACTERISTICS:
        (A) LENGTH: 748 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..748
        (D) OTHER INFORMATION: /note= "amino acids 1-520 and
          546-773 of Elongin A"

(xi) SEQUENCE DESCRIPTION: SEQ ID NO:24:

```
Met Ala Ala Glu Ser Ala Leu Gln Val Val Glu Lys Leu Gln Ala Arg
1               5                   10                  15
Leu Ala Ala Asn Pro Asp Pro Lys Lys Leu Leu Lys Tyr Leu Lys Lys
            20                  25                  30
```

```
Leu Ser Val Leu Pro Ile Thr Val Asp Ile Leu Val Glu Thr Gly Val
        35                  40                  45

Gly Lys Thr Val Asn Ser Phe Arg Lys His Glu Gln Val Gly Asn Phe
    50                  55                  60

Ala Arg Asp Leu Val Ala Gln Trp Lys Lys Leu Val Pro Val Glu Arg
65                  70                  75                  80

Asn Asn Glu Ala Glu Asp Gln Asp Phe Glu Lys Ser Asn Ser Arg Lys
                85                  90                  95

Arg Pro Arg Asp Val Pro Gln Gln Glu Glu Ala Glu Gly Asn Tyr
                100                 105                 110

Gln Glu Ser Trp Gln Ala Ser Gly Ser Gln Pro Tyr Ser Pro Glu His
        115                 120                 125

Arg Gln Lys Lys His Arg Lys Leu Pro Glu Leu Glu Arg Pro His Lys
    130                 135                 140

Val Ala His Gly His Glu Arg Arg Asp Glu Arg Lys Arg Cys His Lys
145                 150                 155                 160

Val Ser Pro Pro Tyr Ser Ser Asp Pro Glu Ser Ser Asp Tyr Gly His
                165                 170                 175

Val Gln Ser Pro Pro Ser Ser Pro His Gln Met Tyr Thr Asp Leu
        180                 185                 190

Ser Arg Ser Pro Glu Met Asp Gln Glu Pro Ile Val Ser His Pro Lys
    195                 200                 205

Pro Gly Lys Val His Ser Asn Thr Phe Gln Asp Arg Leu Gly Val Ser
    210                 215                 220

His Leu Gly Glu His Gln Gly Lys Gly Ala Val Ser Gln Asn Lys Pro
225                 230                 235                 240

His Lys Ser Ser His Lys Glu Lys Arg Pro Val Asp Ala Arg Gly Asp
                245                 250                 255

Glu Lys Ser Ser Val Met Gly Arg Glu Lys Ser His Lys Ala Ser Ser
                260                 265                 270

Lys Glu Glu Ser Arg Arg Leu Leu Ser Glu Asp Ser Ala Lys Glu Lys
    275                 280                 285

Leu Pro Ser Ser Val Val Lys Lys Glu Lys Asp Arg Glu Gly Asn Ser
    290                 295                 300

Leu Lys Lys Lys Leu Ser Pro Ala Leu Asp Val Ala Ser Asp Asn His
305                 310                 315                 320

Phe Lys Lys Pro Lys His Lys Asp Ser Glu Lys Ile Lys Ser Asp Lys
                325                 330                 335

Asn Lys Gln Ser Val Asp Ser Val Asp Ser Gly Arg Gly Thr Gly Asp
                340                 345                 350

Pro Leu Pro Arg Ala Lys Asp Lys Val Pro Asn Asn Leu Lys Ala Gln
        355                 360                 365

Glu Gly Lys Val Arg Thr Asn Ser Asp Arg Lys Ser Pro Gly Ser Leu
    370                 375                 380

Pro Lys Val Glu Glu Met Asp Met Asp Glu Phe Glu Gln Pro Thr
385                 390                 395                 400

Met Ser Phe Glu Ser Tyr Leu Ser Tyr Asp Gln Pro Arg Lys Lys Lys
                405                 410                 415

Lys Lys Val Val Lys Thr Ser Gly Thr Ala Leu Gly Glu Lys Gly Leu
                420                 425                 430

Lys Lys Lys Asp Ser Lys Ser Thr Ser Lys Asn Leu Asn Ser Ala Gln
                435                 440                 445

Lys Leu Pro Lys Ala Asn Glu Asn Lys Ser Asp Lys Leu Gln Pro Ala
```

```
                450                 455                 460
    Gly Ala Glu Pro Thr Arg Pro Arg Lys Val Pro Thr Asp Val Leu Pro
    465                 470                 475                 480

Ala Leu Pro Asp Ile Pro Leu Pro Ala Ile Gln Thr Asn Tyr Arg Pro
                    485                 490                 495

Leu Pro Ser Leu Glu Leu Ile Ser Ser Phe Gln Pro Lys Arg Lys Ala
                500                 505                 510

Phe Ser Ser Pro Gln Glu Glu Glu Lys Met Met Thr Leu His Gln Gln
                515                 520                 525

Cys Ile Arg Val Leu Lys Asn Asn Ile Asp Ser Ile Phe Glu Val Gly
                530                 535                 540

Gly Val Pro Tyr Ser Val Leu Glu Pro Val Leu Glu Arg Cys Thr Pro
    545                 550                 555                 560

Asp Gln Leu Tyr Arg Ile Glu Glu Cys Asn His Val Leu Ile Glu Glu
                    565                 570                 575

Thr Asp Gln Leu Trp Lys Val His Cys His Arg Asp Phe Lys Glu Glu
                580                 585                 590

Arg Pro Glu Glu Tyr Glu Ser Trp Arg Glu Met Tyr Leu Arg Leu Gln
                595                 600                 605

Asp Ala Arg Glu Gln Arg Leu Arg Leu Leu Thr Asn Asn Ile Arg Ser
    610                 615                 620

Ala His Ala Asn Lys Pro Lys Gly Arg Gln Ala Lys Met Ala Phe Val
    625                 630                 635                 640

Asn Ser Val Ala Lys Pro Pro Arg Asp Val Arg Arg Gln Glu Lys
                    645                 650                 655

Phe Gly Thr Gly Gly Ala Ala Val Pro Glu Lys Val Arg Ile Lys Pro
                660                 665                 670

Ala Pro Tyr Thr Thr Gly Ser Ser His Val Pro Ala Ser Asn Ser Ser
                675                 680                 685

Ser Ser Phe His Ser Ser Pro Glu Glu Leu Ala Tyr Glu Gly Pro Ser
                690                 695                 700

Thr Ser Ser Ala His Leu Ala Pro Val Ala Ser Ser Val Ser Tyr
    705                 710                 715                 720

Asp Pro Arg Lys Pro Ala Val Lys Lys Ile Ala Pro Met Met Ala Lys
                    725                 730                 735

Thr Ile Lys Ala Phe Lys Asn Arg Phe Ser Arg Arg
                740                 745

(2) INFORMATION FOR SEQ ID NO:25:

(i) SEQUENCE CHARACTERISTICS:
        (A) LENGTH: 753 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..753
        (D) OTHER INFORMATION: /note= "amino acids 1-545 and
            566-773 of Elongin A"

(xi) SEQUENCE DESCRIPTION: SEQ ID NO:25:

Met Ala Ala Glu Ser Ala Leu Gln Val Val Glu Lys Leu Gln Ala Arg
1               5                   10                  15

Leu Ala Ala Asn Pro Asp Pro Lys Lys Leu Leu Lys Tyr Leu Lys Lys
```

```
                20                  25                  30
Leu Ser Val Leu Pro Ile Thr Val Asp Ile Leu Val Glu Thr Gly Val
                35                  40                  45
Gly Lys Thr Val Asn Ser Phe Arg Lys His Glu Gln Val Gly Asn Phe
 50                  55                  60
Ala Arg Asp Leu Val Ala Gln Trp Lys Lys Leu Val Pro Val Glu Arg
 65                  70                  75                  80
Asn Asn Glu Ala Glu Asp Gln Asp Phe Glu Lys Ser Asn Ser Arg Lys
                85                  90                  95
Arg Pro Arg Asp Val Pro Gln Glu Glu Ala Glu Gly Asn Tyr
                100                 105                 110
Gln Glu Ser Trp Gln Ala Ser Gly Ser Gln Pro Tyr Ser Pro Glu His
                115                 120                 125
Arg Gln Lys Lys His Arg Lys Leu Pro Glu Leu Glu Arg Pro His Lys
                130                 135                 140
Val Ala His Gly His Glu Arg Arg Asp Glu Arg Lys Arg Cys His Lys
145                 150                 155                 160
Val Ser Pro Pro Tyr Ser Ser Asp Pro Glu Ser Ser Asp Tyr Gly His
                165                 170                 175
Val Gln Ser Pro Pro Ser Ser Pro His Gln Met Tyr Thr Asp Leu
                180                 185                 190
Ser Arg Ser Pro Glu Met Asp Gln Glu Pro Ile Val Ser His Pro Lys
                195                 200                 205
Pro Gly Lys Val His Ser Asn Thr Phe Gln Asp Arg Leu Gly Val Ser
                210                 215                 220
His Leu Gly Glu His Gln Gly Lys Gly Ala Val Ser Gln Asn Lys Pro
225                 230                 235                 240
His Lys Ser Ser His Lys Glu Lys Arg Pro Val Asp Ala Arg Gly Asp
                245                 250                 255
Glu Lys Ser Ser Val Met Gly Arg Glu Lys Ser His Lys Ala Ser Ser
                260                 265                 270
Lys Glu Glu Ser Arg Arg Leu Leu Ser Glu Asp Ser Ala Lys Glu Lys
                275                 280                 285
Leu Pro Ser Ser Val Val Lys Lys Glu Lys Asp Arg Glu Gly Asn Ser
                290                 295                 300
Leu Lys Lys Lys Leu Ser Pro Ala Leu Asp Val Ala Ser Asp Asn His
305                 310                 315                 320
Phe Lys Lys Pro Lys His Lys Asp Ser Glu Lys Ile Lys Ser Asp Lys
                325                 330                 335
Asn Lys Gln Ser Val Asp Ser Val Asp Ser Gly Arg Gly Thr Gly Asp
                340                 345                 350
Pro Leu Pro Arg Ala Lys Asp Lys Val Pro Asn Asn Leu Lys Ala Gln
                355                 360                 365
Glu Gly Lys Val Arg Thr Asn Ser Asp Arg Lys Ser Pro Gly Ser Leu
                370                 375                 380
Pro Lys Val Glu Glu Met Asp Met Asp Glu Phe Glu Gln Pro Thr
385                 390                 395                 400
Met Ser Phe Glu Ser Tyr Leu Ser Tyr Asp Gln Pro Arg Lys Lys Lys
                405                 410                 415
Lys Lys Val Val Lys Thr Ser Gly Thr Ala Leu Gly Glu Lys Gly Leu
                420                 425                 430
Lys Lys Lys Asp Ser Lys Ser Thr Ser Lys Asn Leu Asn Ser Ala Gln
                435                 440                 445
```

Lys Leu Pro Lys Ala Asn Glu Asn Lys Ser Asp Lys Leu Gln Pro Ala
    450                 455                 460
Gly Ala Glu Pro Thr Arg Pro Arg Lys Val Pro Thr Asp Val Leu Pro
465                 470                 475                 480
Ala Leu Pro Asp Ile Pro Leu Pro Ala Ile Gln Thr Asn Tyr Arg Pro
                485                 490                 495
Leu Pro Ser Leu Glu Leu Ile Ser Ser Phe Gln Pro Lys Arg Lys Ala
                500                 505                 510
Phe Ser Ser Pro Gln Glu Glu Glu Ala Gly Phe Thr Gly Arg Arg
            515                 520                 525
Met Asn Ser Lys Met Gln Val Tyr Ser Gly Ser Lys Cys Ala Tyr Leu
    530                 535                 540
Pro Phe Glu Val Gly Gly Val Pro Tyr Ser Val Leu Glu Pro Val Leu
545                 550                 555                 560
Glu Arg Cys Thr Pro Asp Gln Leu Tyr Arg Ile Glu Glu Cys Asn His
                565                 570                 575
Val Leu Ile Glu Glu Thr Asp Gln Leu Trp Lys Val His Cys His Arg
                580                 585                 590
Asp Phe Lys Glu Glu Arg Pro Glu Glu Tyr Glu Ser Trp Arg Glu Met
            595                 600                 605
Tyr Leu Arg Leu Gln Asp Ala Arg Glu Gln Arg Leu Arg Leu Leu Thr
    610                 615                 620
Asn Asn Ile Arg Ser Ala His Ala Asn Lys Pro Lys Gly Arg Gln Ala
625                 630                 635                 640
Lys Met Ala Phe Val Asn Ser Val Ala Lys Pro Pro Arg Asp Val Arg
                645                 650                 655
Arg Arg Gln Glu Lys Phe Gly Thr Gly Gly Ala Ala Val Pro Glu Lys
            660                 665                 670
Val Arg Ile Lys Pro Ala Pro Tyr Thr Thr Gly Ser Ser His Val Pro
            675                 680                 685
Ala Ser Asn Ser Ser Ser Ser Phe His Ser Ser Pro Glu Glu Leu Ala
            690                 695                 700
Tyr Glu Gly Pro Ser Thr Ser Ser Ala His Leu Ala Pro Val Ala Ser
705                 710                 715                 720
Ser Ser Val Ser Tyr Asp Pro Arg Lys Pro Ala Val Lys Lys Ile Ala
                725                 730                 735
Pro Met Met Ala Lys Thr Ile Lys Ala Phe Lys Asn Arg Phe Ser Arg
            740                 745                 750

Arg (2) INFORMATION FOR SEQ ID NO:26:

(i) SEQUENCE CHARACTERISTICS:
        (A) LENGTH: 753 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..753
        (D) OTHER INFORMATION: /note= "amino acids 1-565 and
            586-773 of Elongin A"

(xi) SEQUENCE DESCRIPTION: SEQ ID NO:26:

-continued

```
Met Ala Ala Glu Ser Ala Leu Gln Val Glu Lys Leu Gln Ala Arg
 1               5                  10                  15

Leu Ala Ala Asn Pro Asp Pro Lys Lys Leu Lys Tyr Leu Lys Lys
                 20                  25                  30

Leu Ser Val Leu Pro Ile Thr Val Asp Ile Leu Val Glu Thr Gly Val
             35                  40                  45

Gly Lys Thr Val Asn Ser Phe Arg Lys His Glu Gln Val Gly Asn Phe
 50                  55                  60

Ala Arg Asp Leu Val Ala Gln Trp Lys Lys Leu Val Pro Val Glu Arg
 65                  70                  75                  80

Asn Asn Glu Ala Glu Asp Gln Asp Phe Glu Lys Ser Asn Ser Arg Lys
                 85                  90                  95

Arg Pro Arg Asp Val Pro Gln Gln Glu Glu Ala Glu Gly Asn Tyr
                100                 105                 110

Gln Glu Ser Trp Gln Ala Ser Gly Ser Gln Pro Tyr Ser Pro Glu His
            115                 120                 125

Arg Gln Lys Lys His Arg Lys Leu Pro Glu Leu Glu Arg Pro His Lys
            130                 135                 140

Val Ala His Gly His Glu Arg Arg Asp Glu Arg Lys Arg Cys His Lys
145                 150                 155                 160

Val Ser Pro Pro Tyr Ser Ser Asp Pro Glu Ser Ser Asp Tyr Gly His
                165                 170                 175

Val Gln Ser Pro Pro Pro Ser Ser Pro His Gln Met Tyr Thr Asp Leu
            180                 185                 190

Ser Arg Ser Pro Glu Met Asp Gln Glu Pro Ile Val Ser His Pro Lys
            195                 200                 205

Pro Gly Lys Val His Ser Asn Thr Phe Gln Asp Arg Leu Gly Val Ser
    210                 215                 220

His Leu Gly Glu His Gln Gly Lys Gly Ala Val Ser Gln Asn Lys Pro
225                 230                 235                 240

His Lys Ser Ser His Lys Glu Lys Arg Pro Val Asp Ala Arg Gly Asp
                245                 250                 255

Glu Lys Ser Ser Val Met Gly Arg Glu Lys Ser His Lys Ala Ser Ser
                260                 265                 270

Lys Glu Glu Ser Arg Arg Leu Leu Ser Glu Asp Ser Ala Lys Glu Lys
            275                 280                 285

Leu Pro Ser Ser Val Val Lys Lys Glu Lys Asp Arg Glu Gly Asn Ser
    290                 295                 300

Leu Lys Lys Lys Leu Ser Pro Ala Leu Asp Val Ala Ser Asp Asn His
305                 310                 315                 320

Phe Lys Lys Pro Lys His Lys Asp Ser Glu Lys Ile Lys Ser Asp Lys
                325                 330                 335

Asn Lys Gln Ser Val Asp Ser Val Asp Ser Gly Arg Gly Thr Gly Asp
            340                 345                 350

Pro Leu Pro Arg Ala Lys Asp Lys Val Pro Asn Asn Leu Lys Ala Gln
            355                 360                 365

Glu Gly Lys Val Arg Thr Asn Ser Asp Arg Lys Ser Pro Gly Ser Leu
    370                 375                 380

Pro Lys Val Glu Glu Met Asp Met Asp Asp Phe Glu Gln Pro Thr
385                 390                 395                 400

Met Ser Phe Glu Ser Tyr Leu Ser Tyr Asp Gln Pro Arg Lys Lys
                405                 410                 415

Lys Lys Val Val Lys Thr Ser Gly Thr Ala Leu Gly Glu Lys Gly Leu
```

```
              420             425             430
Lys Lys Lys Asp Ser Lys Ser Thr Ser Lys Asn Leu Asn Ser Ala Gln
        435             440             445

Lys Leu Pro Lys Ala Asn Glu Asn Lys Ser Asp Lys Leu Gln Pro Ala
    450             455             460

Gly Ala Glu Pro Thr Arg Pro Arg Lys Val Pro Thr Asp Val Leu Pro
465             470             475             480

Ala Leu Pro Asp Ile Pro Leu Pro Ala Ile Gln Thr Asn Tyr Arg Pro
            485             490             495

Leu Pro Ser Leu Glu Leu Ile Ser Ser Phe Gln Pro Lys Arg Lys Ala
        500             505             510

Phe Ser Ser Pro Gln Glu Glu Glu Ala Gly Phe Thr Gly Arg Arg
    515             520             525

Met Asn Ser Lys Met Gln Val Tyr Ser Gly Ser Lys Cys Ala Tyr Leu
    530             535             540

Pro Lys Met Met Thr Leu His Gln Gln Cys Ile Arg Val Leu Lys Asn
545             550             555             560

Asn Ile Asp Ser Ile Asp Gln Leu Tyr Arg Ile Glu Glu Cys Asn His
            565             570             575

Val Leu Ile Glu Glu Thr Asp Gln Leu Trp Lys Val His Cys His Arg
        580             585             590

Asp Phe Lys Glu Glu Arg Pro Glu Glu Tyr Glu Ser Trp Arg Glu Met
        595             600             605

Tyr Leu Arg Leu Gln Asp Ala Arg Glu Gln Arg Leu Arg Leu Leu Thr
        610             615             620

Asn Asn Ile Arg Ser Ala His Ala Asn Lys Pro Lys Gly Arg Gln Ala
625             630             635             640

Lys Met Ala Phe Val Asn Ser Val Ala Lys Pro Pro Arg Asp Val Arg
            645             650             655

Arg Arg Gln Glu Lys Phe Gly Thr Gly Gly Ala Ala Val Pro Glu Lys
        660             665             670

Val Arg Ile Lys Pro Ala Pro Tyr Thr Thr Gly Ser Ser His Val Pro
        675             680             685

Ala Ser Asn Ser Ser Ser Phe His Ser Ser Pro Glu Glu Leu Ala
    690             695             700

Tyr Glu Gly Pro Ser Thr Ser Ser Ala His Leu Ala Pro Val Ala Ser
705             710             715             720

Ser Ser Val Ser Tyr Asp Pro Arg Lys Pro Ala Val Lys Lys Ile Ala
            725             730             735

Pro Met Met Ala Lys Thr Ile Lys Ala Phe Lys Asn Arg Phe Ser Arg
            740             745             750

Arg (2) INFORMATION FOR SEQ ID NO:27:

(i) SEQUENCE CHARACTERISTICS:
        (A) LENGTH: 748 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..748
        (D) OTHER INFORMATION: /note= "amino acids 1-585 and
```

611-773 of Elongin A"

(xi) SEQUENCE DESCRIPTION: SEQ ID NO:27:

```
Met Ala Ala Glu Ser Ala Leu Gln Val Val Glu Lys Leu Gln Ala Arg
1               5                   10                  15

Leu Ala Ala Asn Pro Asp Pro Lys Lys Leu Leu Lys Tyr Leu Lys Lys
            20                  25                  30

Leu Ser Val Leu Pro Ile Thr Val Asp Ile Leu Val Glu Thr Gly Val
        35                  40                  45

Gly Lys Thr Val Asn Ser Phe Arg Lys His Glu Gln Val Gly Asn Phe
    50                  55                  60

Ala Arg Asp Leu Val Ala Gln Trp Lys Lys Leu Val Pro Val Glu Arg
65                  70                  75                  80

Asn Asn Glu Ala Glu Asp Gln Asp Phe Glu Lys Ser Asn Ser Arg Lys
                85                  90                  95

Arg Pro Arg Asp Val Pro Gln Gln Glu Glu Ala Glu Gly Asn Tyr
                100                 105                 110

Gln Glu Ser Trp Gln Ala Ser Gly Ser Gln Pro Tyr Ser Pro Glu His
            115                 120                 125

Arg Gln Lys Lys His Arg Lys Leu Pro Glu Leu Glu Arg Pro His Lys
130                 135                 140

Val Ala His Gly His Glu Arg Arg Asp Glu Arg Lys Arg Cys His Lys
145                 150                 155                 160

Val Ser Pro Pro Tyr Ser Ser Asp Pro Glu Ser Ser Asp Tyr Gly His
                165                 170                 175

Val Gln Ser Pro Pro Pro Ser Ser Pro His Gln Met Tyr Thr Asp Leu
            180                 185                 190

Ser Arg Ser Pro Glu Met Asp Gln Glu Pro Ile Val Ser His Pro Lys
        195                 200                 205

Pro Gly Lys Val His Ser Asn Thr Phe Gln Asp Arg Leu Gly Val Ser
    210                 215                 220

His Leu Gly Glu His Gln Gly Lys Gly Ala Val Ser Gln Asn Lys Pro
225                 230                 235                 240

His Lys Ser Ser His Lys Glu Lys Arg Pro Val Asp Ala Arg Gly Asp
                245                 250                 255

Glu Lys Ser Ser Val Met Gly Arg Glu Lys Ser His Lys Ala Ser Ser
            260                 265                 270

Lys Glu Glu Ser Arg Arg Leu Leu Ser Glu Asp Ser Ala Lys Glu Lys
        275                 280                 285

Leu Pro Ser Ser Val Val Lys Lys Glu Lys Asp Arg Glu Gly Asn Ser
    290                 295                 300

Leu Lys Lys Lys Leu Ser Pro Ala Leu Asp Val Ala Ser Asp Asn His
305                 310                 315                 320

Phe Lys Lys Pro Lys His Lys Asp Ser Glu Lys Ile Lys Ser Asp Lys
                325                 330                 335

Asn Lys Gln Ser Val Asp Ser Val Asp Ser Gly Arg Gly Thr Gly Asp
            340                 345                 350

Pro Leu Pro Arg Ala Lys Asp Lys Val Pro Asn Asn Leu Lys Ala Gln
        355                 360                 365

Glu Gly Lys Val Arg Thr Asn Ser Asp Arg Lys Ser Pro Gly Ser Leu
    370                 375                 380

Pro Lys Val Glu Glu Met Asp Met Asp Asp Glu Phe Glu Gln Pro Thr
385                 390                 395                 400
```

```
Met Ser Phe Glu Ser Tyr Leu Ser Tyr Asp Gln Pro Arg Lys Lys Lys
                405                 410                 415
Lys Lys Val Val Lys Thr Ser Gly Thr Ala Leu Gly Glu Lys Gly Leu
            420                 425                 430
Lys Lys Lys Asp Ser Lys Ser Thr Ser Lys Asn Leu Asn Ser Ala Gln
        435                 440                 445
Lys Leu Pro Lys Ala Asn Glu Asn Lys Ser Asp Lys Leu Gln Pro Ala
    450                 455                 460
Gly Ala Glu Pro Thr Arg Pro Arg Lys Val Pro Thr Asp Val Leu Pro
465                 470                 475                 480
Ala Leu Pro Asp Ile Pro Leu Pro Ala Ile Gln Thr Asn Tyr Arg Pro
                485                 490                 495
Leu Pro Ser Leu Glu Leu Ile Ser Ser Phe Gln Pro Lys Arg Lys Ala
                500                 505                 510
Phe Ser Ser Pro Gln Glu Glu Glu Ala Gly Phe Thr Gly Arg Arg
            515                 520                 525
Met Asn Ser Lys Met Gln Val Tyr Ser Gly Ser Lys Cys Ala Tyr Leu
        530                 535                 540
Pro Lys Met Met Thr Leu His Gln Gln Cys Ile Arg Val Leu Lys Asn
545                 550                 555                 560
Asn Ile Asp Ser Ile Phe Glu Val Gly Gly Val Pro Tyr Ser Val Leu
                565                 570                 575
Glu Pro Val Leu Glu Arg Cys Thr Pro His Arg Asp Phe Lys Glu Glu
                580                 585                 590
Arg Pro Glu Glu Tyr Glu Ser Trp Arg Glu Met Tyr Leu Arg Leu Gln
            595                 600                 605
Asp Ala Arg Glu Gln Arg Leu Arg Leu Leu Thr Asn Asn Ile Arg Ser
        610                 615                 620
Ala His Ala Asn Lys Pro Lys Gly Arg Gln Ala Lys Met Ala Phe Val
625                 630                 635                 640
Asn Ser Val Ala Lys Pro Pro Arg Asp Val Arg Arg Gln Glu Lys
                645                 650                 655
Phe Gly Thr Gly Gly Ala Ala Val Pro Glu Lys Val Arg Ile Lys Pro
            660                 665                 670
Ala Pro Tyr Thr Thr Gly Ser Ser His Val Pro Ala Ser Asn Ser Ser
        675                 680                 685
Ser Ser Phe His Ser Ser Pro Glu Glu Leu Ala Tyr Glu Gly Pro Ser
    690                 695                 700
Thr Ser Ser Ala His Leu Ala Pro Val Ala Ser Ser Val Ser Tyr
705                 710                 715                 720
Asp Pro Arg Lys Pro Ala Val Lys Lys Ile Ala Pro Met Met Ala Lys
                725                 730                 735
Thr Ile Lys Ala Phe Lys Asn Arg Phe Ser Arg Arg
                740                 745
```

(2) INFORMATION FOR SEQ ID NO:28:

(i) SEQUENCE CHARACTERISTICS:
        (A) LENGTH: 733 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein (B) LOCATION: 1..733
(D) OTHER INFORMATION: /note= "amino acids 1-610 and 651-773 of Elongin A"

(xi) SEQUENCE DESCRIPTION: SEQ ID NO:28:

```
Met Ala Ala Glu Ser Ala Leu Gln Val Val Glu Lys Leu Gln Ala Arg
1               5                   10                  15

Leu Ala Ala Asn Pro Asp Pro Lys Lys Leu Leu Lys Tyr Leu Lys Lys
            20                  25                  30

Leu Ser Val Leu Pro Ile Thr Val Asp Ile Leu Val Glu Thr Gly Val
        35                  40                  45

Gly Lys Thr Val Asn Ser Phe Arg Lys His Glu Gln Val Gly Asn Phe
    50                  55                  60

Ala Arg Asp Leu Val Ala Gln Trp Lys Lys Leu Val Pro Val Glu Arg
65                  70                  75                  80

Asn Asn Glu Ala Glu Asp Gln Asp Phe Glu Lys Ser Asn Ser Arg Lys
                85                  90                  95

Arg Pro Arg Asp Val Pro Gln Gln Glu Glu Ala Glu Gly Asn Tyr
            100                 105                 110

Gln Glu Ser Trp Gln Ala Ser Gly Ser Gln Pro Tyr Ser Pro Glu His
            115                 120                 125

Arg Gln Lys Lys His Arg Lys Leu Pro Glu Leu Glu Arg Pro His Lys
        130                 135                 140

Val Ala His Gly His Glu Arg Arg Asp Glu Arg Lys Arg Cys His Lys
145                 150                 155                 160

Val Ser Pro Pro Tyr Ser Ser Asp Pro Glu Ser Ser Asp Tyr Gly His
                165                 170                 175

Val Gln Ser Pro Pro Ser Ser Pro His Gln Met Tyr Thr Asp Leu
            180                 185                 190

Ser Arg Ser Pro Glu Met Asp Gln Glu Pro Ile Val Ser His Pro Lys
        195                 200                 205

Pro Gly Lys Val His Ser Asn Thr Phe Gln Asp Arg Leu Gly Val Ser
    210                 215                 220

His Leu Gly Glu His Gln Gly Lys Gly Ala Val Ser Gln Asn Lys Pro
225                 230                 235                 240

His Lys Ser Ser His Lys Glu Lys Arg Pro Val Asp Ala Arg Gly Asp
                245                 250                 255

Glu Lys Ser Ser Val Met Gly Arg Glu Lys Ser His Lys Ala Ser Ser
            260                 265                 270

Lys Glu Glu Ser Arg Arg Leu Leu Ser Glu Asp Ser Ala Lys Glu Lys
        275                 280                 285

Leu Pro Ser Ser Val Val Lys Lys Glu Lys Asp Arg Glu Gly Asn Ser
    290                 295                 300

Leu Lys Lys Lys Leu Ser Pro Ala Leu Asp Val Ala Ser Asp Asn His
305                 310                 315                 320

Phe Lys Lys Pro Lys His Lys Asp Ser Glu Lys Ile Lys Ser Asp Lys
                325                 330                 335

Asn Lys Gln Ser Val Asp Ser Val Asp Ser Gly Arg Gly Thr Gly Asp
            340                 345                 350

Pro Leu Pro Arg Ala Lys Asp Lys Val Pro Asn Asn Leu Lys Ala Gln
        355                 360                 365

Glu Gly Lys Val Arg Thr Asn Ser Asp Arg Lys Ser Pro Gly Ser Leu
    370                 375                 380

Pro Lys Val Glu Glu Met Asp Met Asp Asp Glu Phe Glu Gln Pro Thr
```

```
            385                 390                 395                 400
    Met Ser Phe Glu Ser Tyr Leu Ser Tyr Asp Gln Pro Arg Lys Lys Lys
                    405                 410                 415

Lys Lys Val Val Lys Thr Ser Gly Thr Ala Leu Gly Glu Lys Gly Leu
                420                 425                 430

Lys Lys Lys Asp Ser Lys Ser Thr Ser Lys Asn Leu Asn Ser Ala Gln
                435                 440                 445

Lys Leu Pro Lys Ala Asn Glu Asn Lys Ser Asp Lys Leu Gln Pro Ala
                450                 455                 460

Gly Ala Glu Pro Thr Arg Pro Arg Lys Val Pro Thr Asp Val Leu Pro
    465                 470                 475                 480

Ala Leu Pro Asp Ile Pro Leu Pro Ala Ile Gln Thr Asn Tyr Arg Pro
                    485                 490                 495

Leu Pro Ser Leu Glu Leu Ile Ser Ser Phe Gln Pro Lys Arg Lys Ala
                    500                 505                 510

Phe Ser Ser Pro Gln Glu Glu Glu Ala Gly Phe Thr Gly Arg Arg
                515                 520                 525

Met Asn Ser Lys Met Gln Val Tyr Ser Gly Ser Lys Cys Ala Tyr Leu
                530                 535                 540

Pro Lys Met Met Thr Leu His Gln Gln Cys Ile Arg Val Leu Lys Asn
    545                 550                 555                 560

Asn Ile Asp Ser Ile Phe Glu Val Gly Val Pro Tyr Ser Val Leu
                    565                 570                 575

Glu Pro Val Leu Glu Arg Cys Thr Pro Asp Gln Leu Tyr Arg Ile Glu
                580                 585                 590

Glu Cys Asn His Val Leu Ile Glu Glu Thr Asp Gln Leu Trp Lys Val
                595                 600                 605

His Cys His Ala Asn Lys Pro Lys Gly Arg Gln Ala Lys Met Ala Phe
                610                 615                 620

Val Asn Ser Val Ala Lys Pro Pro Arg Asp Val Arg Arg Gln Glu
    625                 630                 635                 640

Lys Phe Gly Thr Gly Gly Ala Ala Val Pro Glu Lys Val Arg Ile Lys
                    645                 650                 655

Pro Ala Pro Tyr Thr Thr Gly Ser Ser His Val Pro Ala Ser Asn Ser
                    660                 665                 670

Ser Ser Ser Phe His Ser Ser Pro Glu Glu Leu Ala Tyr Glu Gly Pro
                675                 680                 685

Ser Thr Ser Ser Ala His Leu Ala Pro Val Ala Ser Ser Val Ser
                690                 695                 700

Tyr Asp Pro Arg Lys Pro Ala Val Lys Lys Ile Ala Pro Met Met Ala
    705                 710                 715                 720

Lys Thr Ile Lys Ala Phe Lys Asn Arg Phe Ser Arg Arg
                    725                 730
```

(2) INFORMATION FOR SEQ ID NO:29:

(i) SEQUENCE CHARACTERISTICS:
        (A) LENGTH: 733 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..733

(D) OTHER INFORMATION: /note= "amino acids 1-650 and 691-773 of Elongin A"

(xi) SEQUENCE DESCRIPTION: SEQ ID NO:29:

```
Met Ala Ala Glu Ser Ala Leu Gln Val Val Glu Lys Leu Gln Ala Arg
1               5                   10                  15

Leu Ala Ala Asn Pro Asp Pro Lys Lys Leu Leu Lys Tyr Leu Lys Lys
            20                  25                  30

Leu Ser Val Leu Pro Ile Thr Val Asp Ile Leu Val Glu Thr Gly Val
        35                  40                  45

Gly Lys Thr Val Asn Ser Phe Arg Lys His Glu Gln Val Gly Asn Phe
    50                  55                  60

Ala Arg Asp Leu Val Ala Gln Trp Lys Lys Leu Val Pro Val Glu Arg
65                  70                  75                  80

Asn Asn Glu Ala Glu Asp Gln Asp Phe Glu Lys Ser Asn Ser Arg Lys
                85                  90                  95

Arg Pro Arg Asp Val Pro Gln Gln Glu Glu Ala Glu Gly Asn Tyr
            100                 105                 110

Gln Glu Ser Trp Gln Ala Ser Gly Ser Gln Pro Tyr Ser Pro Glu His
            115                 120                 125

Arg Gln Lys Lys His Arg Lys Leu Pro Glu Leu Glu Arg Pro His Lys
    130                 135                 140

Val Ala His Gly His Glu Arg Arg Asp Glu Arg Lys Arg Cys His Lys
145                 150                 155                 160

Val Ser Pro Pro Tyr Ser Ser Asp Pro Glu Ser Ser Asp Tyr Gly His
                165                 170                 175

Val Gln Ser Pro Pro Ser Ser Pro His Gln Met Tyr Thr Asp Leu
            180                 185                 190

Ser Arg Ser Pro Glu Met Asp Gln Glu Pro Ile Val Ser His Pro Lys
    195                 200                 205

Pro Gly Lys Val His Ser Asn Thr Phe Gln Asp Arg Leu Gly Val Ser
    210                 215                 220

His Leu Gly Glu His Gln Gly Lys Gly Ala Val Ser Gln Asn Lys Pro
225                 230                 235                 240

His Lys Ser Ser His Lys Glu Lys Arg Pro Val Asp Ala Arg Gly Asp
                245                 250                 255

Glu Lys Ser Ser Val Met Gly Arg Glu Lys Ser His Lys Ala Ser Ser
            260                 265                 270

Lys Glu Glu Ser Arg Arg Leu Leu Ser Glu Asp Ser Ala Lys Glu Lys
    275                 280                 285

Leu Pro Ser Ser Val Val Lys Lys Glu Lys Asp Arg Glu Gly Asn Ser
290                 295                 300

Leu Lys Lys Lys Leu Ser Pro Ala Leu Asp Val Ala Ser Asp Asn His
305                 310                 315                 320

Phe Lys Lys Pro Lys His Lys Asp Ser Glu Lys Ile Lys Ser Asp Lys
                325                 330                 335

Asn Lys Gln Ser Val Asp Ser Val Asp Ser Gly Arg Gly Thr Gly Asp
            340                 345                 350

Pro Leu Pro Arg Ala Lys Asp Lys Val Pro Asn Asn Leu Lys Ala Gln
    355                 360                 365

Glu Gly Lys Val Arg Thr Asn Ser Asp Arg Lys Ser Pro Gly Ser Leu
    370                 375                 380

Pro Lys Val Glu Glu Met Asp Met Asp Asp Glu Phe Glu Gln Pro Thr
385                 390                 395                 400
```

```
            Met Ser Phe Glu Ser Tyr Leu Ser Tyr Asp Gln Pro Arg Lys Lys Lys
                            405                 410                 415

Lys Lys Val Val Lys Thr Ser Gly Thr Ala Leu Gly Glu Lys Gly Leu
                        420                 425                 430

Lys Lys Lys Asp Ser Lys Ser Thr Ser Lys Asn Leu Asn Ser Ala Gln
                        435                 440                 445

Lys Leu Pro Lys Ala Asn Glu Asn Lys Ser Asp Lys Leu Gln Pro Ala
                        450                 455                 460

Gly Ala Glu Pro Thr Arg Pro Arg Lys Val Pro Thr Asp Val Leu Pro
            465                 470                 475                 480

Ala Leu Pro Asp Ile Pro Leu Pro Ala Ile Gln Thr Asn Tyr Arg Pro
                            485                 490                 495

Leu Pro Ser Leu Glu Leu Ile Ser Ser Phe Gln Pro Lys Arg Lys Ala
                            500                 505                 510

Phe Ser Ser Pro Gln Glu Glu Glu Ala Gly Phe Thr Gly Arg Arg
                            515                 520                 525

Met Asn Ser Lys Met Gln Val Tyr Ser Gly Ser Lys Cys Ala Tyr Leu
                            530                 535                 540

Pro Lys Met Met Thr Leu His Gln Gln Cys Ile Arg Val Leu Lys Asn
            545                 550                 555                 560

Asn Ile Asp Ser Ile Phe Glu Val Gly Gly Val Pro Tyr Ser Val Leu
                            565                 570                 575

Glu Pro Val Leu Glu Arg Cys Thr Pro Asp Gln Leu Tyr Arg Ile Glu
                            580                 585                 590

Glu Cys Asn His Val Leu Ile Glu Glu Thr Asp Gln Leu Trp Lys Val
                            595                 600                 605

His Cys His Arg Asp Phe Lys Glu Glu Arg Pro Glu Glu Tyr Glu Ser
                            610                 615                 620

Trp Arg Glu Met Tyr Leu Arg Leu Gln Asp Ala Arg Glu Gln Arg Leu
            625                 630                 635                 640

Arg Leu Leu Thr Asn Asn Ile Arg Ser Ala Glu Lys Val Arg Ile Lys
                            645                 650                 655

Pro Ala Pro Tyr Thr Thr Gly Ser Ser His Val Pro Ala Ser Asn Ser
                            660                 665                 670

Ser Ser Ser Phe His Ser Ser Pro Glu Glu Leu Ala Tyr Glu Gly Pro
                            675                 680                 685

Ser Thr Ser Ser Ala His Leu Ala Pro Val Ala Ser Ser Ser Val Ser
                            690                 695                 700

Tyr Asp Pro Arg Lys Pro Ala Val Lys Lys Ile Ala Pro Met Met Ala
            705                 710                 715                 720

Lys Thr Ile Lys Ala Phe Lys Asn Arg Phe Ser Arg Arg
                            725                 730

(2) INFORMATION FOR SEQ ID NO:30:

(i) SEQUENCE CHARACTERISTICS:
        (A) LENGTH: 733 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..733
        (D) OTHER INFORMATION: /note= "amino acids 1-690 and
```

731-773 of Elongin A"

(xi) SEQUENCE DESCRIPTION: SEQ ID NO:30:

```
Met Ala Ala Glu Ser Ala Leu Gln Val Val Glu Lys Leu Gln Ala Arg
 1               5                  10                  15

Leu Ala Ala Asn Pro Asp Pro Lys Lys Leu Leu Lys Tyr Leu Lys Lys
             20                  25                  30

Leu Ser Val Leu Pro Ile Thr Val Asp Ile Leu Val Glu Thr Gly Val
         35                  40                  45

Gly Lys Thr Val Asn Ser Phe Arg Lys His Glu Gln Val Gly Asn Phe
     50                  55                  60

Ala Arg Asp Leu Val Ala Gln Trp Lys Lys Leu Val Pro Val Glu Arg
 65                  70                  75                  80

Asn Asn Glu Ala Glu Asp Gln Asp Phe Glu Lys Ser Asn Ser Arg Lys
                 85                  90                  95

Arg Pro Arg Asp Val Pro Gln Gln Glu Glu Ala Glu Gly Asn Tyr
            100                 105                 110

Gln Glu Ser Trp Gln Ala Ser Gly Ser Gln Pro Tyr Ser Pro Glu His
            115                 120                 125

Arg Gln Lys Lys His Arg Lys Leu Pro Glu Leu Glu Arg Pro His Lys
130                 135                 140

Val Ala His Gly His Glu Arg Arg Asp Glu Arg Lys Arg Cys His Lys
145                 150                 155                 160

Val Ser Pro Pro Tyr Ser Ser Asp Pro Glu Ser Ser Asp Tyr Gly His
                165                 170                 175

Val Gln Ser Pro Pro Ser Ser Pro His Gln Met Tyr Thr Asp Leu
            180                 185                 190

Ser Arg Ser Pro Glu Met Asp Gln Glu Pro Ile Val Ser His Pro Lys
            195                 200                 205

Pro Gly Lys Val His Ser Asn Thr Phe Gln Asp Arg Leu Gly Val Ser
210                 215                 220

His Leu Gly Glu His Gln Gly Lys Gly Ala Val Ser Gln Asn Lys Pro
225                 230                 235                 240

His Lys Ser Ser His Lys Glu Lys Arg Pro Val Asp Ala Arg Gly Asp
                245                 250                 255

Glu Lys Ser Ser Val Met Gly Arg Glu Lys Ser His Lys Ala Ser Ser
            260                 265                 270

Lys Glu Glu Ser Arg Arg Leu Leu Ser Glu Asp Ser Ala Lys Glu Lys
            275                 280                 285

Leu Pro Ser Ser Val Val Lys Lys Glu Lys Asp Arg Glu Gly Asn Ser
            290                 295                 300

Leu Lys Lys Lys Leu Ser Pro Ala Leu Asp Val Ala Ser Asp Asn His
305                 310                 315                 320

Phe Lys Lys Pro Lys His Lys Asp Ser Glu Lys Ile Lys Ser Asp Lys
                325                 330                 335

Asn Lys Gln Ser Val Asp Ser Val Asp Ser Gly Arg Gly Thr Gly Asp
            340                 345                 350

Pro Leu Pro Arg Ala Lys Asp Lys Val Pro Asn Asn Leu Lys Ala Gln
            355                 360                 365

Glu Gly Lys Val Arg Thr Asn Ser Asp Arg Lys Ser Pro Gly Ser Leu
370                 375                 380

Pro Lys Val Glu Glu Met Asp Met Asp Asp Glu Phe Glu Gln Pro Thr
385                 390                 395                 400
```

```
Met Ser Phe Glu Ser Tyr Leu Ser Tyr Asp Gln Pro Arg Lys Lys Lys
                405                 410                 415
Lys Lys Val Val Lys Thr Ser Gly Thr Ala Leu Gly Glu Lys Gly Leu
            420                 425                 430
Lys Lys Lys Asp Ser Lys Ser Thr Ser Lys Asn Leu Asn Ser Ala Gln
        435                 440                 445
Lys Leu Pro Lys Ala Asn Glu Asn Lys Ser Asp Lys Leu Gln Pro Ala
    450                 455                 460
Gly Ala Glu Pro Thr Arg Pro Arg Lys Val Pro Thr Asp Val Leu Pro
465                 470                 475                 480
Ala Leu Pro Asp Ile Pro Leu Pro Ala Ile Gln Thr Asn Tyr Arg Pro
                485                 490                 495
Leu Pro Ser Leu Glu Leu Ile Ser Ser Phe Gln Pro Lys Arg Lys Ala
                500                 505                 510
Phe Ser Ser Pro Gln Glu Glu Glu Ala Gly Phe Thr Gly Arg Arg
                515                 520                 525
Met Asn Ser Lys Met Gln Val Tyr Ser Gly Ser Lys Cys Ala Tyr Leu
            530                 535                 540
Pro Lys Met Met Thr Leu His Gln Gln Cys Ile Arg Val Leu Lys Asn
545                 550                 555                 560
Asn Ile Asp Ser Ile Phe Glu Val Gly Gly Val Pro Tyr Ser Val Leu
                565                 570                 575
Glu Pro Val Leu Glu Arg Cys Thr Pro Asp Gln Leu Tyr Arg Ile Glu
                580                 585                 590
Glu Cys Asn His Val Leu Ile Glu Glu Thr Asp Gln Leu Trp Lys Val
            595                 600                 605
His Cys His Arg Asp Phe Lys Glu Glu Arg Pro Glu Glu Tyr Glu Ser
        610                 615                 620
Trp Arg Glu Met Tyr Leu Arg Leu Gln Asp Ala Arg Glu Gln Arg Leu
625                 630                 635                 640
Arg Leu Leu Thr Asn Asn Ile Arg Ser Ala His Ala Asn Lys Pro Lys
                645                 650                 655
Gly Arg Gln Ala Lys Met Ala Phe Val Asn Ser Val Ala Lys Pro Pro
                660                 665                 670
Arg Asp Val Arg Arg Gln Glu Lys Phe Gly Thr Gly Gly Ala Ala
            675                 680                 685
Val Pro Ser Ser Ala His Leu Ala Pro Val Ala Ser Ser Val Ser
            690                 695                 700
Tyr Asp Pro Arg Lys Pro Ala Val Lys Lys Ile Ala Pro Met Met Ala
705                 710                 715                 720
Lys Thr Ile Lys Ala Phe Lys Asn Arg Phe Ser Arg Arg
                725                 730
```

(2) INFORMATION FOR SEQ ID NO:31:

(i) SEQUENCE CHARACTERISTICS:
        (A) LENGTH: 170 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Peptide
        (B) LOCATION: 1..170
        (D) OTHER INFORMATION: /note= "amino acids 521-690 of
            Elongin A"

(xi) SEQUENCE DESCRIPTION: SEQ ID NO:31:

```
Glu Ala Gly Phe Thr Gly Arg Arg Met Asn Ser Lys Met Gln Val Tyr
1               5                   10                  15

Ser Gly Ser Lys Cys Ala Tyr Leu Pro Lys Met Met Thr Leu His Gln
            20                  25                  30

Gln Cys Ile Arg Val Leu Lys Asn Asn Ile Asp Ser Ile Phe Glu Val
        35                  40                  45

Gly Gly Val Pro Tyr Ser Val Leu Glu Pro Val Leu Glu Arg Cys Thr
    50                  55                  60

Pro Asp Gln Leu Tyr Arg Ile Glu Glu Cys Asn His Val Leu Ile Glu
65                  70                  75                  80

Glu Thr Asp Gln Leu Trp Lys Val His Cys His Arg Asp Phe Lys Glu
                85                  90                  95

Glu Arg Pro Glu Glu Tyr Glu Ser Trp Arg Glu Met Tyr Leu Arg Leu
            100                 105                 110

Gln Asp Ala Arg Glu Gln Arg Leu Arg Leu Leu Thr Asn Asn Ile Arg
        115                 120                 125

Ser Ala His Ala Asn Lys Pro Lys Gly Arg Gln Ala Lys Met Ala Phe
    130                 135                 140

Val Asn Ser Val Ala Lys Pro Pro Arg Asp Val Arg Arg Arg Gln Glu
145                 150                 155                 160

Lys Phe Gly Thr Gly Gly Ala Ala Val Pro
                165                 170
```

(2) INFORMATION FOR SEQ ID NO:32:

(i) SEQUENCE CHARACTERISTICS:
        (A) LENGTH: 231 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..231
        (D) OTHER INFORMATION: /note= "amino acids 500-730 of
            Elongin A"

(xi) SEQUENCE DESCRIPTION: SEQ ID NO:32:

```
Leu Glu Leu Ile Ser Ser Phe Gln Pro Lys Arg Lys Ala Phe Ser Ser
1               5                   10                  15

Pro Gln Glu Glu Glu Glu Ala Gly Phe Thr Gly Arg Arg Met Asn Ser
            20                  25                  30

Lys Met Gln Val Tyr Ser Gly Ser Lys Cys Ala Tyr Leu Pro Lys Met
        35                  40                  45

Met Thr Leu His Gln Gln Cys Ile Arg Val Leu Lys Asn Asn Ile Asp
    50                  55                  60

Ser Ile Phe Glu Val Gly Gly Val Pro Tyr Ser Val Leu Glu Pro Val
65                  70                  75                  80

Leu Glu Arg Cys Thr Pro Asp Gln Leu Tyr Arg Ile Glu Glu Cys Asn
                85                  90                  95

His Val Leu Ile Glu Glu Thr Asp Gln Leu Trp Lys Val His Cys His
            100                 105                 110

Arg Asp Phe Lys Glu Glu Arg Pro Glu Glu Tyr Glu Ser Trp Arg Glu
        115                 120                 125
```

```
Met Tyr Leu Arg Leu Gln Asp Ala Arg Glu Gln Arg Leu Arg Leu Leu
    130                 135                 140

Thr Asn Asn Ile Arg Ser Ala His Ala Asn Lys Pro Lys Gly Arg Gln
145                 150                 155                 160

Ala Lys Met Ala Phe Val Asn Ser Val Ala Lys Pro Pro Arg Asp Val
                165                 170                 175

Arg Arg Arg Gln Glu Lys Phe Gly Thr Gly Gly Ala Ala Val Pro Glu
            180                 185                 190

Lys Val Arg Ile Lys Pro Ala Pro Tyr Thr Thr Gly Ser Ser His Val
        195                 200                 205

Pro Ala Ser Asn Ser Ser Ser Phe His Ser Ser Pro Glu Glu Leu
    210                 215                 220

Ala Tyr Glu Gly Pro Ser Thr
225                 230
```

(2) INFORMATION FOR SEQ ID NO:33:

(i) SEQUENCE CHARACTERISTICS:
        (A) LENGTH: 201 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..201
        (D) OTHER INFORMATION: /note= "amino acids 500-700 of
            Elongin A"

(xi) SEQUENCE DESCRIPTION: SEQ ID NO:33:

```
Leu Glu Leu Ile Ser Ser Phe Gln Pro Lys Arg Lys Ala Phe Ser Ser
1               5                   10                  15

Pro Gln Glu Glu Glu Ala Gly Phe Thr Gly Arg Arg Met Asn Ser
            20                  25                  30

Lys Met Gln Val Tyr Ser Gly Ser Lys Cys Ala Tyr Leu Pro Lys Met
        35                  40                  45

Met Thr Leu His Gln Gln Cys Ile Arg Val Leu Lys Asn Asn Ile Asp
    50                  55                  60

Ser Ile Phe Glu Val Gly Gly Val Pro Tyr Ser Val Leu Glu Pro Val
65                  70                  75                  80

Leu Glu Arg Cys Thr Pro Asp Gln Leu Tyr Arg Ile Glu Glu Cys Asn
                85                  90                  95

His Val Leu Ile Glu Glu Thr Asp Gln Leu Trp Lys Val His Cys His
            100                 105                 110

Arg Asp Phe Lys Glu Glu Arg Pro Glu Glu Tyr Glu Ser Trp Arg Glu
        115                 120                 125

Met Tyr Leu Arg Leu Gln Asp Ala Arg Glu Gln Arg Leu Arg Leu Leu
    130                 135                 140

Thr Asn Asn Ile Arg Ser Ala His Ala Asn Lys Pro Lys Gly Arg Gln
145                 150                 155                 160

Ala Lys Met Ala Phe Val Asn Ser Val Ala Lys Pro Pro Arg Asp Val
                165                 170                 175

Arg Arg Arg Gln Glu Lys Phe Gly Thr Gly Gly Ala Ala Val Pro Glu
            180                 185                 190

Lys Val Arg Ile Lys Pro Ala Pro Tyr
        195                 200
```

(2) INFORMATION FOR SEQ ID NO:34:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..24
        (D) OTHER INFORMATION: /note= "amino acids 545-568 of
            Elongin A"

(xi) SEQUENCE DESCRIPTION: SEQ ID NO:34:

```
Pro Lys Met Met Thr Leu His Gln Gln Cys Ile Arg Val Leu Lys Asn
1               5                   10                  15

Asn Ile Asp Ser Ile Phe Glu Val
            20
```

(2) INFORMATION FOR SEQ ID NO:35:

(i) SEQUENCE CHARACTERISTICS:
        (A) LENGTH: 769 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..769
        (D) OTHER INFORMATION: /note= "amino acids 1-544 and
            549-773 of Elongin A"

(xi) SEQUENCE DESCRIPTION: SEQ ID NO:35:

```
Met Ala Ala Glu Ser Ala Leu Gln Val Val Glu Lys Leu Gln Ala Arg
1               5                   10                  15

Leu Ala Ala Asn Pro Asp Pro Lys Lys Leu Leu Lys Tyr Leu Lys Lys
                20                  25                  30

Leu Ser Val Leu Pro Ile Thr Val Asp Ile Leu Val Glu Thr Gly Val
            35                  40                  45

Gly Lys Thr Val Asn Ser Phe Arg Lys His Glu Gln Val Gly Asn Phe
    50                  55                  60

Ala Arg Asp Leu Val Ala Gln Trp Lys Lys Leu Val Pro Val Glu Arg
65                  70                  75                  80

Asn Asn Glu Ala Glu Asp Gln Asp Phe Glu Lys Ser Asn Ser Arg Lys
                85                  90                  95

Arg Pro Arg Asp Val Pro Gln Gln Glu Glu Ala Glu Gly Asn Tyr
            100                 105                 110

Gln Glu Ser Trp Gln Ala Ser Gly Ser Gln Pro Tyr Ser Pro Glu His
    115                 120                 125

Arg Gln Lys Lys His Arg Lys Leu Pro Glu Leu Glu Arg Pro His Lys
    130                 135                 140

Val Ala His Gly His Glu Arg Arg Asp Glu Arg Lys Arg Cys His Lys
145                 150                 155                 160

Val Ser Pro Pro Tyr Ser Ser Asp Pro Glu Ser Ser Asp Tyr Gly His
                165                 170                 175

Val Gln Ser Pro Pro Ser Ser Pro His Gln Met Tyr Thr Asp Leu
            180                 185                 190
```

```
Ser Arg Ser Pro Glu Met Asp Gln Glu Pro Ile Val Ser His Pro Lys
        195                 200                 205

Pro Gly Lys Val His Ser Asn Thr Phe Gln Asp Arg Leu Gly Val Ser
        210                 215                 220

His Leu Gly Glu His Gln Gly Lys Gly Ala Val Ser Gln Asn Lys Pro
225                 230                 235                 240

His Lys Ser Ser His Lys Glu Lys Arg Pro Val Asp Ala Arg Gly Asp
                245                 250                 255

Glu Lys Ser Ser Val Met Gly Arg Glu Lys Ser His Lys Ala Ser Ser
            260                 265                 270

Lys Glu Glu Ser Arg Arg Leu Leu Ser Glu Asp Ser Ala Lys Glu Lys
        275                 280                 285

Leu Pro Ser Ser Val Val Lys Lys Glu Lys Asp Arg Glu Gly Asn Ser
290                 295                 300

Leu Lys Lys Lys Leu Ser Pro Ala Leu Asp Val Ala Ser Asp Asn His
305                 310                 315                 320

Phe Lys Lys Pro Lys His Lys Asp Ser Glu Lys Ile Lys Ser Asp Lys
                325                 330                 335

Asn Lys Gln Ser Val Asp Ser Val Asp Ser Gly Arg Gly Thr Gly Asp
            340                 345                 350

Pro Leu Pro Arg Ala Lys Asp Lys Val Pro Asn Asn Leu Lys Ala Gln
        355                 360                 365

Glu Gly Lys Val Arg Thr Asn Ser Asp Arg Lys Ser Pro Gly Ser Leu
        370                 375                 380

Pro Lys Val Glu Glu Met Asp Met Asp Asp Glu Phe Glu Gln Pro Thr
385                 390                 395                 400

Met Ser Phe Glu Ser Tyr Leu Ser Tyr Asp Gln Pro Arg Lys Lys Lys
                405                 410                 415

Lys Lys Val Val Lys Thr Ser Gly Thr Ala Leu Gly Glu Lys Gly Leu
            420                 425                 430

Lys Lys Lys Asp Ser Lys Ser Thr Ser Lys Asn Leu Asn Ser Ala Gln
        435                 440                 445

Lys Leu Pro Lys Ala Asn Glu Asn Lys Ser Asp Lys Leu Gln Pro Ala
        450                 455                 460

Gly Ala Glu Pro Thr Arg Pro Arg Lys Val Pro Thr Asp Val Leu Pro
465                 470                 475                 480

Ala Leu Pro Asp Ile Pro Leu Pro Ala Ile Gln Thr Asn Tyr Arg Pro
                485                 490                 495

Leu Pro Ser Leu Glu Leu Ile Ser Ser Phe Gln Pro Lys Arg Lys Ala
            500                 505                 510

Phe Ser Ser Pro Gln Glu Glu Glu Ala Gly Phe Thr Gly Arg Arg
        515                 520                 525

Met Asn Ser Lys Met Gln Val Tyr Ser Gly Ser Lys Cys Ala Tyr Leu
        530                 535                 540

Thr Leu His Gln Gln Cys Ile Arg Val Leu Lys Asn Asn Ile Asp Ser
545                 550                 555                 560

Ile Phe Glu Val Gly Gly Val Pro Tyr Ser Val Leu Glu Pro Val Leu
                565                 570                 575

Glu Arg Cys Thr Pro Asp Gln Leu Tyr Arg Ile Glu Glu Cys Asn His
            580                 585                 590

Val Leu Ile Glu Glu Thr Asp Gln Leu Trp Lys Val His Cys His Arg
        595                 600                 605
```

```
Asp Phe Lys Glu Glu Arg Pro Glu Glu Tyr Glu Ser Trp Arg Glu Met
    610                 615                 620
Tyr Leu Arg Leu Gln Asp Ala Arg Glu Gln Arg Leu Arg Leu Leu Thr
625                 630                 635                 640
Asn Asn Ile Arg Ser Ala His Ala Asn Lys Pro Lys Gly Arg Gln Ala
                645                 650                 655
Lys Met Ala Phe Val Asn Ser Val Ala Lys Pro Pro Arg Asp Val Arg
                660                 665                 670
Arg Arg Gln Glu Lys Phe Gly Thr Gly Gly Ala Ala Val Pro Glu Lys
            675                 680                 685
Val Arg Ile Lys Pro Ala Pro Tyr Thr Thr Gly Ser Ser His Val Pro
    690                 695                 700
Ala Ser Asn Ser Ser Ser Ser Phe His Ser Ser Pro Glu Glu Leu Ala
705                 710                 715                 720
Tyr Glu Gly Pro Ser Thr Ser Ser Ala His Leu Ala Pro Val Ala Ser
                725                 730                 735
Ser Ser Val Ser Tyr Asp Pro Arg Lys Pro Ala Val Lys Lys Ile Ala
                740                 745                 750
Pro Met Met Ala Lys Thr Ile Lys Ala Phe Lys Asn Arg Phe Ser Arg
            755                 760                 765
Arg (2) INFORMATION FOR SEQ ID NO:36:

(i) SEQUENCE CHARACTERISTICS:
        (A) LENGTH: 769 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..769
        (D) OTHER INFORMATION: /note= "amino acids 1-548 and
            553-773 of Elongin A"

(xi) SEQUENCE DESCRIPTION: SEQ ID NO:36:

Met Ala Ala Glu Ser Ala Leu Gln Val Val Glu Lys Leu Gln Ala Arg
1               5                   10                  15
Leu Ala Ala Asn Pro Asp Pro Lys Lys Leu Leu Lys Tyr Leu Lys Lys
                20                  25                  30
Leu Ser Val Leu Pro Ile Thr Val Asp Ile Leu Val Glu Thr Gly Val
            35                  40                  45
Gly Lys Thr Val Asn Ser Phe Arg Lys His Glu Gln Val Gly Asn Phe
    50                  55                  60
Ala Arg Asp Leu Val Ala Gln Trp Lys Lys Leu Val Pro Val Glu Arg
65                  70                  75                  80
Asn Asn Glu Ala Glu Asp Gln Asp Phe Glu Lys Ser Asn Ser Arg Lys
                85                  90                  95
Arg Pro Arg Asp Val Pro Gln Gln Glu Glu Ala Glu Gly Asn Tyr
                100                 105                 110
Gln Glu Ser Trp Gln Ala Ser Gly Ser Gln Pro Tyr Ser Pro Glu His
            115                 120                 125
Arg Gln Lys Lys His Arg Lys Leu Pro Glu Leu Glu Arg Pro His Lys
    130                 135                 140
Val Ala His Gly His Glu Arg Arg Asp Glu Arg Lys Arg Cys His Lys
```

```
            145                 150                 155                 160
        Val Ser Pro Pro Tyr Ser Ser Asp Pro Glu Ser Ser Asp Tyr Gly His
                        165                 170                 175
        Val Gln Ser Pro Pro Ser Ser Pro His Gln Met Tyr Thr Asp Leu
                    180                 185                 190
        Ser Arg Ser Pro Glu Met Asp Gln Glu Pro Ile Val Ser His Pro Lys
                        195                 200                 205
        Pro Gly Lys Val His Ser Asn Thr Phe Gln Asp Arg Leu Gly Val Ser
                    210                 215                 220
        His Leu Gly Glu His Gln Gly Lys Gly Ala Val Ser Gln Asn Lys Pro
        225                 230                 235                 240
        His Lys Ser Ser His Lys Glu Lys Arg Pro Val Asp Ala Arg Gly Asp
                        245                 250                 255
        Glu Lys Ser Ser Val Met Gly Arg Glu Lys Ser His Lys Ala Ser Ser
                    260                 265                 270
        Lys Glu Glu Ser Arg Arg Leu Leu Ser Glu Asp Ser Ala Lys Glu Lys
                    275                 280                 285
        Leu Pro Ser Ser Val Val Lys Lys Glu Lys Asp Arg Glu Gly Asn Ser
        290                 295                 300
        Leu Lys Lys Lys Leu Ser Pro Ala Leu Asp Val Ala Ser Asp Asn His
        305                 310                 315                 320
        Phe Lys Lys Pro Lys His Lys Asp Ser Glu Lys Ile Lys Ser Asp Lys
                        325                 330                 335
        Asn Lys Gln Ser Val Asp Ser Val Asp Ser Gly Arg Gly Thr Gly Asp
                    340                 345                 350
        Pro Leu Pro Arg Ala Lys Asp Lys Val Pro Asn Asn Leu Lys Ala Gln
                    355                 360                 365
        Glu Gly Lys Val Arg Thr Asn Ser Asp Arg Lys Ser Pro Gly Ser Leu
                    370                 375                 380
        Pro Lys Val Glu Glu Met Asp Met Asp Glu Phe Glu Gln Pro Thr
        385                 390                 395                 400
        Met Ser Phe Glu Ser Tyr Leu Ser Tyr Asp Gln Pro Arg Lys Lys Lys
                        405                 410                 415
        Lys Lys Val Val Lys Thr Ser Gly Thr Ala Leu Gly Glu Lys Gly Leu
                    420                 425                 430
        Lys Lys Lys Asp Ser Lys Ser Thr Ser Lys Asn Leu Asn Ser Ala Gln
                    435                 440                 445
        Lys Leu Pro Lys Ala Asn Glu Asn Lys Ser Asp Lys Leu Gln Pro Ala
                    450                 455                 460
        Gly Ala Glu Pro Thr Arg Pro Arg Lys Val Pro Thr Asp Val Leu Pro
        465                 470                 475                 480
        Ala Leu Pro Asp Ile Pro Leu Pro Ala Ile Gln Thr Asn Tyr Arg Pro
                        485                 490                 495
        Leu Pro Ser Leu Glu Leu Ile Ser Ser Phe Gln Pro Lys Arg Lys Ala
                    500                 505                 510
        Phe Ser Ser Pro Gln Glu Glu Glu Ala Gly Phe Thr Gly Arg Arg
                515                 520                 525
        Met Asn Ser Lys Met Gln Val Tyr Ser Gly Ser Lys Cys Ala Tyr Leu
                    530                 535                 540
        Pro Lys Met Met Gln Cys Ile Arg Val Leu Lys Asn Asn Ile Asp Ser
        545                 550                 555                 560
        Ile Phe Glu Val Gly Gly Val Pro Tyr Ser Val Leu Glu Pro Val Leu
                        565                 570                 575
```

```
Glu Arg Cys Thr Pro Asp Gln Leu Tyr Arg Ile Glu Glu Cys Asn His
            580                 585                 590

Val Leu Ile Glu Glu Thr Asp Gln Leu Trp Lys Val His Cys His Arg
        595                 600                 605

Asp Phe Lys Glu Glu Arg Pro Glu Glu Tyr Glu Ser Trp Arg Glu Met
        610                 615                 620

Tyr Leu Arg Leu Gln Asp Ala Arg Glu Gln Arg Leu Arg Leu Leu Thr
625                 630                 635                 640

Asn Asn Ile Arg Ser Ala His Ala Asn Lys Pro Lys Gly Arg Gln Ala
                645                 650                 655

Lys Met Ala Phe Val Asn Ser Val Ala Lys Pro Pro Arg Asp Val Arg
                660                 665                 670

Arg Arg Gln Glu Lys Phe Gly Thr Gly Gly Ala Ala Val Pro Glu Lys
                675                 680                 685

Val Arg Ile Lys Pro Ala Pro Tyr Thr Thr Gly Ser Ser His Val Pro
        690                 695                 700

Ala Ser Asn Ser Ser Ser Ser Phe His Ser Ser Pro Glu Glu Leu Ala
705                 710                 715                 720

Tyr Glu Gly Pro Ser Thr Ser Ser Ala His Leu Ala Pro Val Ala Ser
                725                 730                 735

Ser Ser Val Ser Tyr Asp Pro Arg Lys Pro Ala Val Lys Lys Ile Ala
                740                 745                 750

Pro Met Met Ala Lys Thr Ile Lys Ala Phe Lys Asn Arg Phe Ser Arg
                755                 760                 765

Arg
```

(2) INFORMATION FOR SEQ ID NO:37:

(i) SEQUENCE CHARACTERISTICS:
        (A) LENGTH: 769 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..769
        (D) OTHER INFORMATION: /note= "amino acids 1-552 and
        557-773 of Elongin A"

(xi) SEQUENCE DESCRIPTION: SEQ ID NO:37:

```
Met Ala Ala Glu Ser Ala Leu Gln Val Val Glu Lys Leu Gln Ala Arg
1               5                   10                  15

Leu Ala Ala Asn Pro Asp Pro Lys Lys Leu Leu Lys Tyr Leu Lys Lys
                20                  25                  30

Leu Ser Val Leu Pro Ile Thr Val Asp Ile Leu Val Glu Thr Gly Val
            35                  40                  45

Gly Lys Thr Val Asn Ser Phe Arg Lys His Glu Gln Val Gly Asn Phe
        50                  55                  60

Ala Arg Asp Leu Val Ala Gln Trp Lys Lys Leu Val Pro Val Glu Arg
65                  70                  75                  80

Asn Asn Glu Ala Glu Asp Gln Asp Phe Glu Lys Ser Asn Ser Arg Lys
                85                  90                  95

Arg Pro Arg Asp Val Pro Gln Gln Glu Glu Ala Glu Gly Asn Tyr
                100                 105                 110
```

```
Gln Glu Ser Trp Gln Ala Ser Gly Ser Gln Pro Tyr Ser Pro Glu His
    115                 120                 125

Arg Gln Lys Lys His Arg Lys Leu Pro Glu Leu Glu Arg Pro His Lys
    130                 135                 140

Val Ala His Gly His Glu Arg Arg Asp Glu Arg Lys Arg Cys His Lys
145                 150                 155                 160

Val Ser Pro Pro Tyr Ser Ser Asp Pro Glu Ser Ser Asp Tyr Gly His
                165                 170                 175

Val Gln Ser Pro Pro Pro Ser Ser Pro His Gln Met Tyr Thr Asp Leu
            180                 185                 190

Ser Arg Ser Pro Glu Met Asp Gln Glu Pro Ile Val Ser His Pro Lys
        195                 200                 205

Pro Gly Lys Val His Ser Asn Thr Phe Gln Asp Arg Leu Gly Val Ser
    210                 215                 220

His Leu Gly Glu His Gln Gly Lys Gly Ala Val Ser Gln Asn Lys Pro
225                 230                 235                 240

His Lys Ser Ser His Lys Glu Lys Arg Pro Val Asp Ala Arg Gly Asp
                245                 250                 255

Glu Lys Ser Ser Val Met Gly Arg Glu Lys Ser His Lys Ala Ser Ser
            260                 265                 270

Lys Glu Glu Ser Arg Arg Leu Leu Ser Glu Asp Ser Ala Lys Glu Lys
        275                 280                 285

Leu Pro Ser Ser Val Val Lys Lys Glu Lys Asp Arg Glu Gly Asn Ser
    290                 295                 300

Leu Lys Lys Lys Leu Ser Pro Ala Leu Asp Val Ala Ser Asp Asn His
305                 310                 315                 320

Phe Lys Lys Pro Lys His Lys Asp Ser Glu Lys Ile Lys Ser Asp Lys
                325                 330                 335

Asn Lys Gln Ser Val Asp Ser Val Asp Ser Gly Arg Gly Thr Gly Asp
            340                 345                 350

Pro Leu Pro Arg Ala Lys Asp Lys Val Pro Asn Asn Leu Lys Ala Gln
    355                 360                 365

Glu Gly Lys Val Arg Thr Asn Ser Asp Arg Lys Ser Pro Gly Ser Leu
    370                 375                 380

Pro Lys Val Glu Glu Met Asp Met Asp Asp Glu Phe Glu Gln Pro Thr
385                 390                 395                 400

Met Ser Phe Glu Ser Tyr Leu Ser Tyr Asp Gln Pro Arg Lys Lys Lys
                405                 410                 415

Lys Lys Val Val Lys Thr Ser Gly Thr Ala Leu Gly Glu Lys Gly Leu
            420                 425                 430

Lys Lys Lys Asp Ser Lys Ser Thr Ser Lys Asn Leu Asn Ser Ala Gln
        435                 440                 445

Lys Leu Pro Lys Ala Asn Glu Asn Lys Ser Asp Lys Leu Gln Pro Ala
    450                 455                 460

Gly Ala Glu Pro Thr Arg Pro Arg Lys Val Pro Thr Asp Val Leu Pro
465                 470                 475                 480

Ala Leu Pro Asp Ile Pro Leu Pro Ala Ile Gln Thr Asn Tyr Arg Pro
                485                 490                 495

Leu Pro Ser Leu Glu Leu Ile Ser Ser Phe Gln Pro Lys Arg Lys Ala
            500                 505                 510

Phe Ser Ser Pro Gln Glu Glu Glu Ala Gly Phe Thr Gly Arg Arg
        515                 520                 525

Met Asn Ser Lys Met Gln Val Tyr Ser Gly Ser Lys Cys Ala Tyr Leu
```

-continued

```
                530                 535                 540
    Pro Lys Met Met Thr Leu His Gln Val Leu Lys Asn Asn Ile Asp Ser
    545                 550                 555                 560

Ile Phe Glu Val Gly Gly Val Pro Tyr Ser Val Leu Glu Pro Val Leu
                    565                 570                 575

Glu Arg Cys Thr Pro Asp Gln Leu Tyr Arg Ile Glu Glu Cys Asn His
                580                 585                 590

Val Leu Ile Glu Glu Thr Asp Gln Leu Trp Lys Val His Cys His Arg
                595                 600                 605

Asp Phe Lys Glu Glu Arg Pro Glu Glu Tyr Glu Ser Trp Arg Glu Met
                610                 615                 620

Tyr Leu Arg Leu Gln Asp Ala Arg Glu Gln Arg Leu Arg Leu Leu Thr
    625                 630                 635                 640

Asn Asn Ile Arg Ser Ala His Ala Asn Lys Pro Lys Gly Arg Gln Ala
                    645                 650                 655

Lys Met Ala Phe Val Asn Ser Val Ala Lys Pro Pro Arg Asp Val Arg
                660                 665                 670

Arg Arg Gln Glu Lys Phe Gly Thr Gly Gly Ala Ala Val Pro Glu Lys
                675                 680                 685

Val Arg Ile Lys Pro Ala Pro Tyr Thr Thr Gly Ser Ser His Val Pro
    690                 695                 700

Ala Ser Asn Ser Ser Ser Phe His Ser Ser Pro Glu Glu Leu Ala
    705                 710                 715                 720

Tyr Glu Gly Pro Ser Thr Ser Ser Ala His Leu Ala Pro Val Ala Ser
                    725                 730                 735

Ser Ser Val Ser Tyr Asp Pro Arg Lys Pro Ala Val Lys Lys Ile Ala
                740                 745                 750

Pro Met Met Ala Lys Thr Ile Lys Ala Phe Lys Asn Arg Phe Ser Arg
                755                 760                 765

Arg
```

(2) INFORMATION FOR SEQ ID NO:38:

(i) SEQUENCE CHARACTERISTICS:
        (A) LENGTH: 769 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..769
        (D) OTHER INFORMATION: /note= "amino acid 1-556 and
           561-773 of Elongin A"

(xi) SEQUENCE DESCRIPTION: SEQ ID NO:38:

```
Met Ala Ala Glu Ser Ala Leu Gln Val Val Glu Lys Leu Gln Ala Arg
1               5                   10                  15

Leu Ala Ala Asn Pro Asp Pro Lys Leu Leu Lys Tyr Leu Lys Lys
            20                  25                  30

Leu Ser Val Leu Pro Ile Thr Val Asp Ile Leu Val Glu Thr Gly Val
            35                  40                  45

Gly Lys Thr Val Asn Ser Phe Arg Lys His Glu Gln Val Gly Asn Phe
            50                  55                  60

Ala Arg Asp Leu Val Ala Gln Trp Lys Lys Leu Val Pro Val Glu Arg
65              70                  75                  80
```

-continued

```
Asn Asn Glu Ala Glu Asp Gln Asp Phe Glu Lys Ser Asn Ser Arg Lys
                85                  90                  95
Arg Pro Arg Asp Val Pro Gln Gln Glu Glu Ala Glu Gly Asn Tyr
        100                 105                 110
Gln Glu Ser Trp Gln Ala Ser Gly Ser Gln Pro Tyr Ser Pro Glu His
            115                 120                 125
Arg Gln Lys Lys His Arg Lys Leu Pro Glu Leu Glu Arg Pro His Lys
        130                 135                 140
Val Ala His Gly His Glu Arg Arg Asp Glu Arg Lys Arg Cys His Lys
145                 150                 155                 160
Val Ser Pro Pro Tyr Ser Ser Asp Pro Glu Ser Ser Asp Tyr Gly His
                165                 170                 175
Val Gln Ser Pro Pro Ser Ser Pro His Gln Met Tyr Thr Asp Leu
            180                 185                 190
Ser Arg Ser Pro Glu Met Asp Gln Glu Pro Ile Val Ser His Pro Lys
        195                 200                 205
Pro Gly Lys Val His Ser Asn Thr Phe Gln Asp Arg Leu Gly Val Ser
        210                 215                 220
His Leu Gly Glu His Gln Gly Lys Gly Ala Val Ser Gln Asn Lys Pro
225                 230                 235                 240
His Lys Ser Ser His Lys Glu Lys Arg Pro Val Asp Ala Arg Gly Asp
                245                 250                 255
Glu Lys Ser Ser Val Met Gly Arg Glu Lys Ser His Lys Ala Ser Ser
                260                 265                 270
Lys Glu Glu Ser Arg Arg Leu Leu Ser Glu Asp Ser Ala Lys Glu Lys
        275                 280                 285
Leu Pro Ser Ser Val Val Lys Lys Glu Lys Asp Arg Glu Gly Asn Ser
        290                 295                 300
Leu Lys Lys Lys Leu Ser Pro Ala Leu Asp Val Ala Ser Asp Asn His
305                 310                 315                 320
Phe Lys Lys Pro Lys His Lys Asp Ser Glu Lys Ile Lys Ser Asp Lys
                325                 330                 335
Asn Lys Gln Ser Val Asp Ser Val Asp Ser Gly Arg Gly Thr Gly Asp
            340                 345                 350
Pro Leu Pro Arg Ala Lys Asp Lys Val Pro Asn Asn Leu Lys Ala Gln
        355                 360                 365
Glu Gly Lys Val Arg Thr Asn Ser Asp Arg Lys Ser Pro Gly Ser Leu
        370                 375                 380
Pro Lys Val Glu Glu Met Asp Met Asp Glu Phe Glu Gln Pro Thr
385                 390                 395                 400
Met Ser Phe Glu Ser Tyr Leu Ser Tyr Asp Gln Pro Arg Lys Lys Lys
                405                 410                 415
Lys Lys Val Val Lys Thr Ser Gly Thr Ala Leu Gly Glu Lys Gly Leu
            420                 425                 430
Lys Lys Lys Asp Ser Lys Ser Thr Ser Lys Asn Leu Asn Ser Ala Gln
        435                 440                 445
Lys Leu Pro Lys Ala Asn Glu Asn Lys Ser Asp Lys Leu Gln Pro Ala
    450                 455                 460
Gly Ala Glu Pro Thr Arg Pro Arg Lys Val Pro Thr Asp Val Leu Pro
465                 470                 475                 480
Ala Leu Pro Asp Ile Pro Leu Pro Ala Ile Gln Thr Asn Tyr Arg Pro
                485                 490                 495
```

```
Leu Pro Ser Leu Glu Leu Ile Ser Ser Phe Gln Pro Lys Arg Lys Ala
            500                 505                 510

Phe Ser Ser Pro Gln Glu Glu Glu Ala Gly Phe Thr Gly Arg Arg
            515                 520                 525

Met Asn Ser Lys Met Gln Val Tyr Ser Gly Ser Lys Cys Ala Tyr Leu
            530                 535                 540

Pro Lys Met Met Thr Leu His Gln Gln Cys Ile Arg Asn Ile Asp Ser
545                 550                 555                 560

Ile Phe Glu Val Gly Gly Val Pro Tyr Ser Val Leu Glu Pro Val Leu
                565                 570                 575

Glu Arg Cys Thr Pro Asp Gln Leu Tyr Arg Ile Glu Glu Cys Asn His
            580                 585                 590

Val Leu Ile Glu Glu Thr Asp Gln Leu Trp Lys Val His Cys His Arg
            595                 600                 605

Asp Phe Lys Glu Glu Arg Pro Glu Glu Tyr Glu Ser Trp Arg Glu Met
            610                 615                 620

Tyr Leu Arg Leu Gln Asp Ala Arg Glu Gln Arg Leu Arg Leu Leu Thr
625                 630                 635                 640

Asn Asn Ile Arg Ser Ala His Ala Asn Lys Pro Lys Gly Arg Gln Ala
                645                 650                 655

Lys Met Ala Phe Val Asn Ser Val Ala Lys Pro Arg Asp Val Arg
            660                 665                 670

Arg Arg Gln Glu Lys Phe Gly Thr Gly Gly Ala Ala Val Pro Glu Lys
            675                 680                 685

Val Arg Ile Lys Pro Ala Pro Tyr Thr Thr Gly Ser Ser His Val Pro
            690                 695                 700

Ala Ser Asn Ser Ser Ser Ser Phe His Ser Ser Pro Glu Glu Leu Ala
705                 710                 715                 720

Tyr Glu Gly Pro Ser Thr Ser Ser Ala His Leu Ala Pro Val Ala Ser
                725                 730                 735

Ser Ser Val Ser Tyr Asp Pro Arg Lys Pro Ala Val Lys Lys Ile Ala
            740                 745                 750

Pro Met Met Ala Lys Thr Ile Lys Ala Phe Lys Asn Arg Phe Ser Arg
            755                 760                 765

Arg (2) INFORMATION FOR SEQ ID NO:39:

(i) SEQUENCE CHARACTERISTICS:
        (A) LENGTH: 769 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..769
        (D) OTHER INFORMATION: /note= "amino acids 1-560 and
            565-773 of Elongin A"

(xi) SEQUENCE DESCRIPTION: SEQ ID NO:39:

Met Ala Ala Glu Ser Ala Leu Gln Val Val Glu Lys Leu Gln Ala Arg
1               5                   10                  15

Leu Ala Ala Asn Pro Asp Pro Lys Lys Leu Leu Lys Tyr Leu Lys Lys
                20                  25                  30

Leu Ser Val Leu Pro Ile Thr Val Asp Ile Leu Val Glu Thr Gly Val
```

-continued

```
                35                  40                  45
    Gly Lys Thr Val Asn Ser Phe Arg Lys His Glu Gln Val Gly Asn Phe
                 50                  55                  60
    Ala Arg Asp Leu Val Ala Gln Trp Lys Lys Leu Val Pro Val Glu Arg
     65                  70                  75                  80
    Asn Asn Glu Ala Glu Asp Gln Asp Phe Glu Lys Ser Asn Ser Arg Lys
                     85                  90                  95
    Arg Pro Arg Asp Val Pro Gln Gln Glu Glu Ala Glu Gly Asn Tyr
                    100                 105                 110
    Gln Glu Ser Trp Gln Ala Ser Gly Ser Gln Pro Tyr Ser Pro Glu His
                    115                 120                 125
    Arg Gln Lys Lys His Arg Lys Leu Pro Glu Leu Glu Arg Pro His Lys
                    130                 135                 140
    Val Ala His Gly His Glu Arg Arg Asp Glu Arg Lys Arg Cys His Lys
    145                 150                 155                 160
    Val Ser Pro Pro Tyr Ser Ser Asp Pro Glu Ser Ser Asp Tyr Gly His
                    165                 170                 175
    Val Gln Ser Pro Pro Ser Ser Pro His Gln Met Tyr Thr Asp Leu
                    180                 185                 190
    Ser Arg Ser Pro Glu Met Asp Gln Glu Pro Ile Val Ser His Pro Lys
                    195                 200                 205
    Pro Gly Lys Val His Ser Asn Thr Phe Gln Asp Arg Leu Gly Val Ser
                    210                 215                 220
    His Leu Gly Glu His Gln Gly Lys Gly Ala Val Ser Gln Asn Lys Pro
    225                 230                 235                 240
    His Lys Ser Ser His Lys Glu Lys Arg Pro Val Asp Ala Arg Gly Asp
                    245                 250                 255
    Glu Lys Ser Ser Val Met Gly Arg Glu Lys Ser His Lys Ala Ser Ser
                    260                 265                 270
    Lys Glu Glu Ser Arg Arg Leu Leu Ser Glu Asp Ser Ala Lys Glu Lys
                    275                 280                 285
    Leu Pro Ser Ser Val Val Lys Lys Glu Lys Asp Arg Glu Gly Asn Ser
                    290                 295                 300
    Leu Lys Lys Lys Leu Ser Pro Ala Leu Asp Val Ala Ser Asp Asn His
    305                 310                 315                 320
    Phe Lys Lys Pro Lys His Lys Asp Ser Glu Lys Ile Lys Ser Asp Lys
                    325                 330                 335
    Asn Lys Gln Ser Val Asp Ser Val Asp Ser Gly Arg Gly Thr Gly Asp
                    340                 345                 350
    Pro Leu Pro Arg Ala Lys Asp Lys Val Pro Asn Asn Leu Lys Ala Gln
                    355                 360                 365
    Glu Gly Lys Val Arg Thr Asn Ser Asp Arg Lys Ser Pro Gly Ser Leu
                    370                 375                 380
    Pro Lys Val Glu Glu Met Asp Met Asp Glu Phe Glu Gln Pro Thr
    385                 390                 395                 400
    Met Ser Phe Glu Ser Tyr Leu Ser Tyr Asp Gln Pro Arg Lys Lys Lys
                    405                 410                 415
    Lys Lys Val Val Lys Thr Ser Gly Thr Ala Leu Gly Glu Lys Gly Leu
                    420                 425                 430
    Lys Lys Lys Asp Ser Lys Ser Thr Ser Lys Asn Leu Asn Ser Ala Gln
                    435                 440                 445
    Lys Leu Pro Lys Ala Asn Glu Asn Lys Ser Asp Lys Leu Gln Pro Ala
    450                 455                 460
```

-continued

```
Gly Ala Glu Pro Thr Arg Pro Arg Lys Val Pro Thr Asp Val Leu Pro
465                 470                 475                 480

Ala Leu Pro Asp Ile Pro Leu Pro Ala Ile Gln Thr Asn Tyr Arg Pro
            485                 490                 495

Leu Pro Ser Leu Glu Leu Ile Ser Ser Phe Gln Pro Lys Arg Lys Ala
        500                 505                 510

Phe Ser Ser Pro Gln Glu Glu Glu Ala Gly Phe Thr Gly Arg Arg
        515                 520                 525

Met Asn Ser Lys Met Gln Val Tyr Ser Gly Ser Lys Cys Ala Tyr Leu
530                 535                 540

Pro Lys Met Met Thr Leu His Gln Gln Cys Ile Arg Val Leu Lys Asn
545                 550                 555                 560

Ile Phe Glu Val Gly Gly Val Pro Tyr Ser Val Leu Glu Pro Val Leu
                565                 570                 575

Glu Arg Cys Thr Pro Asp Gln Leu Tyr Arg Ile Glu Glu Cys Asn His
            580                 585                 590

Val Leu Ile Glu Glu Thr Asp Gln Leu Trp Lys Val His Cys His Arg
        595                 600                 605

Asp Phe Lys Glu Glu Arg Pro Glu Glu Tyr Glu Ser Trp Arg Glu Met
610                 615                 620

Tyr Leu Arg Leu Gln Asp Ala Arg Glu Gln Arg Leu Arg Leu Leu Thr
625                 630                 635                 640

Asn Asn Ile Arg Ser Ala His Ala Asn Lys Pro Lys Gly Arg Gln Ala
                645                 650                 655

Lys Met Ala Phe Val Asn Ser Val Ala Lys Pro Pro Arg Asp Val Arg
            660                 665                 670

Arg Arg Gln Glu Lys Phe Gly Thr Gly Gly Ala Ala Val Pro Glu Lys
        675                 680                 685

Val Arg Ile Lys Pro Ala Pro Tyr Thr Thr Gly Ser Ser His Val Pro
690                 695                 700

Ala Ser Asn Ser Ser Ser Ser Phe His Ser Ser Pro Glu Glu Leu Ala
705                 710                 715                 720

Tyr Glu Gly Pro Ser Thr Ser Ser Ala His Leu Ala Pro Val Ala Ser
                725                 730                 735

Ser Ser Val Ser Tyr Asp Pro Arg Lys Pro Ala Val Lys Lys Ile Ala
            740                 745                 750

Pro Met Met Ala Lys Thr Ile Lys Ala Phe Lys Asn Arg Phe Ser Arg
        755                 760                 765

Arg
```

(2) INFORMATION FOR SEQ ID NO:40:

(i) SEQUENCE CHARACTERISTICS:
        (A) LENGTH: 769 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Protein
        (B) LOCATION: 1..769
        (D) OTHER INFORMATION: /note= "amino acids 1-564 and
           569-773 of Elongin A"

(xi) SEQUENCE DESCRIPTION: SEQ ID NO:40:

```
Met Ala Ala Glu Ser Ala Leu Gln Val Val Glu Lys Leu Gln Ala Arg
1               5                   10                  15

Leu Ala Ala Asn Pro Asp Pro Lys Lys Leu Lys Tyr Leu Lys Lys
            20              25              30

Leu Ser Val Leu Pro Ile Thr Val Asp Ile Leu Val Glu Thr Gly Val
        35              40                  45

Gly Lys Thr Val Asn Ser Phe Arg Lys His Glu Gln Val Gly Asn Phe
    50                  55                  60

Ala Arg Asp Leu Val Ala Gln Trp Lys Lys Leu Val Pro Val Glu Arg
65              70              75                          80

Asn Asn Glu Ala Glu Asp Gln Asp Phe Glu Lys Ser Asn Ser Arg Lys
            85              90                  95

Arg Pro Arg Asp Val Pro Gln Gln Glu Glu Ala Glu Gly Asn Tyr
            100             105             110

Gln Glu Ser Trp Gln Ala Ser Gly Ser Gln Pro Tyr Ser Pro Glu His
        115             120             125

Arg Gln Lys Lys His Arg Lys Leu Pro Glu Leu Glu Arg Pro His Lys
        130             135             140

Val Ala His Gly His Glu Arg Arg Asp Glu Arg Lys Arg Cys His Lys
145             150             155             160

Val Ser Pro Pro Tyr Ser Ser Asp Pro Glu Ser Ser Asp Tyr Gly His
                165             170             175

Val Gln Ser Pro Pro Ser Ser Pro His Gln Met Tyr Thr Asp Leu
        180             185             190

Ser Arg Ser Pro Glu Met Asp Gln Glu Pro Ile Val Ser His Pro Lys
        195             200             205

Pro Gly Lys Val His Ser Asn Thr Phe Gln Asp Arg Leu Gly Val Ser
    210             215             220

His Leu Gly Glu His Gln Gly Lys Gly Ala Val Ser Gln Asn Lys Pro
225             230             235             240

His Lys Ser Ser His Lys Glu Lys Arg Pro Val Asp Ala Arg Gly Asp
            245             250             255

Glu Lys Ser Ser Val Met Gly Arg Glu Lys Ser His Lys Ala Ser Ser
        260             265             270

Lys Glu Glu Ser Arg Arg Leu Leu Ser Glu Asp Ser Ala Lys Glu Lys
    275             280             285

Leu Pro Ser Ser Val Val Lys Lys Glu Lys Asp Arg Glu Gly Asn Ser
    290             295             300

Leu Lys Lys Lys Leu Ser Pro Ala Leu Asp Val Ala Ser Asp Asn His
305             310             315             320

Phe Lys Lys Pro Lys His Lys Asp Ser Glu Lys Ile Lys Ser Asp Lys
            325             330             335

Asn Lys Gln Ser Val Asp Ser Val Asp Ser Gly Arg Gly Thr Gly Asp
        340             345             350

Pro Leu Pro Arg Ala Lys Asp Lys Val Pro Asn Asn Leu Lys Ala Gln
        355             360             365

Glu Gly Lys Val Arg Thr Asn Ser Asp Arg Lys Ser Pro Gly Ser Leu
    370             375             380

Pro Lys Val Glu Glu Met Asp Met Asp Asp Phe Glu Gln Pro Thr
385             390             395             400

Met Ser Phe Glu Ser Tyr Leu Ser Tyr Asp Gln Pro Arg Lys Lys Lys
            405             410             415

Lys Lys Val Val Lys Thr Ser Gly Thr Ala Leu Gly Glu Lys Gly Leu
```

```
               420           425           430
    Lys Lys Lys Asp Ser Lys Ser Thr Ser Lys Asn Leu Asn Ser Ala Gln
            435           440           445

Lys Leu Pro Lys Ala Asn Glu Asn Lys Ser Asp Lys Leu Gln Pro Ala
            450           455           460

Gly Ala Glu Pro Thr Arg Pro Arg Lys Val Pro Thr Asp Val Leu Pro
    465           470           475           480

Ala Leu Pro Asp Ile Pro Leu Pro Ala Ile Gln Thr Asn Tyr Arg Pro
                485           490           495

Leu Pro Ser Leu Glu Leu Ile Ser Ser Phe Gln Pro Lys Arg Lys Ala
            500           505           510

Phe Ser Ser Pro Gln Glu Glu Glu Ala Gly Phe Thr Gly Arg Arg
            515           520           525

Met Asn Ser Lys Met Gln Val Tyr Ser Gly Ser Lys Cys Ala Tyr Leu
            530           535           540

Pro Lys Met Met Thr Leu His Gln Gln Cys Ile Arg Val Leu Lys Asn
    545           550           555           560

Asn Ile Asp Ser Gly Gly Val Pro Tyr Ser Val Leu Glu Pro Val Leu
                565           570           575

Glu Arg Cys Thr Pro Asp Gln Leu Tyr Arg Ile Glu Glu Cys Asn His
            580           585           590

Val Leu Ile Glu Glu Thr Asp Gln Leu Trp Lys Val His Cys His Arg
            595           600           605

Asp Phe Lys Glu Glu Arg Pro Glu Glu Tyr Glu Ser Trp Arg Glu Met
            610           615           620

Tyr Leu Arg Leu Gln Asp Ala Arg Glu Gln Arg Leu Arg Leu Leu Thr
    625           630           635           640

Asn Asn Ile Arg Ser Ala His Ala Asn Lys Pro Lys Gly Arg Gln Ala
                645           650           655

Lys Met Ala Phe Val Asn Ser Val Ala Lys Pro Pro Arg Asp Val Arg
                660           665           670

Arg Arg Gln Glu Lys Phe Gly Thr Gly Gly Ala Ala Val Pro Glu Lys
            675           680           685

Val Arg Ile Lys Pro Ala Pro Tyr Thr Thr Gly Ser Ser His Val Pro
            690           695           700

Ala Ser Asn Ser Ser Ser Ser Phe His Ser Ser Pro Glu Glu Leu Ala
    705           710           715           720

Tyr Glu Gly Pro Ser Thr Ser Ser Ala His Leu Ala Pro Val Ala Ser
                725           730           735

Ser Ser Val Ser Tyr Asp Pro Arg Lys Pro Ala Val Lys Lys Ile Ala
                740           745           750

Pro Met Met Ala Lys Thr Ile Lys Ala Phe Lys Asn Arg Phe Ser Arg
                755           760           765

Arg (2) INFORMATION FOR SEQ ID NO:41:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (ix) FEATURE:
```

(A) NAME/KEY: Peptide
            (B) LOCATION: 1..6
            (D) OTHER INFORMATION: /note= "amino acids 556-561 of
                Elongin A"

(xi) SEQUENCE DESCRIPTION: SEQ ID NO:41:

Arg Val Leu Lys Asn Asn
1               5

(2) INFORMATION FOR SEQ ID NO:42:

(i) SEQUENCE CHARACTERISTICS:
        (A) LENGTH: 434 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Protein
        (B) LOCATION: 1..434
        (D) OTHER INFORMATION: /note= "entire amino acid sequence
            of C. elegans"

(xi) SEQUENCE DESCRIPTION: SEQ ID NO:42:

Met Pro Glu Thr Asp Glu Glu Lys Val Arg Arg Tyr Thr Glu Cys Leu
1               5                   10                  15

Met Asn Gly Ile Asp Pro Lys Arg Ala Leu Lys Arg Leu Tyr Asp Leu
            20                  25                  30

Asn Val Ser Pro Glu Val Phe Lys Ser Ala Asp Thr Val Gln Cys Val
        35                  40                  45

Lys Arg Tyr Glu Ser Ser Pro Glu Leu Ala Lys Tyr Ala Lys Arg Val
50                  55                  60

Arg Asp Lys Leu Leu Gly Gly Arg Lys Arg Glu Lys Gly Gly Gly Glu
65                  70                  75                  80

Asp Asp Ala Asp Ile Glu His Thr Ala Leu Lys Lys Ala Lys Lys Glu
                85                  90                  95

Glu Val Asn Leu Asp Glu Glu Phe Ala Glu Ala Met Lys Ser Gly Val
            100                 105                 110

Ser Ala Gln Ala Ser Ser Ala Pro Arg Ala Thr Val Asp Tyr Ser Lys
        115                 120                 125

Tyr Lys Val Val Lys Arg Val Glu Val Lys Val Glu Pro Lys Pro Glu
130                 135                 140

Pro Val Asp Val His Glu Gln Gln Ala Ser Ser Ser Met Ser Tyr
145                 150                 155                 160

Gln Arg Glu His Gln Lys Asp Tyr Ala Pro Val Val Pro Thr Cys Lys
                165                 170                 175

Pro Ser Gly Gln Pro Lys Lys Ala Ile Pro Gln Ser Lys Ser Leu His
            180                 185                 190

Ala Asp Glu Asn Met Phe Lys Pro Arg Lys Glu Arg Gln Lys Val Phe
        195                 200                 205

Ala Gly Arg Arg Lys Arg Val Gly Glu Gly Val Ser Thr Leu Val Ser
210                 215                 220

Leu Cys Gln Thr Val Leu Met Ser His Ile Asp Met Ile Asp His Val
225                 230                 235                 240

Gly Ile Val Pro Phe Asp Leu Leu Lys Pro Val Leu Asp His Ala Ser
                245                 250                 255

Thr Asp Gln Leu Arg His Ile Leu Asp Val Asn Pro Met Leu Val Glu
            260                 265                 270

Asp Ala Asp Glu Met Phe His Glu Met Val Ser Arg Glu Phe Pro Lys
            275                 280                 285

Tyr Ala Asn Arg Glu Lys Ser Gly Trp Thr Trp Arg Glu Met Tyr Asp
        290                 295                 300

Arg Leu Val Glu Lys Lys Gln Lys Lys Glu Asn Asp Lys Leu Glu Met
305                 310                 315                 320

Leu Thr Ser Arg Ile Gly Lys Ser Asn Ser Ala Gln Ser Gln Gly Arg
                325                 330                 335

Gln Thr Met Val Ile Asp Met Ala His Thr Arg Val Arg Ser Lys Ser
            340                 345                 350

Phe Phe Asn Thr Val Lys Asp Ser Gln Val Lys Met Ser Ala Thr Pro
        355                 360                 365

Ser Ala Leu Gln Leu Ser Gln Ala Arg Lys Asn Val Lys Ile Glu Gly
    370                 375                 380

Lys Ala Gln Leu Arg Thr Ile Thr Pro Arg Gly Gly Gly Val Pro Ser
385                 390                 395                 400

Thr Ser Arg Ser Arg Ser Asn Asn Asn Asn Met Asn Asn Gly Leu
                405                 410                 415

Val Val Lys Lys Thr Ala Pro Leu Met Ala Lys Cys Lys Lys Met Leu
            420                 425                 430

Lys Arg (2) INFORMATION FOR SEQ ID NO:43:

(i) SEQUENCE CHARACTERISTICS:
        (A) LENGTH: 143 amino acids
        (B) TYPE: amino acid
        (C) STRANDEDNESS: Not Relevant
        (D) TOPOLOGY: Not Relevant (ii) MOLECULE TYPE: protein (ix) FEATURE:
        (A) NAME/KEY: Peptide
        (B) LOCATION: 1..143
        (D) OTHER INFORMATION: /note= "amino acids 520-662 of
            Elongin A"

(xi) SEQUENCE DESCRIPTION: SEQ ID NO:43:

Glu Glu Ala Gly Phe Thr Gly Arg Arg Met Asn Ser Lys Met Gln Val
1               5                   10                  15

Tyr Ser Gly Ser Lys Cys Ala Tyr Leu Pro Lys Met Met Thr Leu His
            20                  25                  30

Gln Gln Cys Ile Arg Val Leu Lys Asn Asn Ile Asp Ser Ile Phe Glu
        35                  40                  45

Val Gly Gly Val Pro Tyr Ser Val Leu Glu Pro Val Leu Glu Arg Cys
    50                  55                  60

Thr Pro Asp Gln Leu Tyr Arg Ile Glu Glu Cys Asn His Val Leu Ile
65                  70                  75                  80

Glu Glu Thr Asp Gln Leu Trp Lys Val His Cys His Arg Asp Phe Lys
                85                  90                  95

Glu Glu Arg Pro Glu Glu Tyr Glu Ser Trp Arg Glu Met Tyr Leu Arg
            100                 105                 110

Leu Gln Asp Ala Arg Glu Gln Arg Leu Arg Leu Leu Thr Asn Asn Ile
        115                 120                 125

Arg Ser Ala His Ala Asn Lys Pro Lys Gly Arg Gln Ala Lys Met
    130                 135                 140

(2) INFORMATION FOR SEQ ID NO:44:

(i) SEQUENCE CHARACTERISTICS:
        (A) LENGTH: 341 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..341
        (D) OTHER INFORMATION: /note= "amino acids 94-434 of C.
            elegans"

(xi) SEQUENCE DESCRIPTION: SEQ ID NO:44:

```
Lys Lys Glu Glu Val Asn Leu Asp Glu Glu Phe Ala Glu Ala Met Lys
  1               5                  10                  15

Ser Gly Val Ser Ala Gln Ala Ser Ala Pro Arg Ala Thr Val Asp
             20                  25                  30

Tyr Ser Lys Tyr Lys Val Val Lys Arg Val Glu Val Lys Val Glu Pro
             35                  40                  45

Lys Pro Glu Pro Val Asp Val His Glu Gln Gln Ala Ser Ser Ser Ser
 50                  55                  60

Met Ser Tyr Gln Arg Glu His Gln Lys Asp Tyr Ala Pro Val Val Pro
 65                  70                  75                  80

Thr Cys Lys Pro Ser Gly Gln Pro Lys Lys Ala Ile Pro Gln Ser Lys
                 85                  90                  95

Ser Leu His Ala Asp Glu Asn Met Phe Lys Pro Arg Lys Glu Arg Gln
                100                 105                 110

Lys Val Phe Ala Gly Arg Arg Lys Arg Val Gly Glu Gly Val Ser Thr
            115                 120                 125

Leu Val Ser Leu Cys Gln Thr Val Leu Met Ser His Ile Asp Met Ile
130                 135                 140

Asp His Val Gly Ile Val Pro Phe Asp Leu Leu Lys Pro Val Leu Asp
145                 150                 155                 160

His Ala Ser Thr Asp Gln Leu Arg His Ile Leu Asp Val Asn Pro Met
                165                 170                 175

Leu Val Glu Asp Ala Asp Glu Met Phe His Glu Met Val Ser Arg Glu
            180                 185                 190

Phe Pro Lys Tyr Ala Asn Arg Glu Lys Ser Gly Trp Thr Trp Arg Glu
            195                 200                 205

Met Tyr Asp Arg Leu Val Glu Lys Lys Gln Lys Lys Glu Asn Asp Lys
210                 215                 220

Leu Glu Met Leu Thr Ser Arg Ile Gly Lys Ser Asn Ser Ala Gln Ser
225                 230                 235                 240

Gln Gly Arg Gln Thr Met Val Ile Asp Met Ala His Thr Arg Val Arg
                245                 250                 255

Ser Lys Ser Phe Phe Asn Thr Val Lys Asp Ser Gln Val Lys Met Ser
            260                 265                 270

Ala Thr Pro Ser Ala Leu Gln Leu Ser Gln Ala Arg Lys Asn Val Lys
            275                 280                 285

Ile Glu Gly Lys Ala Gln Leu Arg Thr Ile Thr Pro Arg Gly Gly Gly
290                 295                 300

Val Pro Ser Thr Ser Arg Ser Arg Ser Asn Asn Asn Asn Met Asn
305                 310                 315                 320
```

```
        Asn Gly Leu Val Val Lys Lys Thr Ala Pro Leu Met Ala Lys Cys Lys
                        325                 330                 335

Lys Met Leu Lys Arg
                        340

(2) INFORMATION FOR SEQ ID NO:45:

(i) SEQUENCE CHARACTERISTICS:
        (A) LENGTH: 233 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..233
        (D) OTHER INFORMATION: /note= "amino acids 202-434 of C.
            elegans"

(xi) SEQUENCE DESCRIPTION: SEQ ID NO:45:

Lys Glu Arg Gln Lys Val Phe Ala Gly Arg Arg Lys Arg Val Gly Glu
        1               5                   10                  15

Gly Val Ser Thr Leu Val Ser Leu Cys Gln Thr Val Leu Met Ser His
                        20                  25                  30

Ile Asp Met Ile Asp His Val Gly Ile Val Pro Phe Asp Leu Leu Lys
                        35                  40                  45

Pro Val Leu Asp His Ala Ser Thr Asp Gln Leu Arg His Ile Leu Asp
            50                  55                  60

Val Asn Pro Met Leu Val Glu Asp Ala Asp Glu Met Phe His Glu Met
        65                  70                  75                  80

Val Ser Arg Glu Phe Pro Lys Tyr Ala Asn Arg Glu Lys Ser Gly Trp
                        85                  90                  95

Thr Trp Arg Glu Met Tyr Asp Arg Leu Val Glu Lys Lys Gln Lys Lys
                        100                 105                 110

Glu Asn Asp Lys Leu Glu Met Leu Thr Ser Arg Ile Gly Lys Ser Asn
                        115                 120                 125

Ser Ala Gln Ser Gln Gly Arg Gln Thr Met Val Ile Asp Met Ala His
            130                 135                 140

Thr Arg Val Arg Ser Lys Ser Phe Phe Asn Thr Val Lys Asp Ser Gln
        145                 150                 155                 160

Val Lys Met Ser Ala Thr Pro Ser Ala Leu Gln Leu Ser Gln Ala Arg
                        165                 170                 175

Lys Asn Val Lys Ile Glu Gly Lys Ala Gln Leu Arg Thr Ile Thr Pro
                        180                 185                 190

Arg Gly Gly Val Pro Ser Thr Ser Arg Ser Arg Ser Asn Asn Asn
                        195                 200                 205

Asn Asn Met Asn Asn Gly Leu Val Val Lys Lys Thr Ala Pro Leu Met
            210                 215                 220

Ala Lys Cys Lys Lys Met Leu Lys Arg
        225                 230

(2) INFORMATION FOR SEQ ID NO:46:

(i) SEQUENCE CHARACTERISTICS:
        (A) LENGTH: 98 amino acids
        (B) TYPE: amino acid
        (C) STRANDEDNESS: Not Relevant
        (D) TOPOLOGY: Not Relevant
```

(ii) MOLECULE TYPE: peptide (ix) FEATURE:
    (A) NAME/KEY: Peptide
    (B) LOCATION: 1..98
    (D) OTHER INFORMATION: /note= "amino acids 15-112 of
        Elongin C"

(xi) SEQUENCE DESCRIPTION: SEQ ID NO:46:

```
Asp Ala Met Tyr Val Lys Leu Ile Ser Ser Asp Gly His Glu Phe Ile
1               5                   10                  15

Val Lys Arg Glu His Ala Leu Thr Ser Gly Thr Ile Lys Ala Met Leu
            20                  25                  30

Ser Gly Pro Gly Gln Phe Ala Glu Asn Glu Thr Asn Glu Val Asn Phe
            35                  40                  45

Arg Glu Ile Pro Ser His Val Leu Ser Lys Val Cys Met Tyr Phe Thr
            50                  55                  60

Tyr Lys Val Arg Tyr Thr Asn Ser Ser Thr Glu Ile Pro Glu Phe Pro
65                  70                  75                  80

Ile Ala Pro Glu Ile Ala Leu Glu Leu Leu Met Ala Ala Asn Phe Leu
            85                  90                  95

Asp Cys
```

(2) INFORMATION FOR SEQ ID NO:47:

(i) SEQUENCE CHARACTERISTICS:
    (A) LENGTH: 94 amino acids
    (B) TYPE: amino acid
    (C) STRANDEDNESS: Not Relevant
    (D) TOPOLOGY: Not Relevant (ii) MOLECULE TYPE: peptide (ix) FEATURE:
    (A) NAME/KEY: Peptide
    (B) LOCATION: 1..94
    (D) OTHER INFORMATION: /note= "amino acids 19-112 of
        Elongin C"

(xi) SEQUENCE DESCRIPTION: SEQ ID NO:47:

```
Val Lys Leu Ile Ser Ser Asp Gly His Glu Phe Ile Val Lys Arg Glu
1               5                   10                  15

His Ala Leu Thr Ser Gly Thr Ile Lys Ala Met Leu Ser Gly Pro Gly
            20                  25                  30

Gln Phe Ala Glu Asn Glu Thr Asn Glu Val Asn Phe Arg Glu Ile Pro
            35                  40                  45

Ser His Val Leu Ser Lys Val Cys Met Tyr Phe Thr Tyr Lys Val Arg
            50                  55                  60

Tyr Thr Asn Ser Ser Thr Glu Ile Pro Glu Phe Pro Ile Ala Pro Glu
65                  70                  75                  80

Ile Ala Leu Glu Leu Leu Met Ala Ala Asn Phe Leu Asp Cys
            85                  90
```

(2) INFORMATION FOR SEQ ID NO:48:

(i) SEQUENCE CHARACTERISTICS:
    (A) LENGTH: 90 amino acids
    (B) TYPE: amino acid
    (C) STRANDEDNESS: Not Relevant
    (D) TOPOLOGY: Not Relevant (ii) MOLECULE TYPE: peptide (ix) FEATURE:

(A) NAME/KEY: Peptide
            (B) LOCATION: 1..90
            (D) OTHER INFORMATION: /note= "amino acids 23-112 of
                Elongin C"

(xi) SEQUENCE DESCRIPTION: SEQ ID NO:48:

Ser Ser Asp Gly His Glu Phe Ile Val Lys Arg Glu His Ala Leu Thr
  1               5                  10                  15

Ser Gly Thr Ile Lys Ala Met Leu Ser Gly Pro Gly Gln Phe Ala Glu
                 20                  25                  30

Asn Glu Thr Asn Glu Val Asn Phe Arg Glu Ile Pro Ser His Val Leu
             35                  40                  45

Ser Lys Val Cys Met Tyr Phe Thr Tyr Lys Val Arg Tyr Thr Asn Ser
         50                  55                  60

Ser Thr Glu Ile Pro Glu Phe Pro Ile Ala Pro Glu Ile Ala Leu Glu
 65                  70                  75                  80

Leu Leu Met Ala Ala Asn Phe Leu Asp Cys
                 85                  90

(2) INFORMATION FOR SEQ ID NO:49:

(i) SEQUENCE CHARACTERISTICS:
            (A) LENGTH: 84 amino acids
            (B) TYPE: amino acid
            (C) STRANDEDNESS: Not Relevant
            (D) TOPOLOGY: Not Relevant (ii) MOLECULE TYPE: peptide (ix) FEATURE:
            (A) NAME/KEY: Peptide
            (B) LOCATION: 1..84
            (D) OTHER INFORMATION: /note= "amino acids 29-112 of
                Elongin C"

(xi) SEQUENCE DESCRIPTION: SEQ ID NO:49:

Phe Ile Val Lys Arg Glu His Ala Leu Thr Ser Gly Thr Ile Lys Ala
  1               5                  10                  15

Met Leu Ser Gly Pro Gly Gln Phe Ala Glu Asn Glu Thr Asn Glu Val
                 20                  25                  30

Asn Phe Arg Glu Ile Pro Ser His Val Leu Ser Lys Val Cys Met Tyr
             35                  40                  45

Phe Thr Tyr Lys Val Arg Tyr Thr Asn Ser Ser Thr Glu Ile Pro Glu
         50                  55                  60

Phe Pro Ile Ala Pro Glu Ile Ala Leu Glu Leu Leu Met Ala Ala Asn
 65                  70                  75                  80

Phe Leu Asp Cys (2) INFORMATION FOR SEQ ID NO:50:

(i) SEQUENCE CHARACTERISTICS:
            (A) LENGTH: 56 amino acids
            (B) TYPE: amino acid
            (C) STRANDEDNESS: Not Relevant
            (D) TOPOLOGY: Not Relevant (ii) MOLECULE TYPE: peptide (ix) FEATURE:
            (A) NAME/KEY: Peptide
            (B) LOCATION: 1..56
            (D) OTHER INFORMATION: /note= "amino acids 57-112 of
                Elongin C"

(xi) SEQUENCE DESCRIPTION: SEQ ID NO:50:

```
Thr Asn Glu Val Asn Phe Arg Glu Ile Pro Ser His Val Leu Ser Lys
 1               5                  10                  15

Val Cys Met Tyr Phe Thr Tyr Lys Val Arg Tyr Thr Asn Ser Ser Thr
                20                  25                  30

Glu Ile Pro Glu Phe Pro Ile Ala Pro Glu Ile Ala Leu Glu Leu Leu
                35                  40                  45

Met Ala Ala Asn Phe Leu Asp Cys
                50                  55
```

(2) INFORMATION FOR SEQ ID NO:51:

(i) SEQUENCE CHARACTERISTICS:
        (A) LENGTH: 97 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..97
        (D) OTHER INFORMATION: /note= "amino acids 1-97 of Elongin
            C"

(xi) SEQUENCE DESCRIPTION: SEQ ID NO:51:

```
Met Asp Gly Glu Glu Lys Thr Tyr Gly Gly Cys Glu Gly Pro Asp Ala
 1               5                  10                  15

Met Tyr Val Lys Leu Ile Ser Ser Asp Gly His Glu Phe Ile Val Lys
                20                  25                  30

Arg Glu His Ala Leu Thr Ser Gly Thr Ile Lys Ala Met Leu Ser Gly
                35                  40                  45

Pro Gly Gln Phe Ala Glu Asn Glu Thr Asn Glu Val Asn Phe Arg Glu
                50                  55                  60

Ile Pro Ser His Val Leu Ser Lys Val Cys Met Tyr Phe Thr Tyr Lys
65                  70                  75                  80

Val Arg Tyr Thr Asn Ser Ser Thr Glu Ile Pro Glu Phe Pro Ile Ala
                85                  90                  95

Pro
```

(2) INFORMATION FOR SEQ ID NO:52:

(i) SEQUENCE CHARACTERISTICS:
        (A) LENGTH: 83 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..83
        (D) OTHER INFORMATION: /note= "amino acids 1-83 of Elongin
            C"

(xi) SEQUENCE DESCRIPTION: SEQ ID NO:52:

```
Met Asp Gly Glu Glu Lys Thr Tyr Gly Gly Cys Glu Gly Pro Asp Ala
 1               5                  10                  15

Met Tyr Val Lys Leu Ile Ser Ser Asp Gly His Glu Phe Ile Val Lys
                20                  25                  30

Arg Glu His Ala Leu Thr Ser Gly Thr Ile Lys Ala Met Leu Ser Gly
                35                  40                  45
```

```
          Pro Gly Gln Phe Ala Glu Asn Glu Thr Asn Glu Val Asn Phe Arg Glu
              50                  55                  60

Ile Pro Ser His Val Leu Ser Lys Val Cys Met Tyr Phe Thr Tyr Lys
          65                  70                  75                  80

Val Arg Tyr (2) INFORMATION FOR SEQ ID NO:53:

(i) SEQUENCE CHARACTERISTICS:
          (A) LENGTH: 102 amino acids
          (B) TYPE: amino acid
          (C) STRANDEDNESS: Not Relevant
          (D) TOPOLOGY: Not Relevant (ii) MOLECULE TYPE: peptide (ix) FEATURE:
          (A) NAME/KEY: Peptide
          (B) LOCATION: 1..102
          (D) OTHER INFORMATION: /note= "amino acids 1-20 and 31-112
              of Elongin C"

(xi) SEQUENCE DESCRIPTION: SEQ ID NO:53:

Met Asp Gly Glu Glu Lys Thr Tyr Gly Gly Cys Glu Gly Pro Asp Ala
          1               5                   10                  15

Met Tyr Val Lys Val Lys Arg Glu His Ala Leu Thr Ser Gly Thr Ile
                          20                  25                  30

Lys Ala Met Leu Ser Gly Pro Gln Phe Ala Glu Asn Glu Thr Asn
                      35                  40                  45

Glu Val Asn Phe Arg Glu Ile Pro Ser His Val Leu Ser Lys Val Cys
              50                  55                  60

Met Tyr Phe Thr Tyr Lys Val Arg Tyr Thr Asn Ser Ser Thr Glu Ile
          65                  70                  75                  80

Pro Glu Phe Pro Ile Ala Pro Gly Ile Ala Leu Glu Leu Leu Met Ala
                          85                  90                  95

Ala Asn Phe Leu Asp Cys
                      100

(2) INFORMATION FOR SEQ ID NO:54:

(i) SEQUENCE CHARACTERISTICS:
          (A) LENGTH: 102 amino acids
          (B) TYPE: amino acid
          (C) STRANDEDNESS: Not Relevant
          (D) TOPOLOGY: Not Relevant (ii) MOLECULE TYPE: peptide (ix) FEATURE:
          (A) NAME/KEY: Peptide
          (B) LOCATION: 1..102
          (D) OTHER INFORMATION: /note= "amino acids 1-30 and 41-112
              of Elongin C"

(xi) SEQUENCE DESCRIPTION: SEQ ID NO:54:

Met Asp Gly Glu Glu Lys Thr Tyr Gly Gly Cys Glu Gly Pro Asp Ala
          1               5                   10                  15

Met Tyr Val Lys Leu Ile Ser Ser Asp Gly His Glu Phe Ile Thr Ile
                          20                  25                  30

Lys Ala Met Leu Ser Gly Pro Gln Phe Ala Glu Asn Glu Thr Asn
                      35                  40                  45

Glu Val Asn Phe Arg Glu Ile Pro Ser His Val Leu Ser Lys Val Cys
              50                  55                  60
```

Met Tyr Phe Thr Tyr Lys Val Arg Tyr Thr Asn Ser Ser Thr Glu Ile
65                  70                  75                  80

Pro Glu Phe Pro Ile Ala Pro Glu Ile Ala Leu Glu Leu Leu Met Ala
                85                  90                  95

Ala Asn Phe Leu Asp Cys
                100

(2) INFORMATION FOR SEQ ID NO:55:

(i) SEQUENCE CHARACTERISTICS:
       (A) LENGTH: 102 amino acids
       (B) TYPE: amino acid
       (C) STRANDEDNESS: Not Relevant
       (D) TOPOLOGY: Not Relevant (ii) MOLECULE TYPE: peptide (ix) FEATURE:
       (A) NAME/KEY: Peptide
       (B) LOCATION: 1..102
       (D) OTHER INFORMATION: /note= "amino acids 1-40 and 51-112 of Elongin C"

(xi) SEQUENCE DESCRIPTION: SEQ ID NO:55:

Met Asp Gly Glu Glu Lys Thr Tyr Gly Gly Cys Glu Gly Pro Asp Ala
1                   5                   10                  15

Met Tyr Val Lys Leu Ile Ser Ser Asp Gly His Glu Phe Ile Val Lys
                20                  25                  30

Arg Glu His Ala Leu Thr Ser Gly Gln Phe Ala Glu Asn Glu Thr Asn
                35                  40                  45

Glu Val Asn Phe Arg Glu Ile Pro Ser His Val Leu Ser Lys Val Cys
50                  55                  60

Met Tyr Phe Thr Tyr Lys Val Arg Tyr Thr Asn Ser Ser Thr Glu Ile
65                  70                  75                  80

Pro Glu Phe Pro Ile Ala Pro Glu Ile Ala Leu Glu Leu Leu Met Ala
                85                  90                  95

Ala Asn Phe Leu Asp Cys
                100

(2) INFORMATION FOR SEQ ID NO:56:

(i) SEQUENCE CHARACTERISTICS:
       (A) LENGTH: 102 amino acids
       (B) TYPE: amino acid
       (C) STRANDEDNESS: Not Relevant
       (D) TOPOLOGY: Not Relevant (ii) MOLECULE TYPE: peptide (ix) FEATURE:
       (A) NAME/KEY: Peptide
       (B) LOCATION: 1..102
       (D) OTHER INFORMATION: /note= "amino acids 1-50 and 61-112 of Elongin C"

(xi) SEQUENCE DESCRIPTION: SEQ ID NO:56:

Met Asp Gly Glu Glu Lys Thr Tyr Gly Gly Cys Glu Gly Pro Asp Ala
1                   5                   10                  15

Met Tyr Val Lys Leu Ile Ser Ser Asp Gly His Glu Phe Ile Val Lys
                20                  25                  30

Arg Glu His Ala Leu Thr Ser Gly Thr Ile Lys Ala Met Leu Ser Gly
                35                  40                  45

Pro Gly Asn Phe Arg Glu Ile Pro Ser His Val Leu Ser Lys Val Cys

```
                    50                  55                  60
Met Tyr Phe Thr Tyr Lys Val Arg Tyr Thr Asn Ser Ser Thr Glu Ile
 65                  70                  75                  80

Pro Glu Phe Pro Ile Ala Pro Glu Ile Ala Leu Glu Leu Leu Met Ala
                    85                  90                  95

Ala Asn Phe Leu Asp Cys
                100
```

(2) INFORMATION FOR SEQ ID NO:57:

(i) SEQUENCE CHARACTERISTICS:
        (A) LENGTH: 102 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..102
        (D) OTHER INFORMATION: /note= "amino acids 1-60 and 71-112
           of Elongin C"

(xi) SEQUENCE DESCRIPTION: SEQ ID NO:57:

```
Met Asp Gly Glu Glu Lys Thr Tyr Gly Gly Cys Glu Gly Pro Asp Ala
 1                   5                  10                  15

Met Tyr Val Lys Leu Ile Ser Ser Asp Gly His Glu Phe Ile Val Lys
                    20                  25                  30

Arg Glu His Ala Leu Thr Ser Gly Thr Ile Lys Ala Met Leu Ser Gly
                    35                  40                  45

Pro Gly Gln Phe Ala Glu Asn Glu Thr Asn Glu Val Ser Lys Val Cys
                50                  55                  60

Met Tyr Phe Thr Tyr Lys Val Arg Tyr Thr Asn Ser Ser Thr Glu Ile
 65                  70                  75                  80

Pro Glu Phe Pro Ile Ala Pro Glu Ile Ala Leu Glu Leu Leu Met Ala
                    85                  90                  95

Ala Asn Phe Leu Asp Cys
                100
```

(2) INFORMATION FOR SEQ ID NO:58:

(i) SEQUENCE CHARACTERISTICS:
        (A) LENGTH: 102 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..102
        (D) OTHER INFORMATION: /note= "amino acids 1-70 and 81-112
           of Elongin C"

(xi) SEQUENCE DESCRIPTION: SEQ ID NO:58:

```
Met Asp Gly Glu Glu Lys Thr Tyr Gly Gly Cys Glu Gly Pro Asp Ala
 1                   5                  10                  15

Met Tyr Val Lys Leu Ile Ser Ser Asp Gly His Glu Phe Ile Val Lys
                    20                  25                  30

Arg Glu His Ala Leu Thr Ser Gly Thr Ile Lys Ala Met Leu Ser Gly
                    35                  40                  45
```

```
Pro Gly Gln Phe Ala Glu Asn Glu Thr Asn Glu Val Asn Phe Arg Glu
    50                  55                  60

Ile Pro Ser His Val Leu Val Arg Tyr Thr Asn Ser Ser Thr Glu Ile
65                  70                  75                  80

Pro Glu Phe Pro Ile Ala Pro Glu Ile Ala Leu Glu Leu Leu Met Ala
                85                  90                  95

Ala Asn Phe Leu Asp Cys
                100
```

(2) INFORMATION FOR SEQ ID NO:59:

(i) SEQUENCE CHARACTERISTICS:
        (A) LENGTH: 102 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..102
        (D) OTHER INFORMATION: /note= "amino acids 1-80 and 91-112
            of Elongin C"

(xi) SEQUENCE DESCRIPTION: SEQ ID NO:59:

```
Met Asp Gly Glu Glu Lys Thr Tyr Gly Gly Cys Glu Gly Pro Asp Ala
1               5                   10                  15

Met Tyr Val Lys Leu Ile Ser Ser Asp Gly His Glu Phe Ile Val Lys
                20                  25                  30

Arg Glu His Ala Leu Thr Ser Gly Thr Ile Lys Ala Met Leu Ser Gly
                35                  40                  45

Pro Gly Gln Phe Ala Glu Asn Glu Thr Asn Glu Val Asn Phe Arg Glu
    50                  55                  60

Ile Pro Ser His Val Leu Ser Lys Val Cys Met Tyr Phe Thr Tyr Lys
65                  70                  75                  80

Pro Glu Phe Pro Ile Ala Pro Glu Ile Ala Leu Glu Leu Leu Met Ala
                85                  90                  95

Ala Asn Phe Leu Asp Cys
                100
```

(2) INFORMATION FOR SEQ ID NO:60:

(i) SEQUENCE CHARACTERISTICS:
        (A) LENGTH: 102 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..102
        (D) OTHER INFORMATION: /note= "amino acids 1-90 and
            101-112 of Elongin C"

(xi) SEQUENCE DESCRIPTION: SEQ ID NO:60:

```
Met Asp Gly Glu Glu Lys Thr Tyr Gly Gly Cys Glu Gly Pro Asp Ala
1               5                   10                  15

Met Tyr Val Lys Leu Ile Ser Ser Asp Gly His Glu Phe Ile Val Lys
                20                  25                  30

Arg Glu His Ala Leu Thr Ser Gly Thr Ile Lys Ala Met Leu Ser Gly
                35                  40                  45
```

```
    Pro Gly Gln Phe Ala Glu Asn Glu Thr Asn Val Asn Phe Arg Glu
        50                  55                  60

Ile Pro Ser His Val Leu Ser Lys Val Cys Met Tyr Phe Thr Tyr Lys
    65                  70                  75                  80

Val Arg Tyr Thr Asn Ser Ser Thr Glu Ile Leu Glu Leu Leu Met Ala
                        85                  90                  95

Ala Asn Phe Leu Asp Cys
                100

(2) INFORMATION FOR SEQ ID NO:61:

(i) SEQUENCE CHARACTERISTICS:
        (A) LENGTH: 112 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Protein
        (B) LOCATION: 1..112
        (D) OTHER INFORMATION: /note= "amino acids 19-21 of
            Elongin C mutated to alanine"

(xi) SEQUENCE DESCRIPTION: SEQ ID NO:61:

Met Asp Gly Glu Glu Lys Thr Tyr Gly Gly Cys Glu Gly Pro Asp Ala
    1               5                   10                  15

Met Tyr Ala Ala Ala Ile Ser Ser Asp Gly His Glu Phe Ile Val Lys
                    20                  25                  30

Arg Glu His Ala Leu Thr Ser Gly Thr Ile Lys Ala Met Leu Ser Gly
                    35                  40                  45

Pro Gly Gln Phe Ala Glu Asn Glu Thr Asn Glu Val Asn Phe Arg Glu
        50                  55                  60

Ile Pro Ser His Val Leu Ser Lys Val Cys Met Tyr Phe Thr Tyr Lys
    65                  70                  75                  80

Val Arg Tyr Thr Asn Ser Ser Thr Glu Ile Pro Glu Phe Pro Ile Ala
                        85                  90                  95

Pro Glu Ile Ala Leu Glu Leu Leu Met Ala Ala Asn Phe Leu Asp Cys
                100                 105                 110

(2) INFORMATION FOR SEQ ID NO:62:

(i) SEQUENCE CHARACTERISTICS:
        (A) LENGTH: 112 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Protein
        (B) LOCATION: 1..112
        (D) OTHER INFORMATION: /note= "amino acids 22-24 of
            Elongin C mutated to alanine"

(xi) SEQUENCE DESCRIPTION: SEQ ID NO:62:

Met Asp Gly Glu Glu Lys Thr Tyr Gly Gly Cys Glu Gly Pro Asp Ala
    1               5                   10                  15

Met Tyr Val Lys Leu Ala Ala Ala Asp Gly His Glu Phe Ile Val Lys
                    20                  25                  30

Arg Glu His Ala Leu Thr Ser Gly Thr Ile Lys Ala Met Leu Ser Gly
```

```
                 35                  40                  45
Pro Gly Gln Phe Ala Glu Asn Glu Thr Asn Glu Val Asn Phe Arg Glu
    50                  55                  60
Ile Pro Ser His Val Leu Ser Lys Val Cys Met Tyr Phe Thr Tyr Lys
65                  70                  75                  80
Val Arg Tyr Thr Asn Ser Ser Thr Glu Ile Pro Glu Phe Pro Ile Ala
                85                  90                  95
Pro Glu Ile Ala Leu Glu Leu Leu Met Ala Ala Asn Phe Leu Asp Cys
                100                 105                 110
```

(2) INFORMATION FOR SEQ ID NO:63:

(i) SEQUENCE CHARACTERISTICS:
        (A) LENGTH: 112 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Protein
        (B) LOCATION: 1..112
        (D) OTHER INFORMATION: /note= "amino acids 25-27 of
            Elongin C mutated to alanine"

(xi) SEQUENCE DESCRIPTION: SEQ ID NO:63:

```
Met Asp Gly Glu Glu Lys Thr Tyr Gly Gly Cys Glu Gly Pro Asp Ala
1               5                   10                  15
Met Tyr Val Lys Leu Ile Ser Ser Ala Ala Ala Glu Phe Ile Val Lys
                20                  25                  30
Arg Glu His Ala Leu Thr Ser Gly Thr Ile Lys Ala Met Leu Ser Gly
                35                  40                  45
Pro Gly Gln Phe Ala Glu Asn Glu Thr Asn Glu Val Asn Phe Arg Glu
    50                  55                  60
Ile Pro Ser His Val Leu Ser Lys Val Cys Met Tyr Phe Thr Tyr Lys
65                  70                  75                  80
Val Arg Tyr Thr Asn Ser Ser Thr Glu Ile Pro Glu Phe Pro Ile Ala
                85                  90                  95
Pro Glu Ile Ala Leu Glu Leu Leu Met Ala Ala Asn Phe Leu Asp Cys
                100                 105                 110
```

(2) INFORMATION FOR SEQ ID NO:64:

(i) SEQUENCE CHARACTERISTICS:
        (A) LENGTH: 112 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Protein
        (B) LOCATION: 1..112
        (D) OTHER INFORMATION: /note= "amino acids 28-30 of
            Elongin C mutated to alanine"

(xi) SEQUENCE DESCRIPTION: SEQ ID NO:64:

```
Met Asp Gly Glu Glu Lys Thr Tyr Gly Gly Cys Glu Gly Pro Asp Ala
1               5                   10                  15
Met Tyr Val Lys Leu Ile Ser Ser Asp Gly His Ala Ala Ala Val Lys
                20                  25                  30
```

```
      Arg Glu His Ala Leu Thr Ser Gly Thr Ile Lys Ala Met Leu Ser Gly
               35                  40                  45

Pro Gly Gln Phe Ala Glu Asn Glu Thr Asn Glu Val Asn Phe Arg Glu
               50                  55                  60

Ile Pro Ser His Val Leu Ser Lys Val Cys Met Tyr Phe Thr Tyr Lys
       65                  70                  75                  80

Val Arg Tyr Thr Asn Ser Ser Thr Glu Ile Pro Glu Phe Pro Ile Ala
                           85                  90                  95

Pro Glu Ile Ala Leu Glu Leu Leu Met Ala Ala Asn Phe Leu Asp Cys
                       100                 105                 110
```

(2) INFORMATION FOR SEQ ID NO:65:

(i) SEQUENCE CHARACTERISTICS:
        (A) LENGTH: 112 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Protein
        (B) LOCATION: 1..112
        (D) OTHER INFORMATION: /note= "amino acids 89-91 of
            Elongin C mutated to alanine"

(xi) SEQUENCE DESCRIPTION: SEQ ID NO:65:

```
      Met Asp Gly Glu Glu Lys Thr Tyr Gly Gly Cys Glu Gly Pro Asp Ala
        1               5                  10                  15

Met Tyr Val Lys Leu Ile Ser Ser Asp Gly His Glu Phe Ile Val Lys
                       20                  25                  30

Arg Glu His Ala Leu Thr Ser Gly Thr Ile Lys Ala Met Leu Ser Gly
               35                  40                  45

Pro Gly Gln Phe Ala Glu Asn Glu Thr Asn Glu Val Asn Phe Arg Glu
               50                  55                  60

Ile Pro Ser His Val Leu Ser Lys Val Cys Met Tyr Phe Thr Tyr Lys
       65                  70                  75                  80

Val Arg Tyr Thr Asn Ser Ser Thr Ala Ala Ala Glu Phe Pro Ile Ala
                           85                  90                  95

Pro Glu Ile Ala Leu Glu Leu Leu Met Ala Ala Asn Phe Leu Asp Cys
                       100                 105                 110
```

(2) INFORMATION FOR SEQ ID NO:66:

(i) SEQUENCE CHARACTERISTICS:
        (A) LENGTH: 112 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Protein
        (B) LOCATION: 1..112
        (D) OTHER INFORMATION: /note= "amino acids 92-94 Elongin C
            mutated to alanine"

(xi) SEQUENCE DESCRIPTION: SEQ ID NO:66:

```
      Met Asp Gly Glu Glu Lys Thr Tyr Gly Gly Cys Glu Gly Pro Asp Ala
        1               5                  10                  15

Met Tyr Val Lys Leu Ile Ser Ser Asp Gly His Glu Phe Ile Val Lys
                       20                  25                  30
```

```
Arg Glu His Ala Leu Thr Ser Gly Thr Ile Lys Ala Met Leu Ser Gly
        35                  40                  45

Pro Gly Gln Phe Ala Glu Asn Glu Thr Asn Glu Val Asn Phe Arg Glu
    50                  55                  60

Ile Pro Ser His Val Leu Ser Lys Val Cys Met Tyr Phe Thr Tyr Lys
65                  70                  75                  80

Val Arg Tyr Thr Asn Ser Ser Thr Glu Ile Pro Ala Ala Ala Ile Ala
                85                  90                  95

Pro Glu Ile Ala Leu Glu Leu Leu Met Ala Ala Asn Phe Leu Asp Cys
                100                 105                 110
```

(2) INFORMATION FOR SEQ ID NO:67:

(i) SEQUENCE CHARACTERISTICS:
        (A) LENGTH: 112 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Protein
        (B) LOCATION: 1..112
        (D) OTHER INFORMATION: /note= "amino acids 95-97 of
            Elongin C mutated to alanine"

(xi) SEQUENCE DESCRIPTION: SEQ ID NO:67:

```
Met Asp Gly Glu Glu Lys Thr Tyr Gly Gly Cys Glu Gly Pro Asp Ala
1               5                   10                  15

Met Tyr Val Lys Leu Ile Ser Ser Asp Gly His Glu Phe Ile Val Lys
                20                  25                  30

Arg Glu His Ala Leu Thr Ser Gly Thr Ile Lys Ala Met Leu Ser Gly
        35                  40                  45

Pro Gly Gln Phe Ala Glu Asn Glu Thr Asn Glu Val Asn Phe Arg Glu
    50                  55                  60

Ile Pro Ser His Val Leu Ser Lys Val Cys Met Tyr Phe Thr Tyr Lys
65                  70                  75                  80

Val Arg Tyr Thr Asn Ser Ser Thr Glu Ile Pro Glu Phe Pro Ala Ala
                85                  90                  95

Ala Glu Ile Ala Leu Glu Leu Leu Met Ala Ala Asn Phe Leu Asp Cys
                100                 105                 110
```

(2) INFORMATION FOR SEQ ID NO:68:

(i) SEQUENCE CHARACTERISTICS:
        (A) LENGTH: 112 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Protein
        (B) LOCATION: 1..112
        (D) OTHER INFORMATION: /note= "amino acids 98-100 of
            Elongin C mutated to alanine"

(xi) SEQUENCE DESCRIPTION: SEQ ID NO:68:

```
Met Asp Gly Glu Glu Lys Thr Tyr Gly Gly Cys Glu Gly Pro Asp Ala
1               5                   10                  15

Met Tyr Val Lys Leu Ile Ser Ser Asp Gly His Glu Phe Ile Val Lys
```

```
            20                  25                  30

Arg Glu His Ala Leu Thr Ser Gly Thr Ile Lys Ala Met Leu Ser Gly
        35                  40                  45

Pro Gly Gln Phe Ala Glu Asn Glu Thr Asn Glu Val Asn Phe Arg Glu
    50                  55                  60

Ile Pro Ser His Val Leu Ser Lys Val Cys Met Tyr Phe Thr Tyr Lys
65                  70                  75                  80

Val Arg Tyr Thr Asn Ser Ser Thr Glu Ile Pro Glu Phe Pro Ile Ala
                85                  90                  95

Pro Ala Ala Ala Leu Glu Leu Leu Met Ala Ala Asn Phe Leu Asp Cys
            100                 105                 110
```

(2) INFORMATION FOR SEQ ID NO:69:

(i) SEQUENCE CHARACTERISTICS:
        (A) LENGTH: 112 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Protein
        (B) LOCATION: 1..112
        (D) OTHER INFORMATION: /note= "amino acids 101-103 of
            Elongin C mutated to alanine"

(xi) SEQUENCE DESCRIPTION: SEQ ID NO:69:

```
Met Asp Gly Glu Glu Lys Thr Tyr Gly Gly Cys Glu Gly Pro Asp Ala
1               5                   10                  15

Met Tyr Val Lys Leu Ile Ser Ser Asp Gly His Glu Phe Ile Val Lys
            20                  25                  30

Arg Glu His Ala Leu Thr Ser Gly Thr Ile Lys Ala Met Leu Ser Gly
        35                  40                  45

Pro Gly Gln Phe Ala Glu Asn Glu Thr Asn Glu Val Asn Phe Arg Glu
    50                  55                  60

Ile Pro Ser His Val Leu Ser Lys Val Cys Met Tyr Phe Thr Tyr Lys
65                  70                  75                  80

Val Arg Tyr Thr Asn Ser Ser Thr Glu Ile Pro Glu Phe Pro Ile Ala
                85                  90                  95

Pro Glu Ile Ala Ala Ala Ala Leu Met Ala Ala Asn Phe Leu Asp Cys
            100                 105                 110
```

(2) INFORMATION FOR SEQ ID NO:70:

(i) SEQUENCE CHARACTERISTICS:
        (A) LENGTH: 112 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Protein
        (B) LOCATION: 1..112
        (D) OTHER INFORMATION: /note= "amino acids 104-106 of
            Elongin C mutated to alanine"

(xi) SEQUENCE DESCRIPTION: SEQ ID NO:70:

```
Met Asp Gly Glu Glu Lys Thr Tyr Gly Gly Cys Glu Gly Pro Asp Ala
1               5                   10                  15
```

Met Tyr Val Lys Leu Ile Ser Ser Asp Gly His Glu Phe Ile Val Lys
            20                  25                  30

Arg Glu His Ala Leu Thr Ser Gly Thr Ile Lys Ala Met Leu Ser Gly
        35                  40                  45

Pro Gly Gln Phe Ala Glu Asn Glu Thr Asn Glu Val Asn Phe Arg Glu
    50                  55                  60

Ile Pro Ser His Val Leu Ser Lys Val Cys Met Tyr Phe Thr Tyr Lys
65                  70                  75                  80

Val Arg Tyr Thr Asn Ser Ser Thr Glu Ile Pro Glu Phe Pro Ile Ala
                85                  90                  95

Pro Glu Ile Ala Leu Glu Leu Ala Ala Ala Ala Asn Phe Leu Asp Cys
                100                 105                 110

(2) INFORMATION FOR SEQ ID NO:71:

(i) SEQUENCE CHARACTERISTICS:
       (A) LENGTH: 112 amino acids
       (B) TYPE: amino acid
       (C) STRANDEDNESS: Not Relevant
       (D) TOPOLOGY: Not Relevant (ii) MOLECULE TYPE: peptide (ix) FEATURE:
       (A) NAME/KEY: Protein
       (B) LOCATION: 1..112
       (D) OTHER INFORMATION: /note= "amino acids 107-109 of
           Elongin C mutated to alanine"

(xi) SEQUENCE DESCRIPTION: SEQ ID NO:71:

Met Asp Gly Glu Glu Lys Thr Tyr Gly Gly Cys Glu Gly Pro Asp Ala
1               5                   10                  15

Met Tyr Val Lys Leu Ile Ser Ser Asp Gly His Glu Phe Ile Val Lys
            20                  25                  30

Arg Glu His Ala Leu Thr Ser Gly Thr Ile Lys Ala Met Leu Ser Gly
        35                  40                  45

Pro Gly Gln Phe Ala Glu Asn Glu Thr Asn Glu Val Asn Phe Arg Glu
    50                  55                  60

Ile Pro Ser His Val Leu Ser Lys Val Cys Met Tyr Phe Thr Tyr Lys
65                  70                  75                  80

Val Arg Tyr Thr Asn Ser Ser Thr Glu Ile Pro Glu Phe Pro Ile Ala
                85                  90                  95

Pro Glu Ile Ala Leu Glu Leu Leu Met Ala Ala Ala Ala Leu Asp Cys
                100                 105                 110

(2) INFORMATION FOR SEQ ID NO:72:

(i) SEQUENCE CHARACTERISTICS:
       (A) LENGTH: 112 amino acids
       (B) TYPE: amino acid
       (C) STRANDEDNESS: Not Relevant
       (D) TOPOLOGY: Not Relevant (ii) MOLECULE TYPE: peptide (ix) FEATURE:
       (A) NAME/KEY: Protein
       (B) LOCATION: 1..112
       (D) OTHER INFORMATION: /note= "amino acids 110-112 of
           Elongin C mutated to alanine"

(xi) SEQUENCE DESCRIPTION: SEQ ID NO:72:

Met Asp Gly Glu Glu Lys Thr Tyr Gly Gly Cys Glu Gly Pro Asp Ala
1               5                   10                  15

```
       Met Tyr Val Lys Leu Ile Ser Ser Asp Gly His Glu Phe Ile Val Lys
                20                  25                  30

Arg Glu His Ala Leu Thr Ser Gly Thr Ile Lys Ala Met Leu Ser Gly
                35                  40                  45

Pro Gly Gln Phe Ala Glu Asn Glu Thr Asn Glu Val Asn Phe Arg Glu
                50                  55                  60

Ile Pro Ser His Val Leu Ser Lys Val Cys Met Tyr Phe Thr Tyr Lys
       65                  70                  75                  80

Val Arg Tyr Thr Asn Ser Ser Thr Glu Ile Pro Glu Phe Pro Ile Ala
                        85                  90                  95

Pro Glu Ile Ala Leu Glu Leu Leu Met Ala Ala Asn Phe Ala Ala Ala
                        100                 105                 110
```

(2) INFORMATION FOR SEQ ID NO:73:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..5
        (D) OTHER INFORMATION: /note= "amino acids 18-22 of
            Elongin C"

(xi) SEQUENCE DESCRIPTION: SEQ ID NO:73:

```
   Tyr Val Lys Leu Ile
   1               5
```

(2) INFORMATION FOR SEQ ID NO:74:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..13
        (D) OTHER INFORMATION: /note= "amino acids 18-30 of
            Elongin C"

(xi) SEQUENCE DESCRIPTION: SEQ ID NO:74:

```
   Tyr Val Lys Leu Ile Ser Ser Asp Gly His Glu Phe Ile
   1               5                   10
```

(2) INFORMATION FOR SEQ ID NO:75:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..24
        (D) OTHER INFORMATION: /note= "amino acids 89-112 of
            Elongin C"

(xi) SEQUENCE DESCRIPTION: SEQ ID NO:75:

Glu Ile Pro Glu Phe Pro Ile Ala Pro Glu Ile Ala Leu Glu Leu Leu
    1               5                   10                  15

Met Ala Ala Asn Phe Leu Asp Cys
                20

(2) INFORMATION FOR SEQ ID NO:76:

(i) SEQUENCE CHARACTERISTICS:
        (A) LENGTH: 52 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..52
        (D) OTHER INFORMATION: /note= "amino acids 61-112 of
            Elongin C"

(xi) SEQUENCE DESCRIPTION: SEQ ID NO:76:

Asn Phe Arg Glu Ile Pro Ser His Val Leu Ser Lys Val Cys Met Tyr
    1               5                   10                  15

Phe Thr Tyr Lys Val Arg Tyr Thr Asn Ser Ser Thr Glu Ile Pro Glu
                20                  25                  30

Phe Pro Ile Ala Pro Glu Ile Ala Leu Glu Leu Leu Met Ala Ala Asn
                35                  40                  45

Phe Leu Asp Cys
                50

(2) INFORMATION FOR SEQ ID NO:77:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:77:

GAGTTGGTCA GTGCTCGCGT GGTCAAGAAC AGGCTTCAGT AGATCAAATG G                51

(2) INFORMATION FOR SEQ ID NO:78:

(i) SEQUENCE CHARACTERISTICS:
        (A) LENGTH: 31 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..16
        (D) OTHER INFORMATION: /note= "amino acids 148-178 of VHL
            protein"

(xi) SEQUENCE DESCRIPTION: SEQ ID NO:78:

Phe Ala Asn Ile Thr Leu Pro Val Tyr Thr Leu Lys Glu Arg Cys Leu
    1               5                   10                  15

Gln Val Val Arg Ser Leu Val Lys Pro Glu Asn Tyr Arg Arg Leu
                20                  25                  30

(2) INFORMATION FOR SEQ ID NO:79:

(i) SEQUENCE CHARACTERISTICS:
        (A) LENGTH: 773 amino acids
        (B) TYPE: amino acid
        (D) TOPOLOGY: linear (ii) MOLECULE TYPE: protein (xi) SEQUENCE DESCRIPTION: SEQ ID NO:79:

```
Met Ala Ala Glu Ser Ala Leu Gln Val Val Glu Lys Leu Gln Ala Arg
 1               5                  10                  15

Leu Ala Ala Asn Pro Asp Pro Lys Lys Leu Leu Lys Tyr Leu Lys Lys
                20                  25                  30

Leu Ser Val Leu Pro Ile Thr Val Asp Ile Leu Val Glu Thr Gly Val
            35                  40                  45

Gly Lys Thr Val Asn Ser Phe Arg Lys His Glu Gln Val Gly Asn Phe
        50                  55                  60

Ala Arg Asp Leu Val Ala Gln Trp Lys Lys Leu Val Pro Val Glu Arg
 65                  70                  75                  80

Asn Asn Glu Ala Glu Asp Gln Asp Phe Glu Lys Ser Asn Ser Arg Lys
                85                  90                  95

Arg Pro Arg Asp Val Pro Gln Gln Glu Glu Ala Glu Gly Asn Tyr
                100                 105                 110

Gln Glu Ser Trp Gln Ala Ser Gly Ser Gln Pro Tyr Ser Pro Glu His
            115                 120                 125

Arg Gln Lys Lys His Arg Lys Leu Pro Glu Leu Glu Arg Pro His Lys
130                 135                 140

Val Ala His Gly His Glu Arg Arg Asp Glu Arg Lys Arg Cys His Lys
145                 150                 155                 160

Val Ser Pro Pro Tyr Ser Ser Asp Pro Glu Ser Ser Asp Tyr Gly His
                165                 170                 175

Val Gln Ser Pro Pro Pro Ser Ser Pro His Gln Met Tyr Thr Asp Leu
            180                 185                 190

Ser Arg Ser Pro Glu Met Asp Gln Glu Pro Ile Val Ser His Pro Lys
        195                 200                 205

Pro Gly Lys Val His Ser Asn Thr Phe Gln Asp Arg Leu Gly Val Ser
210                 215                 220

His Leu Gly Glu His Gln Gly Lys Gly Ala Val Ser Gln Asn Lys Pro
225                 230                 235                 240

His Lys Ser Ser His Lys Glu Leu Arg Pro Val Asp Ala Arg Gly Asp
                245                 250                 255

Glu Lys Ser Ser Val Met Gly Arg Glu Lys Ser His Lys Ala Ser Ser
            260                 265                 270

Lys Glu Glu Ser Arg Arg Leu Leu Ser Glu Asp Ser Ala Lys Glu Lys
        275                 280                 285

Leu Pro Ser Ser Val Val Lys Ser Glu Lys Asp Arg Glu Gly Asn Ser
    290                 295                 300

Leu Lys Lys Lys Leu Ser Pro Ala Leu Asp Val Ala Ser Asp Asn His
305                 310                 315                 320

Phe Lys Lys Pro Lys His Lys Asp Ser Glu Lys Ile Lys Ser Asp Lys
                325                 330                 335

Asn Lys Gln Ser Val Asp Ser Val Asp Ser Gly Arg Gly Thr Gly Asp
            340                 345                 350
```

-continued

```
Pro Leu Pro Arg Ala Lys Asp Lys Val Pro Asn Asn Leu Lys Ala Gln
            355                 360                 365

Glu Gly Lys Val Arg Thr Asn Ser Asp Arg Lys Ser Pro Gly Ser Leu
    370                 375                 380

Pro Lys Val Glu Glu Met Asp Met Asp Glu Phe Glu Gln Pro Thr
385                 390                 395                 400

Met Ser Phe Glu Ser Tyr Leu Ser Tyr Asp Gln Pro Arg Lys Lys Lys
                405                 410                 415

Lys Lys Val Val Lys Thr Ser Gly Thr Ala Leu Gly Glu Lys Gly Leu
            420                 425                 430

Lys Lys Lys Asp Ser Lys Ser Thr Ser Lys Asn Leu Asn Ser Ala Gln
            435                 440                 445

Lys Leu Pro Lys Ala Asn Glu Asn Lys Ser Asp Lys Leu Gln Pro Ala
    450                 455                 460

Gly Ala Glu Pro Thr Arg Pro Arg Lys Val Pro Thr Asp Val Leu Pro
465                 470                 475                 480

Ala Leu Pro Asp Ile Pro Leu Pro Ala Ile Gln Thr Asn Tyr Arg Pro
                485                 490                 495

Leu Pro Ser Leu Glu Leu Ile Ser Ser Phe Gln Pro Lys Arg Lys Ala
                500                 505                 510

Phe Ser Ser Pro Gln Glu Glu Glu Ala Gly Phe Thr Gly Arg Arg
            515                 520                 525

Met Asn Ser Lys Met Gln Val Tyr Ser Gly Ser Lys Cys Ala Tyr Leu
    530                 535                 540

Pro Lys Met Met Thr Leu His Gln Gln Cys Ile Arg Val Leu Lys Asn
545                 550                 555                 560

Asn Ile Asp Ser Ile Phe Glu Val Gly Gly Val Pro Tyr Ser Val Leu
                565                 570                 575

Glu Pro Val Leu Glu Arg Cys Thr Pro Asp Gln Leu Tyr Arg Ile Glu
                580                 585                 590

Glu Cys Asn His Val Leu Ile Glu Glu Thr Asp Gln Leu Trp Lys Val
            595                 600                 605

His Cys His Arg Asp Phe Lys Glu Glu Arg Pro Glu Glu Tyr Glu Ser
    610                 615                 620

Trp Arg Glu Met Tyr Leu Arg Leu Gln Asp Ala Arg Glu Gln Arg Leu
625                 630                 635                 640

Arg Leu Leu Thr Asn Asn Ile Arg Ser Ala His Ala Asn Lys Pro Lys
                645                 650                 655

Gly Arg Gln Ala Lys Met Ala Phe Val Asn Ser Val Ala Lys Pro Pro
                660                 665                 670

Arg Asp Val Arg Arg Gln Glu Lys Phe Gly Thr Gly Gly Ala Ala
            675                 680                 685

Val Pro Glu Lys Val Arg Ile Lys Pro Ala Pro Tyr Thr Thr Gly Ser
            690                 695                 700

Ser His Val Pro Ala Ser Asn Ser Ser Ser Phe His Ser Ser Pro
705                 710                 715                 720

Glu Glu Leu Ala Tyr Glu Gly Pro Ser Thr Ser Ser Ala His Leu Ala
                725                 730                 735

Pro Val Ala Ser Ser Val Ser Tyr Asp Pro Arg Lys Pro Ala Val
                740                 745                 750
```

```
Lys Lys Ile Ala Pro Met Met Ala Lys Thr Ile Lys Ala Phe Lys Asn
        755                 760                 765

Arg Phe Ser Arg Arg
        770
```